US012760270B2

(12) United States Patent
Azarin et al.

(10) Patent No.: US 12,760,270 B2
(45) Date of Patent: Oct. 13, 2026

(54) COMPOSITIONS AND METHODS FOR PRODUCING PLACENTAL CELLS

(71) Applicant: Regents of the University of Minnesota, Minneapolis, MN (US)

(72) Inventors: Samira Azarin, Minneapolis, MN (US); Casim A. Sarkar, Minneapolis, MN (US); Kristen A. Lemke, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 17/948,024

(22) Filed: Sep. 19, 2022

(65) Prior Publication Data

US 2023/0183643 A1 Jun. 15, 2023

Related U.S. Application Data

(60) Provisional application No. 63/245,531, filed on Sep. 17, 2021.

(51) Int. Cl.
*C12N 5/073* (2010.01)

(52) U.S. Cl.
CPC ........ *C12N 5/0605* (2013.01); *C12N 2500/38* (2013.01); *C12N 2501/415* (2013.01); *C12N 2506/45* (2013.01)

(58) Field of Classification Search
None
See application file for complete search history.

(56) References Cited

U.S. PATENT DOCUMENTS

| | | | | |
|---|---|---|---|---|
| 6,630,349 | B1 | 10/2003 | Rossant et al. | |
| 8,057,789 | B2 | 11/2011 | Hariri | |
| 10,435,666 | B2 | 10/2019 | Xu et al. | |
| 2023/0220334 | A1* | 7/2023 | Singec ................. | C12N 5/0605 435/366 |

FOREIGN PATENT DOCUMENTS

| | | | |
|---|---|---|---|
| CA | 2635253 | A1 | 7/2007 |
| CN | 111304156 | A | 6/2020 |
| EP | 2908629 | B1 | 2/2019 |
| WO | 2015125926 | A1 | 8/2015 |
| WO | 2016005985 | A2 | 1/2016 |
| WO | 2021041835 | A1 | 3/2021 |

OTHER PUBLICATIONS

2-Mercaptoethanol. ThermoFisher Scientific. (accessed at: https://web.archive.org/web/20150908200714/https://www.thermofisher.com/order/catalog/product/21985023)(Year: 2015).*

L-Glutamine & GlutaMAX Cell Culture Supplements. ThermoFisher Scientific. (accessed at https://web.archive.org/web/ 20190721110130/https://www.thermofisher.com/US/en/home/life-science/cell-culture/mammalian-cell-culture/media-supplements/ glutamax-media.html) (Year: 2019).*

I-Alanyl-I-glutamine. PubChem. (accessed at: https://web.archive.org/web/20200815030328/https://pubchem.ncbi.nlm.nih.gov/compound/I-Alanyl-I-glutamine)(Year: 2020).*

Chen et al. Inhibition of Tgfb signaling by endogenous retinoic acid is essential for primary lung bud induction. Development. Aug. 2007;134(16):2969-79. Epub Jul. 18, 2007. (Year: 2007).*

Bain, G. , et al., "Retinoic Acid Promotes Neural and Represses Mesodermal Gene Expression in Mouse Embryonic Stem Cells in Culture", Biochemical and Biophysical Research Communications 223 (3), 691-694 (1996).

Blakeley, P. , et al., "Defining the three cell lineages of the human blastocyst by single-cell RNA-seq", Development 142(18), 3151-3165 (2015).

Cambuli, F , et al., "Epigenetic memory of the first cell fate decision prevents complete ES cell reprogramming into trophoblast", Nature Communications 5 (5538), 1-16 (2014).

Dani, C. , et al., "Differentiation of embryonic stem cells into adipocytes in vitro", J Cell Sci 110 (Pt 11), 1279-1285 (1997).

Dong, C. , et al., "Derivation of trophoblast stem cells from naïve human pluripotent stem cells", Elife 9, e52504, 1-26 (2020).

Ezashi, D, et al., "Modeling the Placenta with Stem Cells", N Engl J Med 381, 1681-1683 (2019).

Guo, G. , et al., "Human naive epiblast cells possess unrestricted lineage potential", Cell Stem Cell 28, 1040-1056 (2021).

Horii, M , et al., "An Improved Two-Step Protocol for Trophoblast Differentiation of Human Pluripotent Stem Cells", Current Protocols in Stem Cell Biology 50 (1), e96, 31 pages (2019).

Horii, M. , et al., "Human pluripotent stem cells as a model of trophoblast differentiation in both normal development and disease", PNAS 113(27), E3882-E3891 (2016).

Horii, M , et al., "Modeling preeclampsia using human induced pluripotent stem cells", Sci Rep 11 (1), 5877, 16 pages (2021).

Houle, M. , et al., "Retinoic Acid Regulation of Cdx1: an Indirect Mechanism for Retinoids and Vertebral Specification", Mol Cell Biol 20(17), 6579-6586 (2000).

Io, S, et al., "Capturing Human Trophoblast Development with Naïve Pluripotent Stem Cells In Vitro", bioRxiv preprint doi: https://doi.org/10.1101/2020.12.17.416800, 51 pages (2020).

Jagtap, S , et al., "All-trans retinoic acid and basic fibroblast growth factor synergistically direct pluripotent human embryonic stem cells to extraembryonic lineages", Stem Cell Research 10, 228-240 (2013).

(Continued)

*Primary Examiner* — Peter Paras, Jr.
*Assistant Examiner* — Briana N Ebbinghaus
(74) *Attorney, Agent, or Firm* — Viksnins Harris Padys Malen LLP

(57) ABSTRACT

Certain embodiments provide a method of producing a population of induced multipotent placental cells, the method comprising culturing a population of pluripotent stem cells in the presence of an induction media comprising a retinoid, and optionally a Wnt signaling agonist. Certain embodiments also provide cells, compositions, kits and methods of use thereof.

13 Claims, 24 Drawing Sheets
(23 of 24 Drawing Sheet(s) Filed in Color)

(56) References Cited

OTHER PUBLICATIONS

Knofler, M. , et al., “Human placenta and trophoblast development: key molecular mechanisms and model systems”, Cellular and Molecular Life Sciences 76, 3479-3496, doi: 10.1007/s00018-019-03104-6 (2019).
Knofler, M , et al., “Human placental trophoblast invasion and differentiation: a particular focus on Wnt signaling”, Front Genet 4 (190), 1-14 (2013).
Latos, P , “From the stem of the placental tree: trophoblast stem cells and their progeny”, Development (Cambridge), Company of Biologists Ltd., 3650-3660, doi:10.1242/dev.133462 (2016).
Lee, C. , et al., “What Is Trophoblast? A Combination of Criteria Define Human First-Trimester Trophoblast”, Stem Cell Reports 6(2), 257-272 (2016).
Lemke, K. , et al., “Retinoic Acid-Induced Derivation of Trophectoderm from Human Induced Pluripotent Stem Cells”, BMES Annual Meeting, Orlando, FL, Abstract and Presentation, 15 pages, (Oct. 2021).
Li, Z, et al., “Establishment of human trophoblast stem cells from human induced pluripotent stem cell-derived cystic cells under micromesh culture”, Stem Cell Res Ther 10 (1), 245, 14 pages (2019).
Mischler, A , et al., “Two distinct trophectoderm lineage stem cells from human pluripotent stem cells”, J Biol Chem 296, 100386, 17 pages (2021).
Mondal, D. , et al., “Retinoic Acid Embryopathy”, Int J Appl Basic Med Res 7(4), 264-265 (2017).
Okae, H , et al., “Derivation of Human Trophoblast Stem Cells”, Cell Stem Cell 22 (1), 50-63 (2017).
Pogozhykh, O , et al., “Placenta and Placental Derivatives in Regenerative Therapies: Experimental Studies, History, and Prospects”, Stem Cells Int 2018 (4837930, 14 pages (2018).
Rossant, J , “Culturing Trophoblast Stem (TS) Cell Lines”, CSH Protoc 2006 (2), pdb.prot4406. doi: 10.1101/pdb.prot4406 (2006).
Schmidt, J , et al., “Placenta-derived macaque trophoblast stem cells: differentiation to syncytiotrophoblasts and extravillous trophoblasts reveals phenotypic reprogramming”, Sci Rep 10, 19159, 22 pages (2020).
Sherwood, R , et al., “Wnt signaling specifies and patterns intestinal endoderm”, Mech Dev 128, 387-400 (2011).
Soncin, F. , et al., “Derivation of functional trophoblast stem cells from primed human pluripotent stem cells”, Stem Cell Reports 17(6), 1303-1317 (2022).
Spiegler, E. , et al., “Maternal-fetal transfer and metabolism of vitamin A and its precursor β-carotene in the developing tissues”, Biochim Biophys Acta 1821 (1), 88-98 (2012).
Theunissen, T. , et al., “Systematic Identification of Culture Conditions for Induction and Maintenance of Naive Human Pluripotency”, Cell Stem Cell 15, 471-487 (2014).
Wobus, A. , et al., “Retinoic acid accelerates embryonic stem cell-derived cardiac differentiation and enhances development of ventricular cardiomyocytes”, J Mol Cell Cardiol 29(6), 1525-1539 (1997).
Xu, R. , et al., “BMP4 initiates human embryonic stem cell differentiation to trophoblast”, Nature Biotechnology 20(12), 1261-1264, doi:10.1038/nbt761 (2002).
Yamashita, M. , et al., “Inhibition of transforming growth factor beta signaling pathway promotes differentiation of human induced pluripotent stem cell-derived brain microvascular endothelial-like cells”, Fluids and Barriers of the CNS 17(36), 1-12 (2020).
Yan, J , et al., “Retinoic Acid Promotes Differentiation of Trophoblast Stem Cells to a Giant Cell Fate”, Developmental Biology 235 (2), 422-432 (2001).
Cheng, T., et al., “CHIR99021 combined with retinoic acid promotes the differentiation of primordial germ cells from human embryonic stem cells”, Oncotarget 8 (5), 7814-7826 (2017).
Lemke, K , et al., “Rapid retinoic acid-induced trophoblast cell model from human induced pluripotent stem cells”, Scientific Reports 14, 18204, 1-15 (2024).
Fadloun, et al., “Retinoic acid induces TGFb-dependent autocrine fibroblast growth”, Oncogene 27, 477-489 (2008).
Han, et al., “All-trans-retinoic Acid Increases Transforming Growth Factor-b2 and Insulin-like Growth Factor Binding Protein-3 Expression through a Retinoic Acid Receptor-a-dependent Signaling Pathway”, Journal of Biological Chemistry 272 (21), 13711-13716 (1997).
Xu, et al., “Retinoid and TGF-B Families: Crosstalk in Development, Neoplasia, Immunity, and Tissue Repair”, Semin Nephrol 32, 287-294 (2012).
Zhang, et al., “All-trans retinoic acid stimulates the secretion of TGF-β2 via the phospholipase C but not the adenylyl cyclase signaling pathway in retinal pigment epithelium cells”, BMC Ophthalmology 19 (23), 6 pages (2019).
Duester, “Retinoic Acid Synthesis and Signaling during Early Organogenesis”, Cell 134, 921-931 (2008).
Metallo, et al., “Human Embryonic Stem Cell-Derived Keratinocytes Exhibit an Epidermal Transcription Program and Undergo Epithelial Morphogenesis in Engineered Tissue Constructs”, Tissue Engineering: Part A 16, 213-223 (2010).
Rönn, et al., “Retinoic Acid Regulates Hematopoietic Development from Human Pluripotent Stem Cells”, Stem Cell Reports 4, 269-281 (2015).
Tonge, et al., “Retinoic acid directs neuronal differentiation of human pluripotent stem cell lines in a non-cell-autonomous manner”, Differentiation 80, 20-30 (2010).

* cited by examiner

16/24

COMPOSITIONS AND METHODS FOR PRODUCING PLACENTAL CELLS

CROSS-REFERENCE TO RELATED APPLICATION

This application claims priority to U.S. Provisional Application No. 63/245,531 that was filed on Sep. 17, 2021. The entire content of the application referenced above is hereby incorporated by reference herein.

GOVERNMENT FUNDING

This invention was made with government support under DK114453 and GM136309 awarded by the National Institutes of Health. The government has certain rights in the invention.

This invention was made with government support under DGE-1839286 awarded by the National Science Foundation. The government has certain rights in the invention.

BACKGROUND OF THE INVENTION

The human placenta is a vital, transient organ responsible for mechanical attachment and nutrient exchange between the mother and the developing fetus. Following embryo implantation, trophectoderm cells segregate from inner cell mass (ICM) cells and then give rise to the cytotrophoblast cells (CTB) which comprise the placenta. In humans, the CTB gives rise to two types of specialized placental cells: hormone-secreting multinucleated syncytiotrophoblast cells (STBs) and invasive extravillous trophoblast cells (EVTs) (Latos, P. A. and Hemberger, M. (2016), Development (Cambridge). Company of Biologists Ltd, pp. 3650-3660. doi: 10.1242/dev.133462). Though little is known about how this cascade of events unfolds in early human embryos, complications with placentation are thought to underpin the mechanisms involved in preeclampsia, intrauterine growth restriction, and miscarriages (Knöfler, M. et al. (2019), Cellular and Molecular Life Sciences. Birkhauser Verlag AG, pp. 3479-3496. doi: 10.1007/s00018-019-03104-6). For this reason, it has been of significant interest to better understand how the human placenta is initially formed.

Current models of early human placenta include primary cells, murine trophoblast cells, and stem cell-derived trophoblast cells, but these models have drawbacks. Proliferative trophoblast cells are generally restricted to first trimester placental tissue as second and third trimester placentas contain few CTBs (Horii et al., 2016). However, trophoblast cells extracted from first trimester placental tissue do not survive long in vitro as they readily lose their proliferative capacity and differentiate (Latos, P. A. and Hemberger, M. (2016), Development (Cambridge). Company of Biologists Ltd, pp. 3650-3660. doi: 10.1242/dev.133462; Horii, M. et al. (2019), Current Protocols in Stem Cell Biology. Blackwell Publishing Inc., 50(1). doi: 10.1002/cpsc.96). Furthermore, acquisition of first trimester human placental tissue remains challenging given the ethical and regulatory barriers protecting early gestation. Though similar to human, murine placental tissue contains an extended number of subtype populations, and most importantly, murine development deviates from human development rendering murine models inadequate for understanding early cell fate decisions in human cells (Blakeley, P. et al. (2015), 142, p. 3613. doi: 10.1242/dev.131235; Latos, P. A. and Hemberger, M. (2016), Development (Cambridge). Company of Biologists Ltd, pp. 3650-3660. doi: 10.1242/dev.133462; Knöfler, M. et al. (2019), Cellular and Molecular Life Sciences. Birkhauser Verlag AG, pp. 3479-3496. doi: 10.1007/s00018-019-03104-6). Shortcomings in these two models have led researchers to explore alternative approaches, including human pluripotent stem cells (hPSCs) (e.g., human embryonic stem cells (hESCs)). Most commonly, hPSCs treated with BMP4 have been used as a trophoblast cell model as these cells acquire many trophoblast cell features, including Keratin 7 (KRT7) protein expression and secretion of human chorionic gonadotropin (hCG) (Xu, R. H. et al. (2002), Nature Biotechnology, 20(12), pp. 1261-1264. doi: 10.1038/nbt761; Horii, M. et al. (2019), Current Protocols in Stem Cell Biology. Blackwell Publishing Inc., 50(1). doi: 10.1002/cpsc.96). The validity of BMP4-induced models in recapitulating human trophoblast cells is controversial, prompting experts to define a set of criteria—hypomethylation of the ELF5 promoter region, which can be indirectly evaluated via examination of ELF5 expression; C19MC miRNA expression; KRT7, TFAP2C, and GATA3 expression; and HLA-G expression—for a high fidelity trophoblast cell model (Lee, C. Q. E. et al. (2016), Stem Cell Reports. Cell Press, 6(2), pp. 257-272. doi: 10.1016/j.stemcr.2016.01.006).

More recently, some researchers have explored using BMP4 on a naïve hPSC population, hypothesizing that BMP-4 treatment on these naïve stem cells may improve differentiation to trophectoderm since naïve stem cells may possess a greater potential for trophectoderm differentiation when compared to primed stem cells (Dong, C. et al. (2020), eLife, 9, pp. 1-26. doi: 10.7554/eLife.52504). Traditional stem cell lines are considered primed hPSCs since they are derived from epiblast cells, which are thought to be incapable of generating extra-embryonic tissue. By modulating culture conditions, it is possible to transition primed hPSCs to naïve hPSCs which may have a greater ability to generate into trophectoderm (Theunissen et al., 2014). Though expression of various trophoblast cell markers was improved when compared to methods using primed hPSCs, it can take weeks to obtain a relevant, functional population of naïve hPSC-derived trophoblast cells using this method (Dong et al., 2020). There has been further improvement of BMP-4-induced approaches by generating primed hPSC-derived trophoblast cells that proliferate and differentiate called human trophectoderm stem cells (hTESCs) (Mischler et al., 2021). However, this method involves precise control of multiple interacting growth factors and small molecules which could be complicated to implement and cost-prohibitive at scale.

Thus, there is a need for new methods and compositions for obtaining placental cells, such as trophectoderm cells, or progeny thereof.

SUMMARY OF THE INVENTION

Certain embodiments provide a method of producing a population of induced multipotent placental cells, the method comprising culturing a population of pluripotent stem cells in the presence of an induction media comprising a retinoid, and optionally a Wnt signaling agonist, under conditions suitable to produce the population of induced multipotent placental cells.

Certain embodiments provide a population of induced multipotent placental cells produced by a method as described herein. In certain embodiments, the population of cells are produced using a method as described in Example 1, wherein the cells are exposed to RA+CHIR for 3, 4 or 5 days.

Certain embodiments provide a method of producing a population of syncytiotrophoblast (STB)-like cells comprising culturing a population of induced multipotent placental cells as described herein under conditions suitable to produce a population of STB-like cells.

Certain embodiments provide a method of producing a population of extravillous trophoblast (EVT)-like cells comprising culturing the population of induced multipotent placental cells as described herein under conditions suitable to produce a population of EVT-like cells.

Certain embodiments provide a population of syncytiotrophoblast (STB)-like cells produced by a method as described herein. In certain embodiments, the population of cells are produced using a method as described in Example 1.

Certain embodiments provide a population of extravillous trophoblast (EVT)-like cells produced by a method as described herein. In certain embodiments, the population of cells are produced using a method as described in Example 1.

Certain embodiments provide a composition comprising a population of induced multipotent placental cells as described herein, a population of STB-like cells as described herein or a population of EVT-like cells as described herein, and a carrier.

Certain embodiments provide a cell culture induction media comprising a retinoid and a Wnt signaling agonist.

Certain embodiments provide a cell culture comprising an induction media as described herein and a population of pluripotent stem cells.

Certain embodiments provide a kit comprising a retinoid, a Wnt signaling agonist, and instructions for preparing an induction media comprising the retinoid and the Wnt signaling agonist, and for culturing a population of pluripotent stem cells in the presence of the induction media to produce a population of induced multipotent placental cells.

Certain embodiments provide a method of identifying a test agent that is capable of modifying the structure, function or development of placental cells/tissue, the method comprising contacting a population of induced multipotent placental cells as described herein, a population of STB-like cells as described herein, or a population of EVT-like cells as described herein, or placental tissue comprising such cells, with the test agent, wherein the agent is identified as a modifier when the structure, function or development of the placental cells/tissue differs as compared to a control.

Certain embodiments provide a method comprising contacting a fertilized cell, or progeny thereof, with a population of induced multipotent placental cells as described herein, a population of STB-like cells as described herein, or a population of EVT-like cells as described herein under conditions suitable for cell growth.

Certain embodiments provide a method of treating a placental abnormality in a pregnant female mammal, the method comprising administering a population of induced multipotent placental cells as described herein, a population of STB-like cells as described herein, or a population of EVT-like cells as described herein, to the mammal.

Certain embodiments provide a population of induced multipotent placental cells as described herein, a population of STB-like cells as described herein, or a population of EVT-like cells as described herein, for use in treating a placental abnormality in a pregnant female mammal.

Certain embodiments provide the use of a population of induced multipotent placental cells as described herein, a population of STB-like cells as described herein, or a population of EVT-like cells as described herein to prepare a medicament for treating a placental abnormality in a pregnant female mammal.

Certain embodiments provide an induced multipotent placental cell as described herein, or a progeny cell thereof (e.g., a differentiated progeny cell thereof). In certain embodiments, the multipotent placental cell, or a progeny cell thereof, expresses a combination of markers as described herein (e.g., has a transcriptional signature as described herein (see, e.g., FIGS. 1I-1L; FIG. 2B-C, E; FIG. 10; FIG. 12; FIG. 14; and Tables 4-6)). For example, in certain embodiments, the multipotent placental cell expresses a marker or a combination of markers as described herein (e.g., as described in FIG. 14/Table 6 (e.g., expresses KRT7, TFAP2C and/or ABCG2)). In certain embodiments, the induced multipotent placental cell expresses CDX2 and one or more markers selected from the group consisting of Keratin 18 (KRT18), Keratin 7 (KRT7), KLF4, GATA3, E-cadherin, E74 like ETS transcription factor 5 (ELF5), one or more C19MC miRNAs, transcription factor AP-2 gamma (TFAP2C), HLA-G (HLA-G), and combinations thereof; and/or 2) the induced multipotent placental cell does not express OCT4, FoxA2, SOX17, and/or ITGB3. In certain embodiments, the level of expression of a certain marker or combination of markers described herein may vary as compared to a control cell, such as corresponding control cell (e.g., a primary cell or model cell counterpart) (see, e.g., FIG. 14 and Table 6).

Certain embodiments also provide a STB-like cell or an EVT-like cell as described herein (e.g., comprising one or more properties as described herein).

Certain embodiments provide a method as described herein useful for producing an induced multipotent placental cell as described herein, or a progeny cell thereof (e.g., a differentiated progeny cell thereof).

Certain embodiments provide methods and intermediates disclosed herein that are useful for preparing induced multipotent placental cells, or differentiated cells derived therefrom.

BRIEF DESCRIPTION OF THE FIGURES

The patent or application file contains at least one drawing executed in color. Copies of this patent or patent application publication with color drawing(s) will be provided by the Office upon request and payment of the necessary fee.

(FIG. 1A) (top) Schematic diagram of differentiation; (bottom) Immunostaining images of cells before (Day 0) and following (Day 5) RA treatment. Scale bar is 50 μm. (FIG. 1B) PCR of cells before treatment (Day 0) and cells treated for 5 days with conditions denoted above the gel. GAPDH was used as a housekeeping gene. (FIG. 1C) Flow cytometric analysis of CDX2 in cells before treatment (stem cells) or cells treated for 5 days with conditions denoted in legend. (FIG. 1D) Immunostaining images of cells treated for 5 days with unconditioned medium (UM) containing RA and CHIR. Scale bar is 50 μm. (FIG. 1E) qRT-PCR analysis during the differentiation in UM containing RA and CHIR. For each grouping, the following timepoints are shown from left to right: Day 0, Day 1, Day 2, Day 3, Day 4, and Day 5. Error bars represent SD, p-values determined based on ANOVA test with Dunnett's multiple comparisons test (p≤0.01, *p≤0.001, ****p≤0.0001). (FIG. 1F) Immunostaining images of cells following 5 days of treatment with UM containing RA and CHIR. Scale bar is 50 μm. (FIG. 1G) Flow cytometric analysis of cells along the differentiation trajectory (CDX2 and Oct-4 expression at various timepoints during differentiation). (FIG. 1H) Phase contrast images of an example differentiation of cells maintained in the indicated above media. Scale bars are all 200 μm. (FIG. 1I) Correlation heatmap of log 2, normalized, batch corrected RNA sequencing data from human primary cells (dark blue (+)), BMP4-induced cells (light blue (*)), and RA+CHIR treated cells (green (#)). Clustering was performed using Euclidean distances. (FIG. 1J) PCA of the RNA sequencing datasets. (FIG. 1K) Heatmap and dendrogram of RNA sequencing datasets clustered based on a subset of trophoblast cell associated genes. Genes are sorted based on highest expression in all samples. (FIG. 1L) qRT-PCR analysis of C19 microRNAs during the RA+CHIR differentiation; BeWo cells are included as a positive control.

(FIG. 2A) (top) Schematic diagram depicting differentiation strategy. (bottom) Immunostaining images after 5 days of UM containing RA and CHIR (Day 5, top) and day 5 subcultured cells maintained for 5 days in UM with hypoxia (EVT-like, middle) or normoxia (STB-like, bottom). Arrows indicate sites of multinucleation. Scale bar is 400 μm. (FIG. 2B) qRT-PCR analysis of cells during hypoxia treatment compared to D5 RA+CHIR. For each grouping, the following are shown from left to right: D5 RA+CHIR; D3 EVT; D4 EVT; and D5 EVT. (FIG. 2C) PCR of cells treated in hypoxia for 2-, 3-, 4-, or 5-days vs cells treated in normoxic conditions for 5 days. (FIG. 2D) hCG media concentration determined by ELISA in cells treated in normoxia for 1-5 days. Error bars indicate SD of two technical replicates. (FIG. 2E) PCR of cells maintained in hypoxia for 1, 2, 3, 4, or 5 days.

(FIG. 5A) Immunostaining images of Keratin 8 and CDX2 after 5 days incubation with above labelled media composition. (FIG. 5B) RT-PCR of mRNA isolated from stem cells (iPSCs) after 5-day incubation with the labelled media condition (SU: SU6656). Scale bar is 200 μm.

(FIG. 6A) Immunostaining images of CDX2 expression of cells seeded at indicated initial seeding density and maintained for 5 days in UM+1 μM RA. (FIG. 6B) Flow cytometry CDX2 histogram at Day 3 or 5 of differentiation in UM+1 μM RA+8 μM CHIR for indicated initial seeding density. Scale bar is 200 μm.

(FIG. 7A) Flow cytometry histogram of GATA3 expression from undifferentiated stem cells, cells differentiated for 5 days in E6+RA+CHIR, and cells differentiated for 5 days in UM+RA+CHIR (top). Flow cytometry histogram of Keratin 7 expression from cells differentiated for 5 days in E6+RA+CHIR and cells differentiated for 5 days in UM+RA+CHIR (bottom). (FIG. 7B) Immunostaining images of CDX2 expression after 5 days incubation with the indicated media composition. Scale bar is 200 μm.

(FIG. 12A) PCA of transcript level data from primary human embryo cells (epiblast: EPI.D6-D12, primitive endoderm: PE.D6-D12, trophectoderm: TE.D6-D14) and cells treated with RA+CHIR (RA+CHIR.D0-D5). Arrows were added for clarity and do not indicate known trajectory. (FIG. 12B) PCA of transcript level data from primary human trophectoderm cells (TE.D6-D14), RA+CHIR treated cells (RA+CHIR.D0-D5), and two alternative BMP-4-directed differentiations (GSE137295: hTSCs, and hTESCs; GSE138688: naïve_TSCs, and primed_TSCs). Shaded regions indicate distinct k-means clusters. (FIG. 12C) Spearman correlation heatmap of log 2, normalized, batch corrected RNA sequencing data from human primary trophectoderm cells, BMP-4-induced cells, and RA+CHIR treated cells. (FIGS. 12D,E) Transcripts per million (TPM) expression of ELF5 (FIG. 12D) and TFAP2C (FIG. 12E) in RNA-sequencing samples. Data are presented as boxplots with biological replicates shown where applicable.

DETAILED DESCRIPTION

Figure 1A:
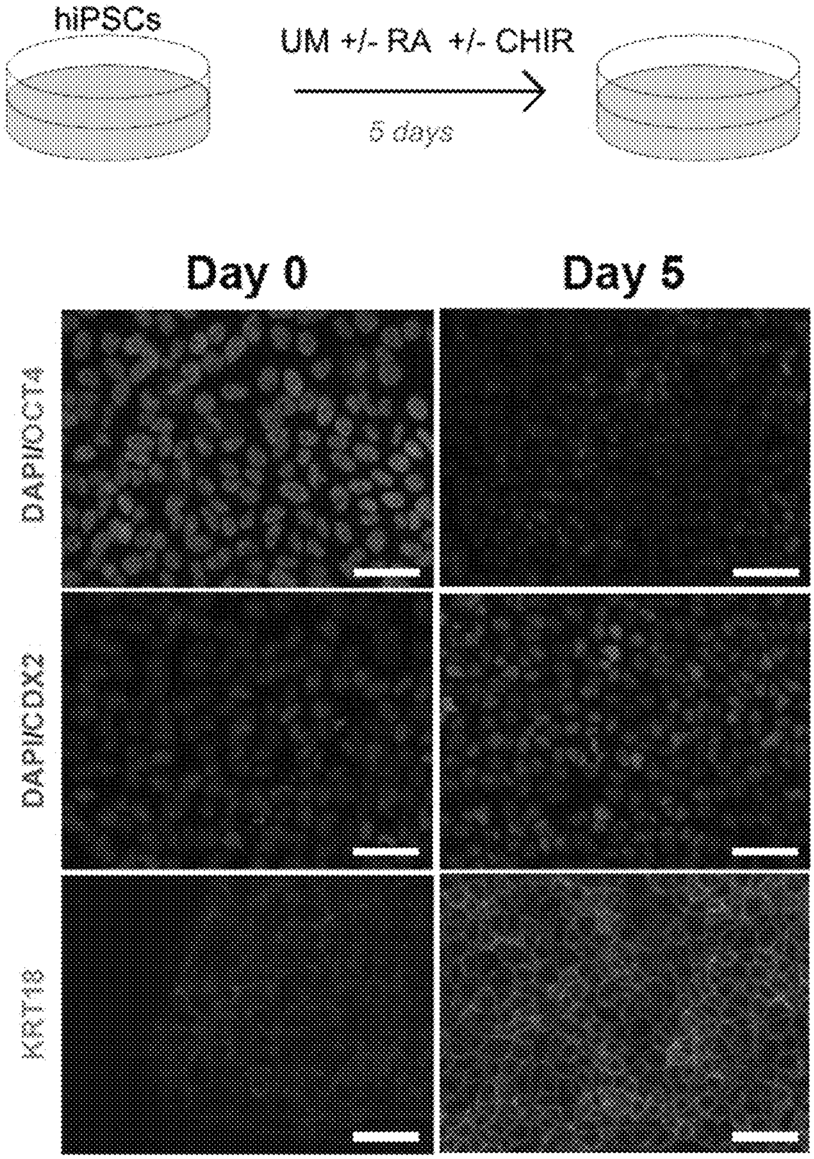
FIGS. 1A-1L. Treatment with retinoic acid (RA; also referred herein as tretinoin)) and CHIR-99021 (CHIR; 6-[[2-[[4-(2,4-Dichlorophenyl)-5-(5-methyl-1H-imidazol-2-yl)-2-pyrimidinyl]amino]ethyl]amino]-3-pyridinecarbonitrile) results in upregulation of trophoblast cell markers, and cells are similar to early human primary trophectoderm.

There are a limited number of accessible and representative models of human trophoblast cells useful for disease modeling and understanding of placentation. Stem cell models currently implemented require a transition through a naïve stem cell fate (e.g., which can take weeks) or precise dynamic control of multiple interacting growth factor (protein) and small molecule cues.

As described herein, an alternative method for the generation of placental tissue has been developed, which involves exposing pluripotent stem cells (e.g., human induced pluripotent stem cells (hiPSCs)) to a retinoid (e.g., retinoic acid (RA)), and optionally, a Wnt signaling agonist (e.g., CHIR-99021). In particular, it was shown in the Examples that exposure of hiPSCs to RA and the Wnt signaling agonist CHIR-99021 resulted in rapid, synergistic upregulation of CDX2, an important transcription factor for trophectoderm induction and maintenance of the trophoblast cell population. Analysis of the transcriptional profile of these cells showed high similarity with primary trophectoderm cells, and these cells can also be further differentiated into cells with features of placental subtype cells, including syncytiotrophoblast (STB)- and extravillous trophoblast (EVT)-like cells. The method is rapid and robust, producing a homogenous population within eight days of cell seeding and functional placental cells within 13 days of seeding without having to transition to a naïve stem cell fate. This is in contrast with certain other previously reported methods that initially take more than 50 days to generate placental tissue, require extensive experimental steps to generate various intermediate cell fates prior to generation of placental cells, and/or involve precise control of multiple interacting growth factors and small molecules. Taken together, the data described herein demonstrate the development of a simple method for the generation of multipotent placental cells (trophoblast-like cells), which are transcriptionally similar to primary cells.

The cells produced using a method or composition described herein may be used for a variety of applications, including but not limited to, developing a better understanding of mechanisms and interactions involving the placenta, such as elucidating early cell fate decisions, understanding how various pregnancy complications from placental abnormalities arise (e.g., using the cells to screen for risk factors), studying the mother-placenta-fetus transport properties (e.g., to better understand drug interactions or bacterial infections), cell therapy in women who are at a high risk for pregnancy, and enhancing the success of an IVF procedure.

The following definitions are used, unless otherwise described: Alkyl, alkoxy, alkenyl, etc. denote both straight and branched groups; but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples include $(C_1$-$C_8)$alkyl, $(C_2$-$C_8)$alkyl, $(C_1$-$C_6)$alkyl, $(C_2$-$C_6)$alkyl and $(C_3$-$C_6)$alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and and higher homologs and isomers.

The term "alkenyl" refers to an unsaturated alkyl radical having one or more double bonds. Examples of such unsaturated alkyl groups include vinyl, 2-propenyl, crotyl, 2-isopentenyl, 2-(butadienyl), 2,4-pentadienyl, 3-(1,4-pentadienyl) and the higher homologs and isomers.

The term "alkoxy" refers to an alkyl group attached to the remainder of the molecule via an oxygen atom ("oxy").

The term "cycloalkyl" refers to a saturated or partially unsaturated (non-aromatic) all carbon ring having 3 to 8 carbon atoms (i.e., $(C_3$-$C_8)$carbocycle). The term also includes multiple condensed, saturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 3 to 15 carbon atoms, about 6 to 15 carbon atoms, or 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). Non-limiting examples of cycloalkyls include cyclopropyl, cyclobutyl, cyclopentyl, cyclohexyl, bicyclo[2.2.1]heptane, pinane, and adamantane.

The term "cycloalkyloxy" refers to a cycloalkyl group attached to the remainder of the molecule via an oxygen atom ("oxy").

The term "alkoxycarbonyl" as used herein refers to a group (alkyl)-O—C(═O)—, wherein the term alkyl has the meaning defined herein.

The compounds disclosed herein may exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —$CH_3$ group may be substituted with —$CD_3$.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

A bond designated  herein represents a double bond that can optionally be cis, trans, or a mixture thereof.

Salts of certain compounds described herein may be used. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Methods for Producing Induced Multipotent Placental Cells, and Progeny and Compositions Thereof Accordingly, certain embodiments provide a method of producing a population of induced multipotent placental cells, the method comprising culturing a population of pluripotent stem cells in the presence of an induction media comprising a retinoid, under conditions suitable to produce the population of induced multipotent placental cells.

The term "retinoid" includes any Generation I, II, III, or IV retinoid compound that is capable of activating the retinoic acid signaling pathway. Retinoids regulate gene expression by interaction with nuclear receptors; a more detailed description of the signaling pathway can be found in this non-limiting reference, which is incorporated herein by reference in its entirety for all purposes (Cunningham, T. J., & Duester, G. (2015). Mechanisms of retinoic acid signalling and its roles in organ and limb development. *Nature Publishing Group*. doi.org/10.1038/nrm3932). Generation I retinoids include retinol, retinal, tretinoin (retinoic acid), isotretinoin, and alitretinoin; generation II retinoids include etretinate and acitretin; generation III retinoids include adapalene, bexarotene, and tazarotene; and generation IV retinoids include Trifarotene. In one embodiment, the retinoid comprises a cyclic end group, a polyene side chain and a polar end group.

In one embodiment, the retinoid is a compound of formula I:

(I)

wherein:

- ring A is phenyl or cyclohexen-1-yl, which phenyl or cyclohexen-1-yl is optionally substituted with one or more groups independently selected from $(C_1\text{-}C_8)$alkyl, $(C_3\text{-}C_{10})$cycloalkyl, $(C_1\text{-}C_8)$alkoxy, and $(C_3\text{-}C_8)$cycloalkyloxy; and
- $R^1$ is $(C_5\text{-}C_{20})$alkenyl that is substituted with one or more groups independently selected from hydroxy, carboxy, or $(C_1\text{-}C_6)$alkoxycarbonyl;
- or a salt thereof (e.g., a pharmaceutically acceptable salt thereof).

In one embodiment, the retinoid is a compound of formula (Ia):

(Ia)

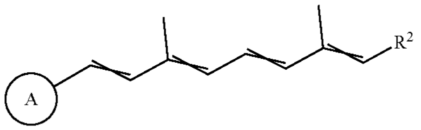

wherein:

$R^2$ is hydroxymethyl, carboxy, or $(C_1\text{-}C_6)$alkoxycarbonyl; or a salt thereof (e.g., pharmaceutically acceptable salt thereof).

In one embodiment, the retinoid is a compound of formula (Ib):

(Ib)

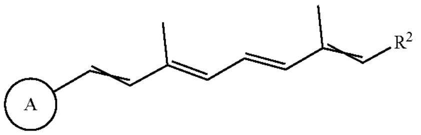

wherein:

$R^2$ is hydroxymethyl, carboxy, or $(C_1\text{-}C_6)$alkoxycarbonyl; or a salt thereof (e.g., a pharmaceutically acceptable salt thereof).

In one embodiment, the retinoid is a compound of formula (Ic):

(Ic)

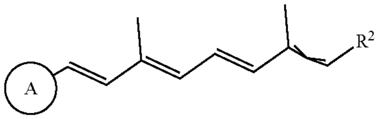

wherein:

$R^2$ is hydroxymethyl, carboxy, or $(C_1\text{-}C_6)$alkoxycarbonyl; or a salt thereof (e.g., a pharmaceutically acceptable salt thereof).

In one embodiment, the retinoid is a compound of formula (Id):

(Id)

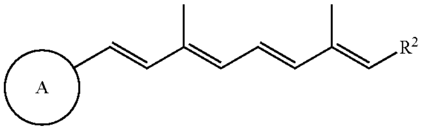

wherein:

$R^2$ is hydroxymethyl, carboxy, or $(C_1\text{-}C_6)$alkoxycarbonyl; or a salt thereof (e.g., a pharmaceutically acceptable salt thereof).

In one embodiment, the retinoid is a compound of formula (Ie):

(Ie)

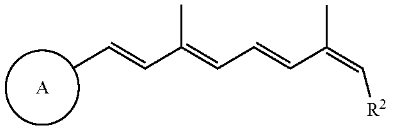

wherein:

$R^2$ is hydroxymethyl, carboxy, or $(C_1\text{-}C_6)$alkoxycarbonyl; or a salt thereof (e.g., a pharmaceutically acceptable salt thereof).

In one embodiment, ring A is selected from the group consisting of:

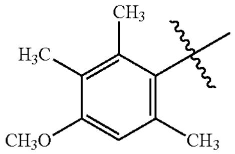

and

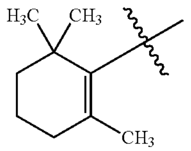

.

In one embodiment, the retinoid is retinol, tretinoin, isotretinoin, alitretinoin, acitretin, adapalene, bexarotine, or tazarotene or a salt thereof (e.g., a pharmaceutically acceptable salt thereof).

In one embodiment, the retinoid is retinoic acid (tretinoin):

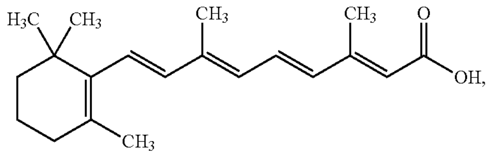

Retinoic acid (Tretinoin)

or a salt thereof (e.g., a pharmaceutically acceptable salt thereof).

As described herein, the combination of a retinoid and a Wnt signaling agonist was shown to result in the rapid, synergistic upregulation of CDX2, an important transcription factor for trophectoderm maintenance (see, the Examples). Thus, in certain embodiments, the method further comprises culturing a population of pluripotent stem cells in the presence of an induction media comprising a retinoid and a Wnt signaling agonist.

The term "Wnt signaling agonist" includes any compound/molecule that is capable of activating the Wnt signaling pathway (see, e.g., Archbold, H. C., Yang, Y. X., Chen, L., & Cadigan, K. M. (2012). How do they do Wnt they do?: Regulation of transcription by the Wnt/β-catenin pathway. *Acta Physiologica,* 204(1), 74-109. doi.org/10.1111/j.1748-1716.2011.02293.x; and Clevers, H. (2006). Wnt/β-Catenin Signaling in Development and Disease. *Cell,* 127(3), 469-480. doi.org/10.1016/J.CELL.2006.10.018, which are incorporated herein by reference in their entirety for all purposes). Wnt signaling agonists include, but are not limited to, Wnt ligands, such as Wnt3a; the R-spondin family of proteins, BIO; SB216763; and CHIR-99021.

In certain embodiments, the Wnt signaling agonist is selected from the group consisting of:

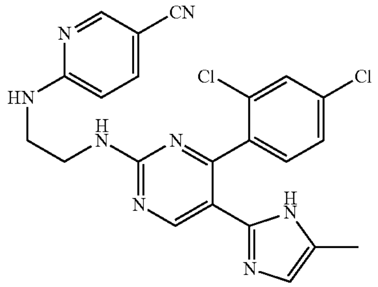

CHIR-99021

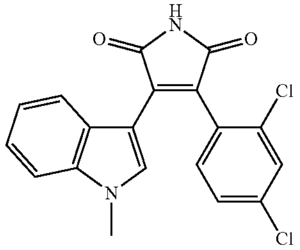

SB216763 and

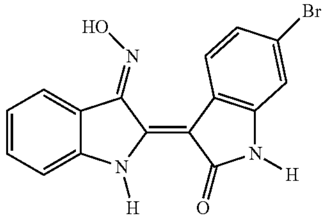

BIO and salts thereof (e.g., pharmaceutically acceptable salts thereof).

In certain embodiments, the Wnt signaling agonist is CHIR-99021, or a salt thereof.

In certain embodiments, the retinoid is retinoic acid (tretinoin), or a salt thereof, and the Wnt signaling agonist is CHIR-99021, or a salt thereof.

Figure 1I:
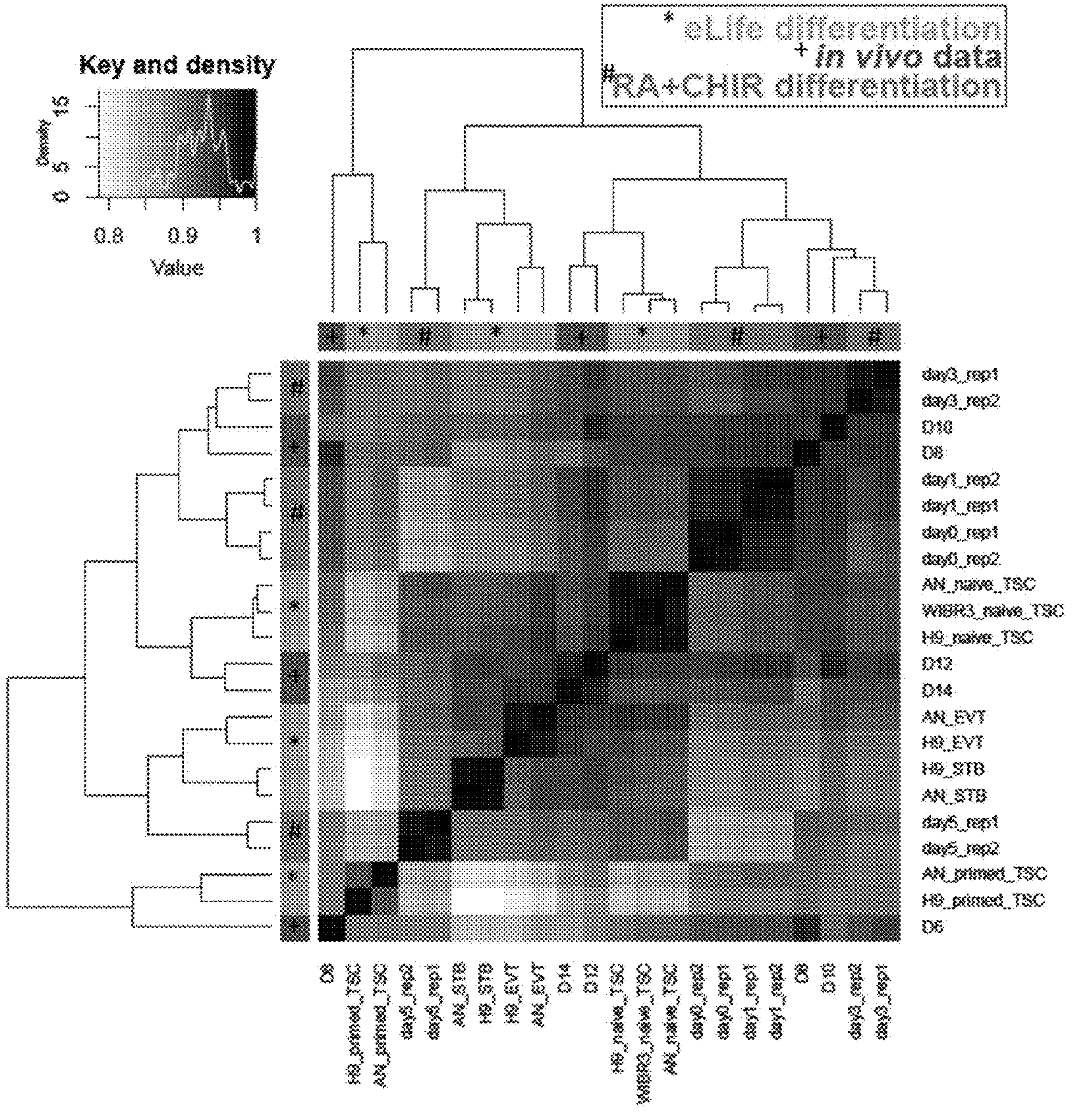
Figure 1J:
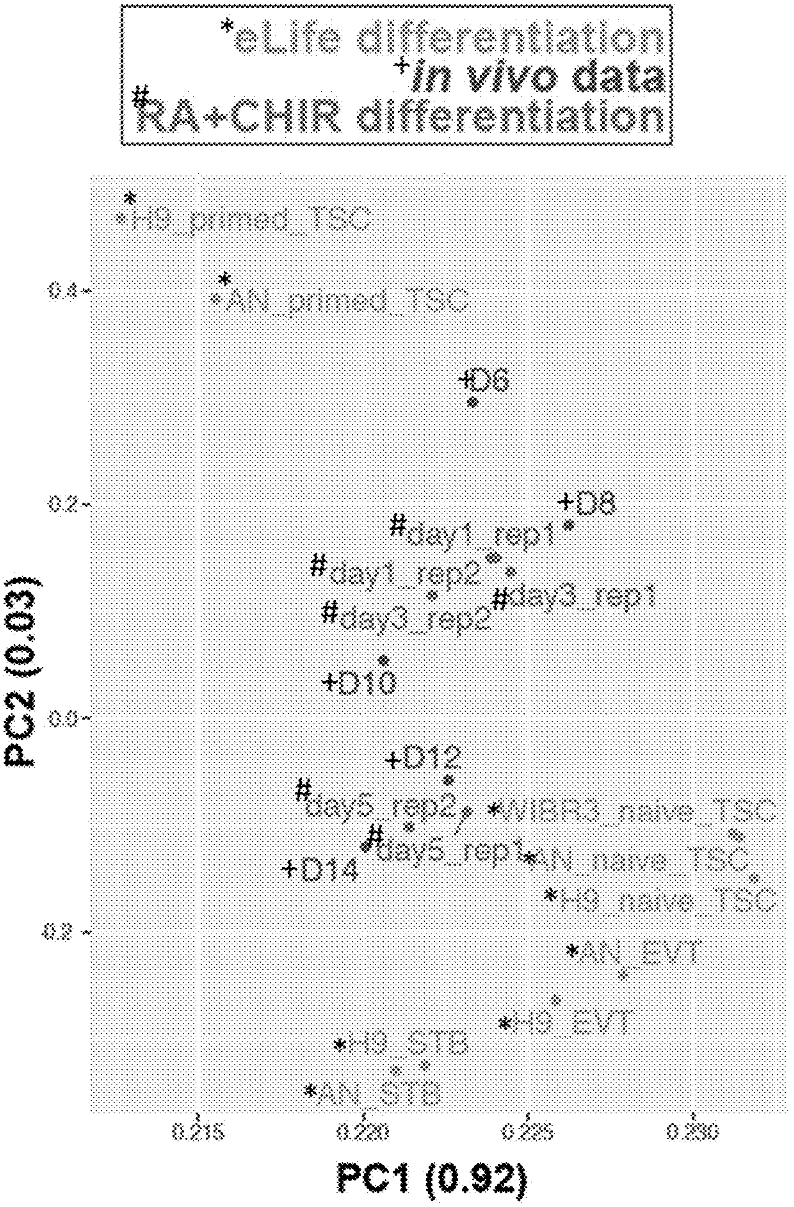
Figure 1K:
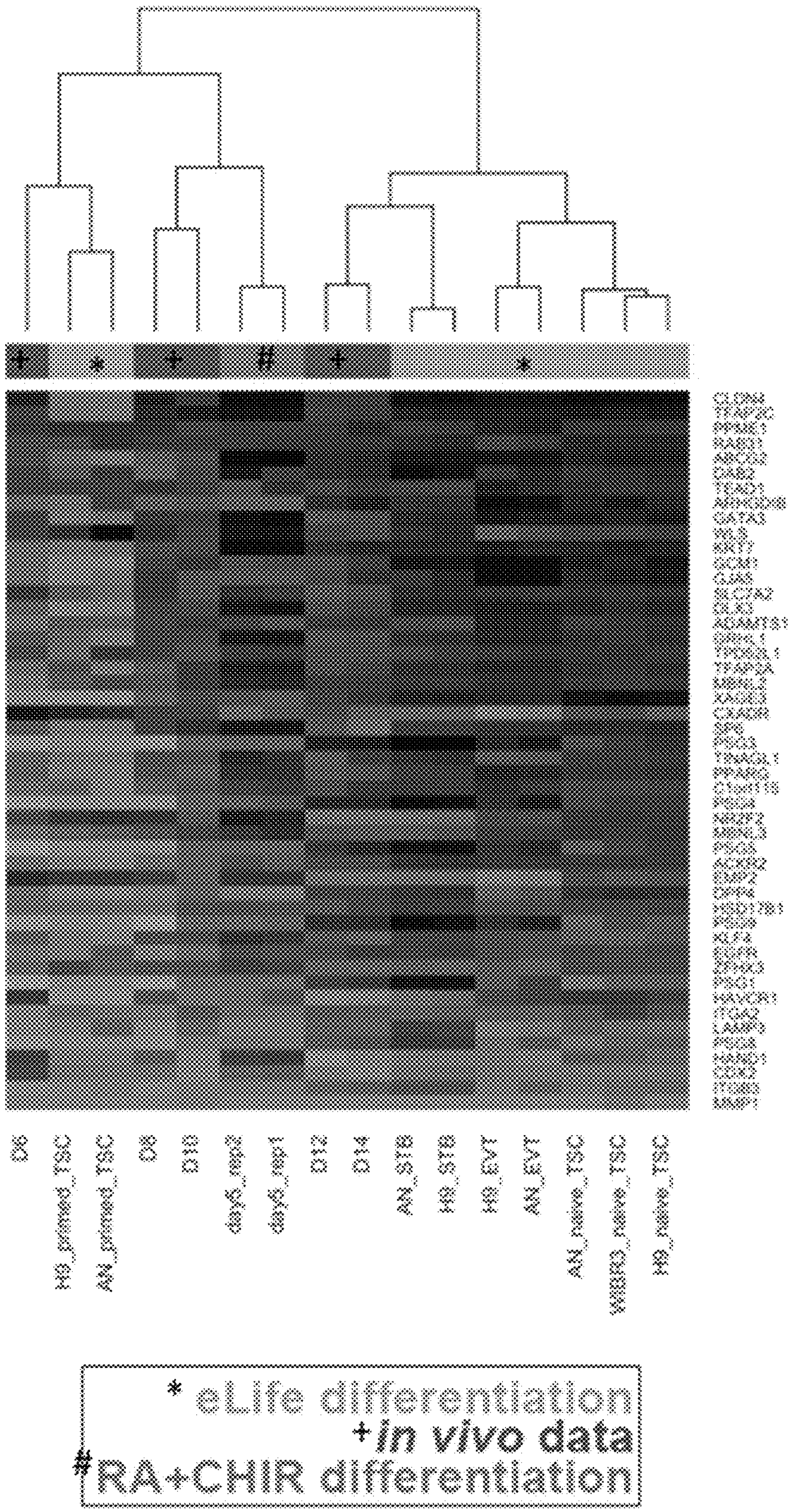
Figure 1L:
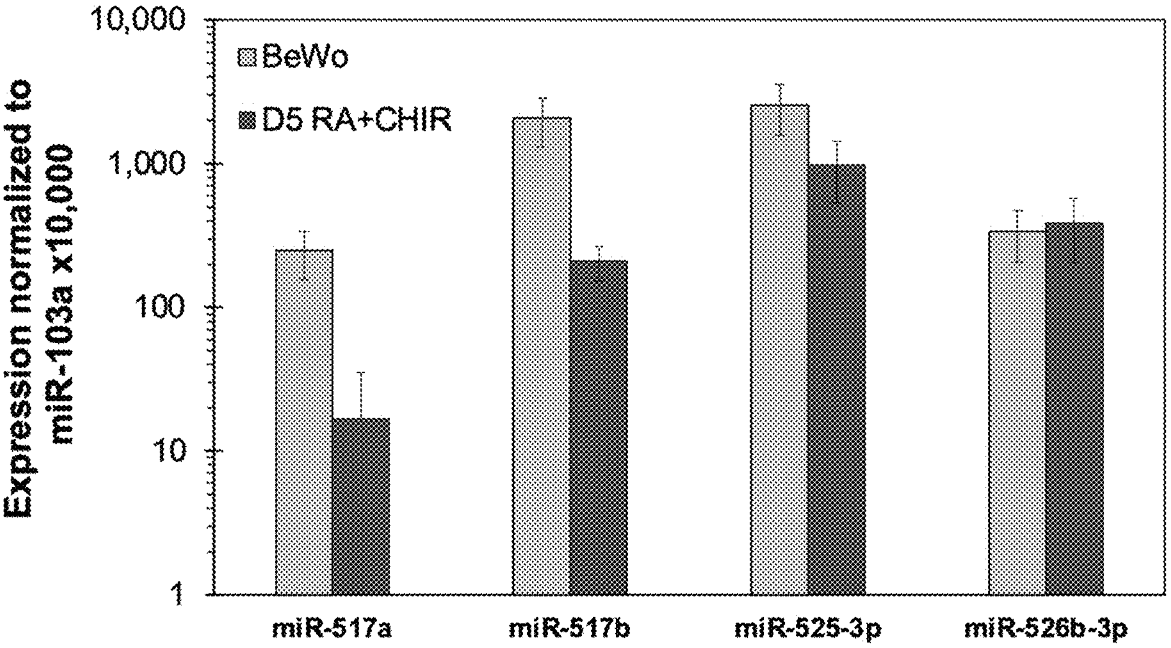
Figure 2A:
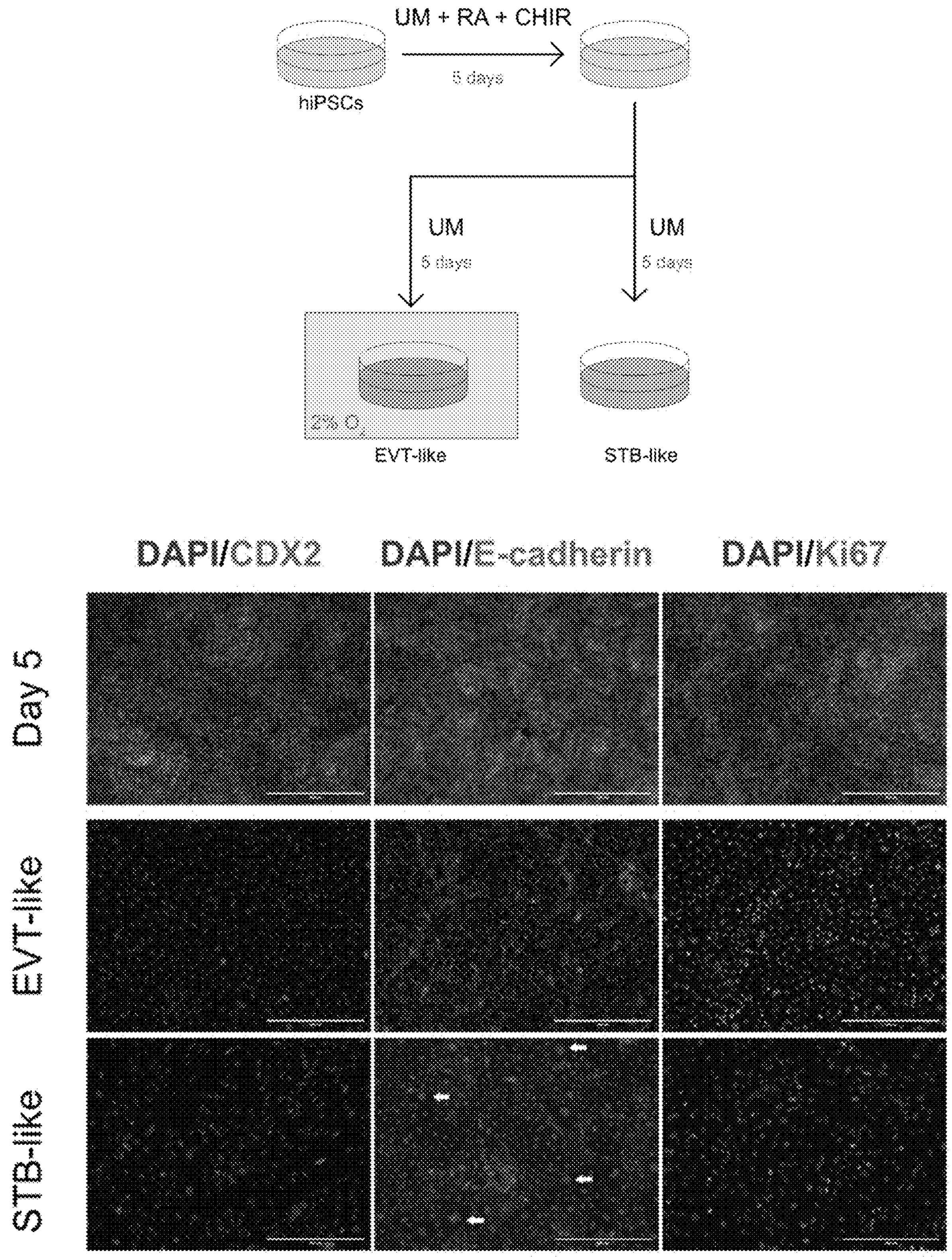
FIGS. 2A-2E. RA and CHIR treated cells show functional phenotypes following subculture.
Figure 2B:
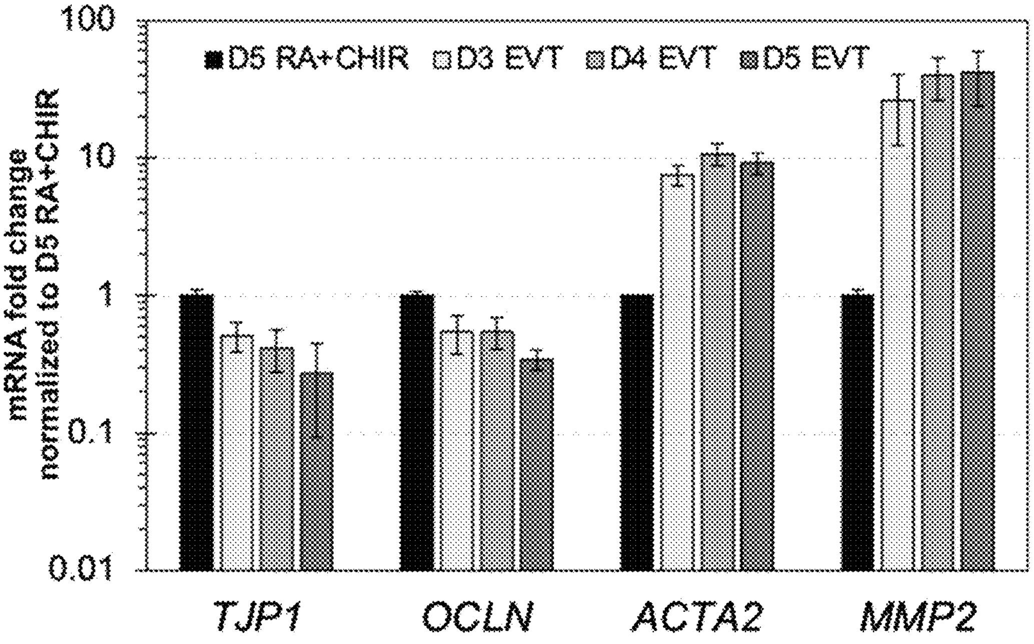
Figure 10:
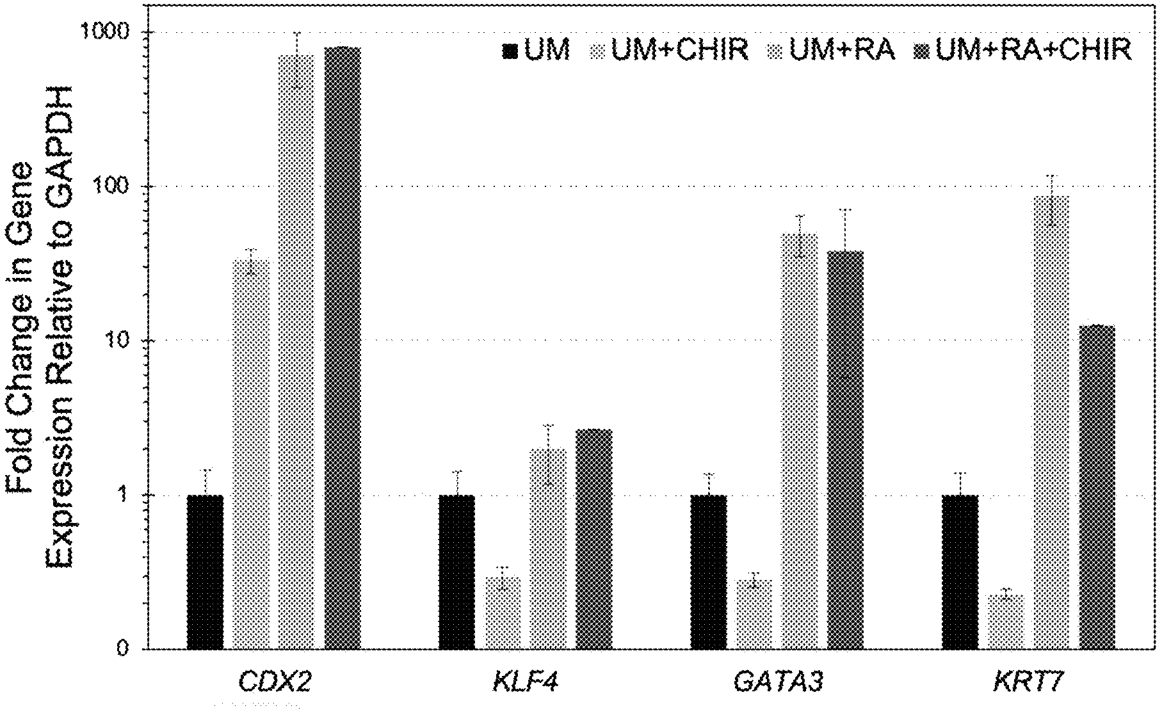
FIG. 10. Day 5 expression of trophoblast cell markers based on induction media composition. qRT-PCR analysis of mRNA isolated from cells maintained for 5 days in the induction media indicated in the legend. For each grouping, the following are shown from left to right: UM; UM+CHIR; UM+RA; and UM+RA+CHIR. Error bars are SD of technical replicates.
Figure 14:
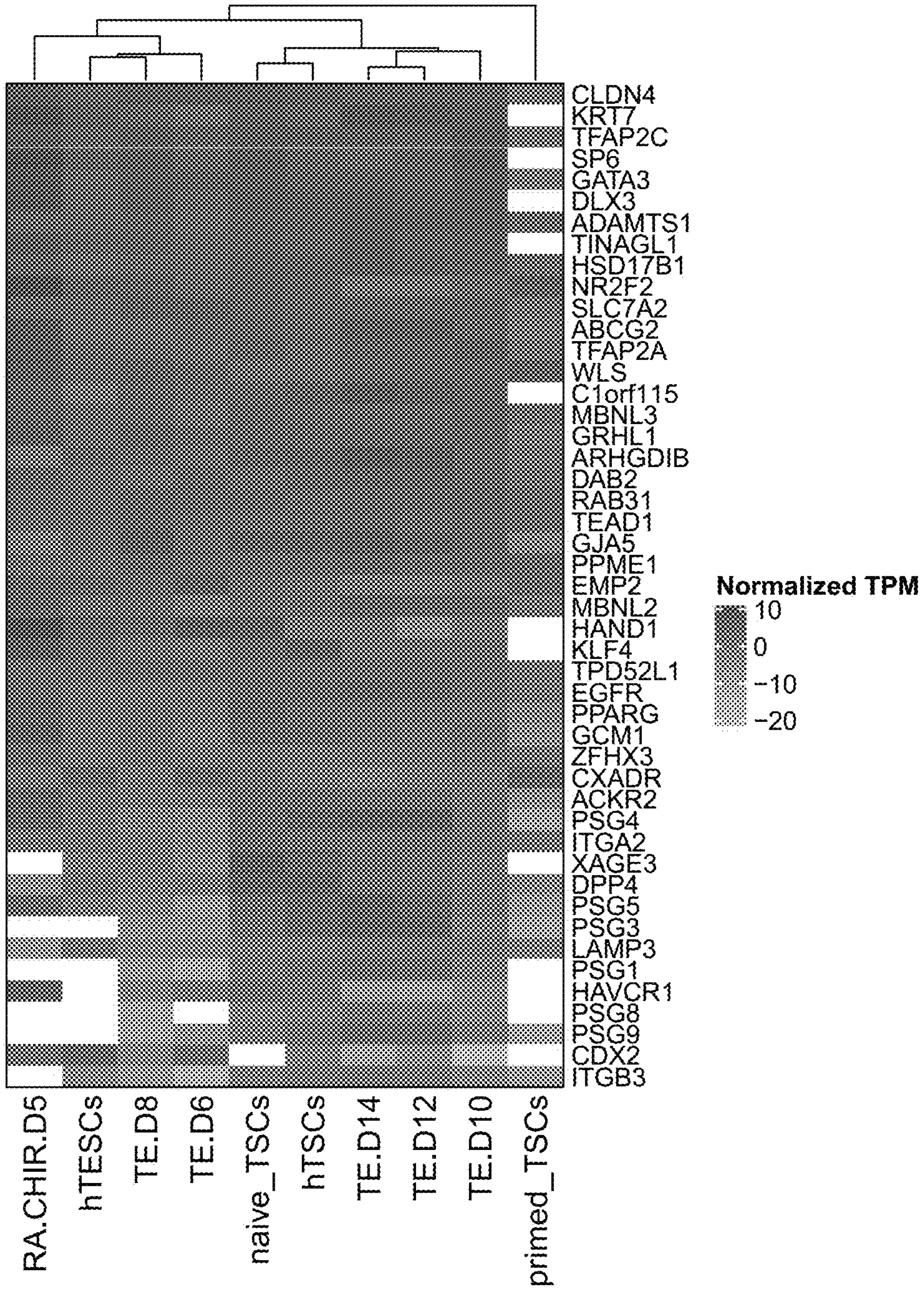
FIG. 14. RA+CHIR-treated cells have a trophectoderm-specific transcriptome most similar to hTESCs and day 6-day 8 primary trophectoderm. Heatmap and dendrogram of trophectoderm-associated gene expression in the RNA-sequencing samples. TE (primary trophectoderm, GSE109555), naive_TSC and primed_TSC (GSE138688), hTSCs and hTESCs (GSE137295) (Dong et al., 2020; Mischler et al., 2021; Zhou et al., 2019). Unfilled boxes indicate gene was not quantifiably expressed. See also, Table 6.

Within the trophectoderm/trophoblast cell lineage, expression of defining cell markers is temporally dynamic. These cell types express CDX2, GATA3 and KRT7; however, expression of these three markers may or may not coincide. For example, CDX2 expression typically precedes the expression of GATA3 and KRT7. Thus, as used herein, the term "induced multipotent placental cell" refers to a cell produced by a method described herein, which expresses or had expressed CDX2 at the RNA and/or protein level; expresses or is capable of expressing at least one or both of GATA3 and Keratin 7 at the RNA and/or protein level; and has the capacity differentiate into multiple cell lineages. In certain embodiments, these cells have the capacity to self-renew. These cells may also possess certain epithelial cell features, including e.g., mononucleation, epithelial cadherin (E-cadherin) expression, and/or distinct cell borders (see, e.g., Example 1, FIGS. 1F and 1H). The cells are generally highly proliferative, which may be evident by expression of Ki67, a protein present in actively dividing cells. In humans, trophectoderm cells segregate from inner cell mass (ICM)

cells and then give rise to the trophoblast cells present within the placenta. These trophoblast cells can then give rise to two types of specialized placental cells: hormone-secreting multinucleated syncytiotrophoblast cells (STBs) and the invasive extravillous trophoblast cells (EVTs) (Latos, P. A. and Hemberger, M. (2016), Development (Cambridge). Company of Biologists Ltd, pp. 3650-3660. doi: 10.1242/dev.133462). The induced multipotent placental cells described herein are functionally and molecularly similar to primary multipotent placental cells (e.g., trophectoderm or trophoblast cells, such as D8-D10 primary trophectoderm). For example, the induced multipotent placental cells have the capability of differentiating into STB-like and EVT-like cells. While similar to their primary cell counterparts, the induced cells have certain distinguishing features, such a highly similar but unique transcriptional signature (see, e.g., Example 1, FIGS. 1I-1L; FIG. 2B; FIG. 10; FIG. 12; FIG. 14 and Tables 4-6). Thus, the induced multipotent placental cells of the invention may also be referred to herein as, e.g., an induced trophectoderm cell, a trophectoderm-like cell or a model trophectoderm cell; or an induced trophoblast cell, a trophoblast-like cell or a model trophoblast cell. Similar to their primary cell counterparts, the expression patterns of the induced multipotent placental cells are temporally dynamic, and at a given timepoint, the cells may express (i.e., at the RNA and/or protein level) a combination of markers of the trophectoderm or trophoblast cell lineage (see, e.g., the Examples and Figures). Thus, in certain embodiments, a multipotent placental cell expresses (i.e., at the RNA or protein level) a marker or combination of markers as described herein. In certain embodiments, a multipotent placental cell does not express (e.g., detectably express) a marker or combination of markers as described herein. In certain embodiments, such a marker or makers are described in any one of FIGS. 1I-1L; FIG. 2B; FIG. 10; FIG. 12; FIG. 14; and Tables 4-6. For example, the induced multipotent placental cells may express at a given timepoint a particular combination of trophoblast cell/trophectoderm markers (e.g., as described herein), such as a combination of markers selected from the group consisting of CDX2, Keratin 18 (KRT18), Keratin 8 (KRT8), Keratin 7 (KRT7), KLF4, GATA3, E-cadherin (CDH1), Ki67, E74 like ETS transcription factor 5 (ELF5), one or more C19MC miRNAs (e.g., 517a, 517b, 525-3p, and/or 526b-3p miRNAs), transcription factor AP-2 gamma (TFAP2C), tight junction protein 1 (TJP1), Occludin (OCLN), and HLA-G (e.g., HLA-G1/2) (HLA-G). In certain embodiments, the induced multipotent placental cells may express at a given timepoint a combination of markers selected from the group consisting of CDX2, Keratin 18 (KRT18), Keratin 7 (KRT7), KLF4, GATA3, E-cadherin (CDH1), and Ki67. In certain embodiments, the induced multipotent placental cells express CDX2 and GATA3. In certain embodiments, the induced multipotent placental cells express CDX2 and KRT7. In certain embodiments, the induced multipotent placental cells express GATA3 and KRT7. In certain embodiments, the induced multipotent placental cells express CDX2, GATA3 and KRT7. In certain embodiments, the induced multipotent placental cells express CDX2, GATA3, KRT7, transcription factor AP-2 gamma (TFAP2C), E74 like ETS transcription factor 5 (ELF5), one or more C19MC miRNA, and HLA-G. In certain embodiments, the multipotent placental cells do not express markers of other cell lineages (i.e., at the RNA or protein level), such as the cells of the endoderm lineage. For example, in certain embodiments, the multipotent placental cell does not express Oct-4, a marker for pluripotent cells, or FoxA2 and/or SOX17, markers for definitive endoderm. In certain embodiments, the induced multipotent placental cell is considered a trophoblast cell model cell based on the criteria defined by Lee, C. Q. E. et al. (2016), *Stem Cell Reports*. Cell Press, 6(2), pp. 257-272. Doi: 10.1016/j.stemcr.2016.01.006, which is incorproated by reference herein for all purposes. In certain embodiments, the induced multipotent placental cell 1) has hypomethylation of the ELF5 promoter region (e.g., expresses ELF5); 2) expresses C19MC miRNAs; 3) expresses KRT7, TFAP2C, and GATA3; and/or 4) expresses HLA-G. In certain embodiments, the induced multipotent placental cell 1) expresses ELF5; 2) expresses C19MC miRNA; 3) expresses KRT7, TFAP2C, and GATA3; and 4) expresses HLA-G. In certain embodiments, the induced multipotent placental cell expresses ABCG2.

As described above, the induced multipotent placental cells produced by a method described herein (e.g., iMPC1-D5 cells from Example 1) are similar to their primary cell counterparts, but have certain distinguishing features, such a highly similar but unique transcriptional signature (see, e.g., FIG. 14/Table 6). These cells are also similar to, but have certain distinguishing features over, certain other model cells (e.g., see, FIG. 14/Table 6; see also, FIG. 12B, wherein the D5 RA+CHIR cells fall into the same k-means cluster as the primary cells, whereas most other BMP4-derived stem cell differentiations are not included in this cluster). For example, in certain embodiments, an induced multipotent placental cell expresses a marker or a combination of markers, as described in FIG. 14 and/or Table 6 (e.g., KRT7, TFAP2C and/or ABCG2). In certain embodiments, an induced multipotent placental cell does not express (e.g., detectably express) a marker or a combination of markers, as described in FIG. 14 and/or Table 6 (e.g., does not detectably express ITGB3).

Additionally, the level of expression of a certain marker or combination of markers described herein may vary as compared to a control cell, such as corresponding control cell (e.g., a primary cell or model cell counterpart) (see, e.g., FIG. 14 and Table 6). For example, in certain embodiments, an induced multipotent placental cell described herein comprises higher expression of a marker or a combination of markers described herein (e.g., as described in FIG. 14/Table 6) as compared to a control cell. In certain embodiments, the induced multipotent placental cell comprises higher expression of a marker selected from the group consisting of TFAP2C, ABCG2, CLDN4, KRT7, SP6, and GATA3, and combinations thereof, as compared to a control cell. In certain embodiments, the expression is higher by at least about 10%, 20%, 30% or more. In certain embodiments, an induced multipotent placental cell described herein comprises lower expression of a marker or a combination of markers described herein (e.g., as described in FIG. 14/Table 6) as compared to a control cell. In certain embodiments, the induced multipotent placental cell comprises lower expression of a marker selected from the group consisting of ITGB3, LAMP3, DPP4, ARHGDIB, and GJA5, and combinations thereof, as compared to a control cell. In certain embodiments, the expression is lower by at least about 10%, 20%, 30% or more.

In certain embodiments, the pluripotent stem cells, which may be used in a method described herein, are induced pluripotent stem cells (iPSCs). In certain embodiments, the iPSCs are mammalian iPSCs, such as human iPSCs (hiPSCs). In certain embodiments, the pluripotent stem cells are embryonic stem cells (ESCs) (e.g., from a mammal, such as a human (hESCs)). In certain embodiments, the pluripotent stem cells are not hESCs.

In certain embodiments, prior to being cultured in the induction media, the pluripotent stem cells may be subcultured. Thus, in certain embodiments, the pluripotent stem cells may be singularized and seeded (e.g., at a particular seeding density). Accordingly, in certain embodiments, the pluripotent stem cells are removed from a solid substrate (e.g., the maintenance plate). In certain embodiments, the pluripotent stem cells are enzymatically removed from the solid substrate using, e.g., Accutase or Trypsin. In certain embodiments, pluripotent stem cells are enzymatically removed using Accutase. In certain embodiments, the pluripotent stem cells are enzymatically removed by incubating the cells with Accutase for 1 to 10 minutes at 37° C. In certain embodiments, pluripotent stem cells are enzymatically removed by incubating the cells with Accutase for 3 to 7 minutes at 37° C. In certain embodiments, the pluripotent stem cells are enzymatically removed by incubating the cells with Accutase for about 5 minutes at 37° C.

In certain embodiments, prior to being cultured in the induction media, the pluripotent stem cells are seeded at a density of about 1,000 cells/$cm^2$ to about 20,000 cells/$cm^2$. In certain embodiments, the pluripotent stem cells are seeded at a density of about 3,000 cells/$cm^2$ to about 15,000 cells/$cm^2$. In certain embodiments, the pluripotent stem cells are seeded at a density of about 1,000 cells/$cm^2$ to about 10,000 cells/$cm^2$. In certain embodiments, the pluripotent stem cells are seeded at a density of about 1,000 cells/$cm^2$, 2,000 cells/$cm^2$, 3,000 cells/$cm^2$, 4,000 cells/$cm^2$, 5,000 cells/$cm^2$, 6,000 cells/$cm^2$, 7,000 cells/$cm^2$, 8,000 cells/$cm^2$, 9,000 cells/$cm^2$, or 10,000 cells/$cm^2$. In certain embodiments, the pluripotent stem cells are seeded at a density between about 3,000 cells/$cm^2$ to about 6,000 cells/$cm^2$. In certain embodiments, the pluripotent stem cells are seeded at a density of about 3,000 cells/$cm^2$. In certain embodiments, the pluripotent stem cells are seeded at a density of about 4,000 cells/$cm^2$. In certain embodiments, the pluripotent stem cells are seeded at a density of about 5,000 cells/$cm^2$. In certain embodiments, the pluripotent stem cells are seeded at a density of about 6,000 cells/$cm^2$.

In certain embodiments, the cells are seeded/cultured on a solid substrate, such as a cell culture plate, that is coated with an extracellular matrix (ECM) protein. In certain embodiments, the ECM is matrigel (e.g., hESC qualified Matrigel). In certain embodiments, the ECM is laminin-511 (LN511). In certain embodiments, the ECM is laminin-521 (LN521). In certain embodiments, the ECM is Vitronectin XF. In certain embodiments, the ECM is Cultrex (e.g., Cultrex Stem Cell Qualified Reduced Growth Factor Basement Membrane Extract).

In certain embodiments, the pluripotent stem cells are cultured after seeding for a period of time prior to being contacted with the induction media. For example, in certain embodiments, the cells are cultured/maintained for a time period sufficient for the cells to attach to a solid substrate and form a monolayer. In certain embodiments, the pluripotent stem cells are cultured under conditions and in a culture media suitable for pluripotent cell maintenance, for e.g., at least about 12 hours, 24 hours, 36 hours 48 hours, 60 hours, 72 hours, 4 days, 5 days, or more after seeding. In certain embodiments, the pluripotent cells are cultured after seeding for about 2 days to about 4 days under conditions and in a culture media suitable for pluripotent cell maintenance. In certain embodiments, the pluripotent cells are cultured after seeding for about 3 days under conditions and in a culture media suitable for pluripotent cell maintenance. Such conditions and media suitable for culturing/maintaining pluripotent stem cells are known in the art. For example, in certain embodiments, the cells are cultured in a media comprising a Rho kinase inhibitor (e.g., a ROCK inhibitor, such as 5 μM of a ROCK inhibitor), which may be used to enhance cell survival after dissociation (see, e.g., Example 1). In certain embodiments, the cell culture media is a chemically defined media suitable for pluripotent stem cell maintenance, such as TeSR-E8 media or mTeSR Plus.

Oct-4 expression may be used as a marker of pluripotency, whereas CDX2 expression may be used as a marker of certain placental cells, such as trophectoderm and trophoblast cells. Thus, in certain embodiments, the pluripotent stem cells are cultured in the presence of the induction media for a time sufficient for Oct-4 expression to be reduced and CDX2 expression to be increased, wherein the expression levels are compared to those in a control pluripotent stem cell (e.g., that was not contacted with the induction media). In certain embodiments, the pluripotent stem cells are cultured in the presence of the induction media for a time sufficient for a majority of the cells in the population to become Oct-4 negative and CDX2 positive. In certain embodiments, the pluripotent stem cells are cultured in the presence of the induction media for a time sufficient for at least about 1%, 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% of the cells in the population to become Oct-4 negative and CDX2 positive. In certain embodiments, the pluripotent stem cells are cultured in the presence of the induction media for a time sufficient for at least about 60%, 70%, 80%, or 90% of the cells in the population to become Oct-4 negative and CDX2 positive (e.g., at least about 90%). In certain embodiments, the pluripotent stem cells are cultured in the presence of the induction media for a time sufficient for at least about 1%, 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% of the cells to differentiate into multipotent placental cells. In certain embodiments, the pluripotent stem cells are cultured in the presence of the induction media for a time sufficient for at least about 60%, 70%, 80%, or 90% of the cells to differentiate into multipotent placental cells (e.g., at least about 90%). Methods of measuring expression levels of various markers are known in the art and described herein.

In certain embodiments, the pluripotent stem cells are cultured in the presence of the induction media for at least about 3, 4, 5, 6, 7, 8, 9 or 10 days. In certain embodiments, the pluripotent stem cells are cultured in the presence of the induction media for between about 3 days to about 10 days. In certain embodiments, the pluripotent stem cells are cultured in the presence of the induction media for between about 3 days to about 7 days. In certain embodiments, the pluripotent stem cells are cultured in the presence of the induction media for between about 4 days to about 6 days. In certain embodiments, the pluripotent stem cells are cultured in the presence of the induction media for about 5 days.

As described herein, methods of the invention may be used to reliably produce a population of induced multipotent placental cells. Thus, in certain embodiments, at least about 1%, 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% of the pluripotent cells form induced multipotent placental cells in the presence of the induction media. In certain embodiments, the method produces a relatively homogeneous population of induced multipotent placental cells. Thus, in certain embodiments, at least about 60%, 70%, 80%, or 90% of the pluripotent cells form induced multipotent placental cells in the presence of the induction media (e.g., at least about 90%).

In certain embodiments, at least about 1%, 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90% 91%, 92%, 93%, 94%, 95%, 96%, 97%, 98%, 99% or 100% of the cells present after about 4 to about 6 days (e.g., 5 days) of being cultured in the presence of the induction media have differentiated into induced multipotent placental cells. In certain embodiments, at least about 60%, 70%, 80%, or 90% of the pluripotent cells form induced multipotent placental cells in the presence of the induction media (e.g., at least about 90%). In certain embodiments, at least about 60%, 70%, 80%, or 90% of the cells present after about 4 to about 6 days (e.g., 5 days) of being cultured in the presence of the induction media have differentiated into induced multipotent placental cells (e.g., at least about 90%). Thus, in certain embodiments, a method described herein may produce a population of cells that is comprised of at least about 1%, 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% induced multipotent placental cells. In certain embodiments, a method described herein may produce a population of cells that is comprised of at least about 60%, 70%, 80%, or 90% induced multipotent placental cells (e.g., at least about 90%).

In certain embodiments, the population of induced multipotent placental cells comprises induced trophectoderm cells. In certain embodiments, the population of induced multipotent placental cells comprises induced trophoblast cells.

In certain embodiments, a method described herein further comprises culturing or maintaining the population of induced multipotent placental cells. For example, in certain embodiments, a method described herein further comprises culturing the population of induced multipotent placental cells in a cell culture maintenance media (e.g., a maintenance media described herein, such as UM). In certain embodiments, the population of induced multipotent placental cells are cultured for at least about 2 passages (e.g., about 1 or 2 passages).

In certain embodiments, a method described herein further comprises differentiating the population of induced multipotent placental cells. In particular, in certain embodiments, a method described herein comprises culturing (e.g., sub-culturing) the population of induced multipotent placental cells under conditions suitable to produce a population of differentiated cells (e.g., STB-like or EVT-like cells).

For example, in certain embodiments, the induced multipotent placental cells are seeded at a density of about 500 cells/$cm^2$ to about 30,000 cells/$cm^2$. In certain embodiments, the induced multipotent placental cells are seeded at a density of about 1,000 cells/$cm^2$ to about 30,000 cells/$cm^2$. In certain embodiments, the induced multipotent placental cells are seeded at a density of about 1,000 cells/$cm^2$ to about 20,000 cells/$cm^2$. In certain embodiments, the induced multipotent placental cells are seeded at a density of about 10,000 cells/$cm^2$. In certain embodiments, the cells are seeded/cultured on a solid substrate, such as a cell culture plate, that is coated with an extracellular matrix (ECM) protein. In certain embodiments, the ECM is matrigel. In certain embodiments, the ECM is laminin-511 (LN511). In certain embodiments, the ECM is laminin-521 (LN521). In certain embodiments, the ECM is Vitronectin XF. In certain embodiments, the ECM is Cultrex.

After seeding, the induced multipotent placental cells may be cultured/maintained under conditions and in a culture media suitable for cell maintenance for a period of time. In certain embodiments, the cells are cultured/maintained for a time period sufficient for the cells to attach to a solid substrate and form a monolayer. For example, in certain embodiments the cells are cultured/maintained, for e.g., at least about 12 hours, 24 hours, 36 hours, 48 hours, 60 hours, 72 hours, or more after seeding. In certain embodiments, the cells are cultured after seeding for about 12 hours to about 2 days under conditions and in a culture media suitable for cell maintenance. In certain embodiments, the cells are cultured after seeding for about 24 hours under conditions and in a culture media suitable for cell maintenance. For example, in certain embodiments, the cells are cultured in a media comprising a Rho kinase inhibitor (e.g., a ROCK inhibitor, such as 5 μM of a ROCK inhibitor), which may be used to enhance cell survival after dissociation (see, e.g., Example 1). In certain embodiments, the cell culture media is an unconditioned media.

For differentiation, the induced multipotent placental cells may be cultured in a media and under conditions suitable for differentiation (e.g., in a media lacking a Rho inhibitor, such as a ROCK inhibitor). In certain embodiments, the media is an unconditioned media (see, e.g., Example 1).

In certain embodiments, the induced multipotent placental cells are cultured (e.g., sub-cultured) under conditions suitable to promote differentiation of the cells into STB-like cells. As used herein, the term "STB-like cell" refers to a cell that was generated by differentiating an induced multipotent placental cell described herein into a cell that has functional and molecular properties that are highly similar to a primary STB cell, but with certain distinctive characteristics (e.g., a unique transcriptional signature). STB cells are multinucleated placental cells that are capable of secreting hCG and do not express CDX2 or HLA class I molecules. Similarly, STB-like cells generated using a method described herein may have reduced CDX2 expression (e.g., as compared to an induced multipotent placental cell) or do not express CDX2. Additionally, in certain embodiments, the STB-like cells are multinucleated and/or are capable of secreting hCG. In certain embodiments, the STB-like cells express no or low levels of HLA class I molecules (e.g., HLA-G1/5) as compared to a control.

In certain embodiments, the induced multipotent placental cells are cultured (e.g., sub-cultured) under conditions suitable to promote differentiation of the cells into STB-like cells. In certain embodiments, the population of induced multipotent placental cells are cultured under normoxic conditions, thereby producing a population of STB-like cells. As used herein, the term "normoxia" or "normoxic conditions" refers to oxygen levels that range from about 18% to about 22%, such as about 20%. In certain embodiments, the induced multipotent placental cells are cultured under such conditions for a time period sufficient for the cells to gain one or more functional or molecular features of a primary STB cells (e.g., a STB cell feature described herein, such as a loss or reduction of CDX2 expression; multinucleation, or secretion of hCG).

In certain embodiments, the induced multipotent placental cells are cultured under differentiation conditions for at least about 3, 4, 5, 6, 7, 8, 9 or 10 days. In certain embodiments, the induced multipotent placental cells are cultured under conditions suitable for differentiation for about 4 to about 6 days. In certain embodiments, the induced multipotent placental cells are cultured under conditions suitable for differentiation for about 5 days. In certain embodiments, at least about 1%, 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% of the induced multipotent placental cells differentiate into STB-like cells. In certain embodiments, at least about 15% of the induced multipotent placental cells differentiate into STB-like cells. In certain embodiments, at least about 20% of the induced multipotent placental cells differentiate into STB-like cells. In certain embodiments, at least about 25% of the induced multipotent placental cells differentiate into STB-like cells. Thus, in certain embodiments, a method described herein may produce a population of cells that is comprised of at least about 1%, 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% STB-like cells.

In other embodiments, a method described herein further comprises culturing (e.g., sub-culturing) the population of induced multipotent placental cells under conditions suitable to produce a population of EVT-like cells. As used herein, the term "EVT-like cell" refers to a cell that was generated by differentiating an induced multipotent placental cell described herein into a cell that has functional and molecular properties that are highly similar to a primary EVT cell, but with certain distinctive characteristics (e.g., a unique transcriptional signature; see also, e.g., FIGS. 2B-C, D). Primary EVT cells do not express CDX2, have mesenchymal cell type characteristics (e.g., express matrix metallopeptidase 2 (MMP2) and α smooth muscle actin (ACTA2)), and express Ki67 and HLA-G (e.g., HLA-G1/5). Similarly, EVT-like cells generated using a method described herein may have reduced CDX2 expression (e.g., as compared to an induced multipotent placental cell) or do not express CDX2. Additionally, in certain embodiments, the EVT-like cell has certain mesenchymal cell type characteristics (e.g., express MMP2 and/or ACTA2; and/or have reduced Occuldin and/or tight junction protein 1 (TJP1) expression) and/or expresses Ki67 and/or HLA-G (e.g., HLA-G1/5).

In certain embodiments, the induced multipotent placental cells are cultured under conditions suitable to promote differentiation of the cells into EVT-like cells. In certain embodiments, the population of induced multipotent placental cells are cultured under hypoxic conditions, thereby producing a population of EVT-like cells. As used herein, the term "hypoxia" or "hypoxic conditions" refers to oxygen levels ranging from about 0.5% to about 7%, such as from about 0.5% to about 2%, or from about 1% to about 2%. In certain embodiments, the induced multipotent placental cells are cultured under such conditions for a time period sufficient for the cells to gain one or more functional or molecular features of EVT cells (e.g., a EVT cell feature described herein, such as a loss or reduction of CDX2 expression; or Ki67 and/or HLA-G expression). In certain embodiments, the induced multipotent placental cells are cultured under conditions suitable for differentiation for at least about 3, 4, 5, 6, 7, 8, 9 or 10 days. In certain embodiments, the induced multipotent placental cells are cultured under conditions suitable for differentiation for about 4 to about 6 days. In certain embodiments, the induced multipotent placental cells are cultured under conditions suitable for differentiation for about 5 days. In certain embodiments, at least about 1%, 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% of the induced multipotent placental cells differentiate into EVT-like cells. Thus, in certain embodiments, a method described herein may produce a population of cells that is comprised of at least about 1%, 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% EVT-like cells.

Cell Culture Induction Media

As described herein, a cell culture induction media comprising a retinoid (e.g., retinoic acid (tretinoin), or a salt thereof), and optionally, a Wnt signaling agonist (e.g., CHIR-99021, or a salt thereof), may be used in a method described herein (e.g., in a method of producing an induced multipotent placental cell). As used herein, the term "induction media" refers to a cell culture media comprising a retinoid, and optionally, a Wnt signaling agoinst, which can be used to produce the multipotent placental cells described herein.

In certain embodiments, the induction media comprises a retinoid (e.g., retinoic acid, or a salt thereof), and a Wnt signaling agonist (e.g., CHIR-99021, or a salt thereof). Thus, certain embodiments provide an induction media comprising a retinoid (e.g., retinoic acid, or a salt thereof), and a Wnt signaling agonist (e.g., CHIR-99021, or a salt thereof) (e.g., for use in a method described herein).

In certain embodiments, an induction media described herein comprises from about 0.1 to about 10 μM of a retinoid (e.g., retinoic acid, or a salt thereof). In certain embodiments, the induction media comprises at least about 1 μM of a retinoid (e.g., retinoic acid, or a salt thereof). In certain embodiments, the induction media comprises about 1 μM of a retinoid (e.g., retinoic acid, or a salt thereof).

In certain embodiments, an induction media described herein comprises from about 2 to about 20 μM of a Wnt signaling agonist (e.g., CHIR-99021, or a salt thereof). In certain embodiments, the induction media comprises at least about 8 μM of a Wnt signaling agonist (e.g., CHIR-99021, or a salt thereof). In certain embodiments, the induction media comprises about 8 μM of a Wnt signaling agonist (e.g., CHIR-99021, or a salt thereof).

In addition to a retinoid, and optionally, a Wnt signaling agonist, an induction media described herein should further comprise other ingredients that support maintenance of the cultured cells. Suitable combinations of ingredients are known in the art and described herein. For example, the media may be a nutrient solution comprising standard cell culture ingredients, such as amino acid(s), vitamin(s), trace metal(s), inorganic salt(s), carbon energy source(s), and/or buffer(s), or combinations thereof. In certain embodiments, the media may be a conditioned media that comprises undefined components secreted from cultured cells. In other embodiments, the media is an unconditioned media, which does not comprise components secreted from cultured cells. In certain embodiments, the media is a chemically defined media, which contains only specified components.

In certain embodiments, an induction media described herein comprises a basal media, such as a chemically defined basal media. Chemically defined basal media are known in the art and include, but are not limited to, Dulbecco's modified eagle medium (DMEM), DMEM/F12, Iscove's Modified Dulbecco's medium (IMDM) and RPMI-1640. In certain embodiments, the basal media is DMEM/F12. In certain embodiments, an induction media described herein further comprises BSA or a knockout serum replacement (KSR). In certain embodiments an induction media described herein further comprises L-Glutamine or GlutaMAX; one or more antibiotics; Non-Essential Amino Acids; one or more vitamins; and/or β-mercaptoethanol.

In certain embodiments, an induction media described herein may comprise a media described in La Regina et al., Culturing pluripotent stem cells: State of the art, challenges and future opportunities, Current Opinion in Systems Biology, 2021, 100364, doi.org/10.1016/j.coisb.2021.100364, which is incorporated by reference herein for all purposes.

In certain embodiments, an induction media described herein comprises a minimal media. For example, in certain embodiments, the induction media comprises an E6 media formulation. In certain embodiments, an induction media described herein does not comprise a minimal media. For example, in certain embodiments, the induction media does not comprise an E6 media formulation.

In certain embodiments, the induction media comprises DMEM/F12, knockout serum replacement, MEM non-essential amino acids, GlutaMAX, β-mercaptoethanol, and a retinoid. In certain embodiments, the induction media comprises DMEM/F12, knockout serum replacement, MEM non-essential amino acids, GlutaMAX, β-mercaptoethanol, a retinoid, and a Wnt signaling agonist. In certain embodiments, the induction media consists of DMEM/F12, knockout serum replacement, MEM non-essential amino acids, GlutaMAX, β-mercaptoethanol, a retinoid, and a Wnt signaling agonist.

In certain embodiments, the induction media comprises DMEM/F12, knockout serum replacement, MEM non-essential amino acids, GlutaMAX, β-mercaptoethanol, and retinoic acid, or a salt thereof. In certain embodiments, the induction media comprises DMEM/F12, knockout serum replacement, MEM non-essential amino acids, GlutaMAX, β-mercaptoethanol, retinoic acid, or a salt thereof, and CHIR-99021, or a salt thereof. In certain embodiments, the induction media consists of DMEM/F12, knockout serum replacement, MEM non-essential amino acids, GlutaMAX, β-mercaptoethanol, retinoic acid, or a salt thereof, and CHIR-99021, or a salt thereof.

In certain embodiments, the induction media comprises DMEM/F12, 20% knockout serum replacement, MEM non-essential amino acids (1×), GlutaMAX (1×), 0.1 mM β-mercaptoethanol, 1 μM retinoic acid, and 8 μM CHIR-99021. In certain embodiments, the induction media consists of DMEM/F12, 20% knockout serum replacement, MEM non-essential amino acids (1×), GlutaMAX (1×), 0.1 mM β-mercaptoethanol, 1 μM retinoic acid, and 8 μM CHIR-99021.

In certain embodiments, the induction media further comprises a population of cells described herein (e.g., a population of pluripotent stem cells, such as iPSCs or ESCs; or a population of induced multipotent placental cells, such as induced trophectoderm cells or induced trophoblast cells).

Certain embodiments provide a cell culture comprising a cell culture media described herein (e.g., an induction media) and a population of cells described herein (e.g., a population of pluripotent stem cells, such as iPSCs or ESCs; or a population of induced multipotent placental cells, such as induced trophectoderm cells or induced trophoblast cells).

Certain embodiments also provide a composition comprising a retinoid (e.g., retinoic acid, or a salt thereof) and a Wnt signaling agonist (e.g., CHIR-99021, or a salt thereof). Such a composition may be used as a cell culture supplement to produce a cell culture induction media described herein. In particular, the supplement can be used to produce a functional cell culture medium of the invention by combining it with other cell culture ingredients to produce an appropriate medium formulation. The supplement may also contain one or more additional cell culture ingredients, e.g., one or more cell culture ingredients selected from the group consisting of amino acids, vitamins, inorganic salts, trace elements, carbon energy sources and buffers. Such a supplement may be a concentrated liquid supplement (e.g., a 2× to 250× concentrated liquid supplement) or may be a dry supplement.

Certain embodiments also provide a method of preparing a cell culture induction media capable of producing a population of induced multipotent placental cells, the method comprising adding a retinoid (e.g., retinoic acid, or a salt thereof), and optionally, a Wnt signaling agonist (e.g., CHIR-99021, or a salt thereof), to a cell culture media (e.g., unconditioned media).

Induced Multipotent Placental Cells, and Progeny and Compositions Thereof

As described herein, methods and compositions of the invention may be used to produce induced multipotent placental cells, and progeny thereof. These cells may be used as models for placental cells and placental tissue (e.g., cell models for trophectoderm, trophoblast cells, STB cells and EVT cells).

Thus, certain embodiments provide a placental cell or a population of placental cells as described herein (e.g., produced by a method described herein (e.g., as described in Example 1)). In certain embodiments, the placental cell is an induced multipotent placental cell described herein (e.g., produced by the method described herein, such as in Example 1, wherein the exposure to RA+CHIR is for 3, 4 or 5 days). In certain embodiments, the induced multipotent placental cell comprises one or more properties (e.g., molecular properties, such as an expression pattern) described herein (see, e.g., FIG. 14/Table 6). In certain embodiments, the induced multipotent placental cell is an iMPC1 cell (i.e., as produced by the method described in Example 1, wherein the cell is exposed to RA+CHIR for 5 days, which may also be referred to as an iMPC1-D5 cell). In certain embodiments, the induced multipotent placental cell is an iMPC1-DN cell (i.e., as produced by the method described in Example 1, wherein the cell is exposed to RA+CHIR for N days, wherein N is, e.g., 3, 4, or 5 days). In certain embodiments, the induced multipotent placental cell is an iMPC1-D3 cell (i.e., as produced by the method described in Example 1, wherein the cell is exposed to RA+CHIR for 3 days). In certain embodiments, the induced multipotent placental cell is an iMPC1-D4 cell (i.e., as produced by the method described in Example 1, wherein the cell is exposed to RA+CHIR for 4 days). In certain embodiments, the placental cell is an induced trophectoderm cell. In certain embodiments, the placental cell is an induced trophoblast cell. In certain embodiments, the placental cell is a STB-like cell described herein (e.g., produced by a method described herein). In certain embodiments, the STB-like cell comprises one or more properties (e.g., molecular properties, such as an expression pattern) described herein. In certain embodiments, the STB-like cell is an iSTBL1 cell (i.e., as produced by the method described in Example 1). In certain embodiments, the placental cell is an EVT-like cell described herein (e.g., produced by a method described herein). In certain embodiments, the EVT-like cell comprises one or more properties (e.g., molecular properties, such as an expression pattern) described herein. In certain embodiments, the EVT-like cell is an iEVTL1 cell (i.e., as produced by the method described in Example 1).

In certain embodiments, the placental cell is present in a population of cells. In certain embodiments, the population of cells is relatively homogenous. For example, in certain embodiments, the population of cells comprises at least about 60%, 65%, 70%, 75%, 80%, 85%, 90%, 95%, 96%, 97%, 98%, 99% or 100% of a particular type of produced placental cells. In certain embodiments, the population of cells comprises at least about 90% of a particular type of produced placental cells.

In certain embodiments, the produced placental cell or population of produced placental cells is present in a cell culture media (e.g., a cell culture media described herein). Thus, certain embodiments provide a cell culture comprising a cell culture media (e.g., a cell culture media described herein) and a produced placental cell or population of produced placental cells. In certain embodiments the cell(s) are induced multipotent placental cells (e.g., model trophectoderm or trophoblast cells). In certain embodiments the cell(s) are STB-like cells. In certain embodiments, the cells are EVT-like cells.

Certain embodiments also provide a composition comprising a placental cell or a population of placental cells described herein and a carrier (e.g., wherein the cell(s) were produced using a method described herein). In certain embodiments, the composition is a pharmaceutical composition comprising a pharmaceutically acceptable carrier.

Cells of the present invention (i.e., induced multipotent placental cells described herein, or progeny thereof, e.g., produced by a method described herein) can be provided in kits, with appropriate packaging material. For example, the cells can be provided as frozen stocks, optionally accompanied by separately packaged appropriate factors and media, as previously described herein, for maintenance culture. Additionally, separately packaged factors for induction of differentiation also may be provided. The kits may also include instructions for maintaining the cells or for differentiating such cells (e.g., into STB-like cells or EVT-like cells).

Kits containing effective amounts of appropriate factors for multipotent placental cell induction and culture are also provided by the present invention (e.g., a retinoid and a Wnt signaling agonist, such as a combination of retinoic acid and CHIR-99021). Pluripotent stem cells may be cultured, using the induction factor(s) or induction media supplied as a kit component. For example, certain embodiments provide a kit comprising an induction media described herein, and instructions for culturing a population pluripotent stem cells in the presence of the induction media to produce a population of induced multipotent placental cells. In certain embodiments, the kit further comprises a population of pluripotent stem cells (e.g., iPSCs, such as hiPSCs).

Certain other embodiments provide a kit comprising a retinoid (e.g., retinoic acid, or a salt thereof), and a Wnt signaling agonist (e.g., CHIR-99021, or a salt thereof), and instructions for preparing an induction media comprising the retinoid or Wnt signaling agonist, and for culturing a population pluripotent stem cells in the presence of the induction media to produce a population of induced multipotent placental cells. In certain embodiments, the kit further comprises a basal media. In certain embodiments, the kit further comprises a population of pluripotent stem cells (e.g., iPSCs, such as hiPSCs).

Methods of Use

The induced multipotent placental cells described herein, and differentiated progeny thereof, (e.g., produced using a method or composition described herein) may be used for a variety of applications, including but not limited to, methods of using such cells to elucidate early cell fate decisions, to understand how various pregnancy complications from placental abnormalities arise (e.g., using the cells to screen for genetic or non-genetic risk factors, e.g., for poor placental attachment or differentiation), to study the mother-placenta-fetus transport properties (e.g., to better understand drug interactions and bacterial infections), for cell therapy in women who are at a high risk for pregnancy, and to enhance or support in vitro fertilization (IVF).

Thus, certain embodiments provide a method of identifying a test agent or a test condition that is capable of modifying the structure, function or development of placental cells/tissue, the method comprising contacting a population of induced multipotent placental cells as described herein, or differentiated progeny thereof (e.g., a population of STB-like cells as described herein and/or a population of EVT-like cells as described herein), or placental tissue comprising such cells, with the test agent or under the test condition, wherein the agent/condition is identified as a modifier when the structure, function or development of the placental cells/tissue differs as compared to a control (e.g., corresponding cells or tissue that were not contacted with the test agent or under the test condition). In certain embodiments, the test agent is a biologically active agent, such as a therapeutic agent. In certain embodiments, the test agent is a pathogen, such as bacteria or a virus. In certain embodiments, the test agent is a nucleic acid (e.g., encoding gene or a protein of interest; or capable of providing interference or knock-down of a gene of interest), and the cells are contacted, e.g., via transfection or transduction. In certain embodiments, a test condition may a non-genetic risk factor, such as diet or exercise.

Thus, in certain embodiments the cells may be used to examine the impact of upregulation, interference, or knock-down of certain genes/pathways thought to play a role in placentation (e.g., to examine genetic risk factors). In certain embodiments, non-genetic risk factors, such as diet and exercise, may be examined to explore their impact on normal placenta formation.

Certain embodiments also provide a method of evaluating the transport properties of placental tissue, the method comprising contacting the placental tissue with a test agent and determining whether the test agent is transported across a barrier model of the placental tissue, wherein the placental tissue comprises a population of induced multipotent placental cells as described herein, or differentiated progeny thereof (e.g., a population of STB-like cells as described herein; and/or a population of EVT-like cells as described herein). In certain embodiments, the test agent is a biologically active agent, such as a therapeutic agent. In certain embodiments, the test agent is a pathogen, such as bacteria or a virus. In certain embodiments, the placental tissue is contacted with the test agent in vitro under suitable culture conditions.

Certain embodiments also provide a method comprising contacting a fertilized cell, or progeny thereof, with a population of induced multipotent placental cells as described herein, or differentiated progeny thereof (e.g., a population of STB-like cells as described herein; and/or a population of EVT-like cells as described herein), or placental tissue comprising such cells, under suitable conditions (e.g., for cell growth). In certain embodiments, the fertilized cell is a mammalian cell, such as a human cell. In certain embodiments, the fertilized cell is not a human cell. For example, such a method may be used for enhancing the success of an in vitro fertilization (IVF) procedure.

Certain embodiments of the invention provide a population of induced multipotent placental cells as described herein, or differentiated progeny thereof (e.g., a population of STB-like cells as described herein; and/or a population of EVT-like cells as described herein), or placental tissue comprising such cells, for use in medical therapy.

Certain embodiments also provide a method of treating a placental abnormality in a pregnant female mammal (e.g., a human), the method comprising administering a population of induced multipotent placental cells as described herein, or differentiated progeny thereof (e.g., a population of STB-like cells as described herein; and/or a population of EVT-like cells) as described herein to the mammal.

Certain embodiments of the invention provide a population of induced multipotent placental cells as described herein, or differentiated progeny thereof (e.g., a population of STB-like cells as described herein; and/or a population of EVT-like cells as described herein) for use in treating a placental abnormality in a pregnant female mammal.

Certain embodiments of the invention provide the use of a population of induced multipotent placental cells as described herein, or differentiated progeny thereof (e.g., a population of STB-like cells as described herein; and/or a population of EVT-like cells as described herein) to prepare a medicament for treating a placental abnormality in a pregnant female mammal.

Administration

The induced multipotent placental cells cells, or their differentiated progeny (e.g., STB-like or EVT-like cells), (hereinafter referenced as cells) can be administered to a subject by a several methods available to the art, including but not limited to localized injection, catheter administration, systemic injection, intraperitoneal injection, parenteral administration, intracranial injection, intra-arterial injection, intravenous injection, intraplacental injection, intrauterine injection, intrathecal administration, intraventricular administration, intracisternal administration, intrastriatal administration, intranigral administration, intramuscular injection, surgical injection into a tissue of interest or via direct application to tissue surfaces (e.g., during surgery or on a wound).

One method to increase cell survival is to incorporate the cells of interest into a biopolymer or synthetic polymer. Depending on the patient's condition, the site of injection might prove inhospitable for cell seeding and growth because of scarring or other impediments. Examples of biopolymer include, but are not limited to cells mixed with fibronectin, fibrin, fibrinogen, thrombin, collagen, and proteoglycans. This could be constructed with or without included cytokines, differentiation factors, angiogenesis factors and/or anti-apoptosis factors. Additionally, these could be in suspension. Another alternative is a three-dimension gel with cells entrapped within the interstices of the cell biopolymer admixture. Again cytokines, differentiation factors, angiogenesis factors and/or anti-apoptosis factors could be included within the gel. These could be deployed by injection via various routes described herein, via catheters or other surgical procedures.

The quantity of cells to be administered will vary for the subject being treated. In one embodiment, between about $10^3$ to about $10^9$, about $10^4$ to about $10^8$, about $10^5$ to about $10^7$, or about $10^7$ cells can be administered to a human subject. The precise determination of what would be considered an effective dose may be based on factors individual to each patient, including their size, age, disease or injury, size of damage caused by the disease or injury and amount of time since the damage occurred.

When administering a therapeutic composition of the present invention (e.g., a composition comprising cells described herein), it will generally be formulated in a unit dosage injectable form (solution, suspension, emulsion). The doses may be single doses or multiple doses over a period of several days. The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells.

Sterile injectable solutions can be prepared by incorporating the cells utilized in practicing the present invention in the required amount of the appropriate solvent with various amounts of the other ingredients, as desired.

In one embodiment, cells can be administered initially, and thereafter maintained by further administration of cells. For instance, cells can be administered by one method, and thereafter further administered by a different or the same method.

Examples of compositions comprising the induced multipotent placental cells, or differentiated progeny thereof, include liquid preparations for administration, including suspensions; and, preparations for direct or intravenous administration (e.g., injectable administration), such as sterile suspensions or emulsions. Such compositions may be in admixture with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE," 17th edition, 1985, incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, PVA, ethyl cellulose, hydroxypropyl cellulose, carbomer, and the like. The preferred concentration of the thickener will depend upon the agent selected and the desired viscosity. Viscous compositions are normally prepared from solutions by the addition of such thickening agents.

A pharmaceutically acceptable preservative or cell stabilizer can be employed to increase the life of the compositions. Preferably, they will not affect the viability or efficacy of the cells as described in the present invention.

Compositions can be administered in dosages and by techniques available to those skilled in the medical and veterinary arts taking into consideration such factors as the age, sex, weight, and condition of the particular subject, and the composition form used for administration (e.g., solid vs. liquid).

Matrices are also used to deliver cells of the present invention to specific anatomic sites, where particular growth factors incorporated into the matrix, or encoded on plasmids incorporated into the matrix for uptake by the cells, can be used to direct the growth of the initial cell population. A polynucleotide(s) (e.g., DNA) can be incorporated within pores of the matrix, for example, during the foaming process used in the formation of certain polymer matrices. As the polymer used in the foaming process expands, it entraps the polynucleotide within the pores, allowing controlled and sustained release of polynucleotide (e.g., plasmid DNA). Such a method of matrix preparation is described by Shea, et al. (*Nature Biotechnology* (1999) 17: 551-554).

In some embodiments, the cells are encapsulated. One goal in encapsulation in cell therapy is to protect allogeneic and xenogeneic cell transplants from destruction by the host immune response, thereby eliminating or reducing the need for immuno-suppressive drug therapy. Techniques for microencapsulation of cells are available to the art (see, for example, Chang, P., et al., *Trends in Biotech.* 1999; 17:78-83; Matthew, H. W., et al., ASAIO Trans. 1991; 37(3):M328-30; Yanagi, K., et al., *ASAIO Trans.* 1989; 35(3):570-2; Cai Z. H., et al., *Artif Organs.* 1988; 12(5):388-93; Chang, T. M., *Artif Organs.* 1992; 16(1):71-4). Materials for microencapsulation of cells include, for example, polymer capsules, dendrimer, liposome, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers. U.S. Pat. No. 5,639,275, for example, describes improved devices and methods for long-term, stable expression of a biologically active molecule using a biocompatible capsule containing genetically engineered cells.

For the purposes described herein, either autologous, allogeneic or xenogenic cells of the present invention can be administered to a subject, either in differentiated or undifferentiated form, genetically altered or unaltered, by direct injection to a desired site, systemically, on or around the surface of an acceptable matrix, or in combination with a pharmaceutically acceptable carrier.

Certain Embodiments

Embodiment 1. A method of producing a population of induced multipotent placental cells, the method comprising culturing a population of pluripotent stem cells in the presence of an induction media comprising a retinoid and a Wnt signaling agonist, under conditions suitable to produce the population of induced multipotent placental cells.

Embodiment 2. The method of embodiment 1, wherein the retinoid is a compound of formula I:

(I)

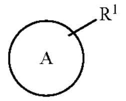

wherein:

ring A is phenyl or cyclohexen-1-yl, which phenyl or cyclohexen-1-yl is optionally substituted with one or more groups independently selected from $(C_1\text{-}C_8)$alkyl, $(C_3\text{-}C_{10})$cycloalkyl, $(C_1\text{-}C_8)$alkoxy, and $(C_3\text{-}C_8)$cycloalkyloxy; and $R^1$ is $(C_5\text{-}C_{20})$alkenyl that is substituted with one or more groups independently selected from hydroxy, carboxy, or $(C_1\text{-}C_6)$alkoxycarbonyl;

or a salt thereof.

Embodiment 3. The method of embodiment 2, wherein the retinoid is a compound of formula (Id):

(Id)

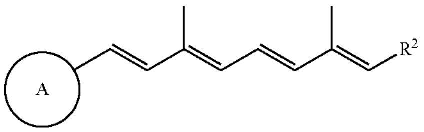

wherein:

$R^2$ is hydroxymethyl, carboxy, or $(C_1\text{-}C_6)$alkoxycarbonyl; or a salt thereof.

Embodiment 4. The method of embodiment 2 or 3, wherein ring A is selected from the group consisting of:

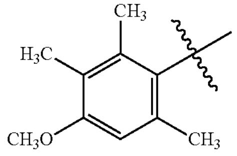

and

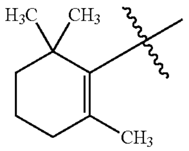

.

Embodiment 5. The method of embodiment 2, wherein the retinoid is retinol, retinoic acid (tretinoin), isotretinoin, alitretinoin, acitretin, adapalene, bexarotine, or tazarotene or a salt thereof.

Embodiment 6. The method of embodiment 2, wherein the retinoid is retinoic acid (tretinoin):

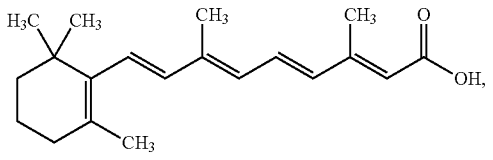

Retinoic acid (Tretinoin)

or a salt thereof.

Embodiment 7. The method of any one of embodiments 1-6, wherein the Wnt signaling agonist is selected from the group consisting of a Wnt ligand (e.g., Wnt3a), an R-spondin protein, BIO, SB216763, CHIR-99021, and salts thereof.

Embodiment 8. The method of embodiment 7, wherein the Wnt signaling agonist is CHIR-99021, or a salt thereof.

Embodiment 9. The method of embodiment 1, wherein the retinoid is retinoic acid, or a salt thereof, and the Wnt signaling agonist is CHIR-99021, or a salt thereof.

Embodiment 10. The method of any one of embodiments 1-9, wherein the pluripotent stem cells are embryonic stem cells (ESCs) or induced pluripotent stem cells (iPSCs).

Embodiment 11. The method of embodiment 10, wherein the pluripotent stem cells are iPSCs.

Embodiment 12. The method of embodiment 11, wherein the pluripotent stem cells are human iPSCs (hiPSCs).

Embodiment 13. The method of any one of embodiments 1-12, wherein the induction media comprises from about 0.1 to about 10 μM of a retinoid (e.g., retinoic acid, or a salt thereof).

Embodiment 14. The method of any one of embodiments 1-12, wherein the induction media comprises about 1 μM of a retinoid (e.g., retinoic acid, or a salt thereof).

Embodiment 15. The method of any one of embodiments 1-14, wherein the induction media comprises from about 2 to about 20 μM of a Wnt signaling agonist (e.g., CHIR-99021, or a salt thereof).

Embodiment 16. The method of any one of embodiments 1-14, wherein the induction media comprises about 8 μM of a Wnt signaling agonist (e.g., CHIR-99021, or a salt thereof).

Embodiment 17. The method of any one of embodiments 1-16, wherein the induction media comprises a chemically defined basal media.

Embodiment 18. The method of embodiment 17, wherein the chemically defined basal media is DMEM/F12.

Embodiment 19. The method of any one of embodiments 1-18, wherein the induction media comprises one or more additional ingredients selected from the group consisting of amino acid(s), vitamin(s), trace metal(s), inorganic salt(s), carbon energy source(s), buffer(s), and combinations thereof.

Embodiment 20. The method of any one of embodiments 1-19, wherein the induction media comprises DMEM/F12, knockout serum replacement, MEM non-essential amino acids, GlutaMAX, β-mercaptoethanol, retinoic acid, or a salt thereof, and CHIR-99021, or a salt thereof.

Embodiment 21. The method of any one of embodiments 1-20, wherein prior to being cultured in the presence of the induction media, the population of pluripotent stem cells are seeded for culturing at a density ranging from about 3,000 cells/$cm^2$ to about 15,000 cells/$cm^2$.

Embodiment 22. The method of embodiment 21, wherein the population of pluripotent stem cells are seeded for culturing at a density of about 6,000 cells/$cm^2$.

Embodiment 23. The method of any one of embodiments 1-22, wherein the population of pluripotent stem cells are cultured on a solid substrate, and wherein the solid substrate is coated with an extracellular matrix (ECM) protein.

Embodiment 24. The method any one of embodiments 1-23, wherein the population of pluripotent stem cells are cultured in the presence of the induction media for a time sufficient for a majority of the cells in the population to become OCT4 negative and CDX2 positive.

Embodiment 25. The method of any one of embodiments 1-24, wherein the population of pluripotent stem cells are cultured in the presence of the induction media for between about 4 to about 6 days (e.g., about 5 days).

Embodiment 26. The method of embodiment 25, wherein at least about 90% of the cells present after about 5 days of being cultured in the presence of the induction media have differentiated into induced multipotent placental cells.

Embodiment 27. The method of any one of embodiments 1-26, wherein the population of induced multipotent placental cells comprises induced trophectoderm cells.

Embodiment 28. The method of any one of embodiments 1-27, wherein the population of induced multipotent placental cells comprises induced trophoblast cells.

Embodiment 29. The method of any one of embodiments 1-28, wherein the induced multipotent placental cells express CDX2 and one or more markers selected from the group consisting of Keratin 18 (KRT18), Keratin 7 (KRT7), KLF4, GATA3, E-cadherin, and combinations thereof.

Embodiment 30. The method of any one of embodiments 1-29, wherein the induced multipotent placental cells do not express OCT4, FoxA2 and/or SOX17.

Embodiment 31. The method of embodiment 30, wherein the induced multipotent placental cells do not express OCT4.

Embodiment 32. The method of any one of embodiments 1-31, further comprising culturing and/or maintaining the population of induced multipotent placental cells.

Embodiment 33. The method of any one of embodiments 1-32, further comprising culturing the population of induced multipotent placental cells under conditions suitable to produce a population of differentiated cells.

Embodiment 34. The method of embodiment 33, wherein the population of induced multipotent placental cells are seeded for culturing at a density ranging from about 1,000 cells/$cm^2$ to about 30,000 cells/$cm^2$.

Embodiment 35. The method of embodiment 34, wherein the population of induced multipotent placental cells are seeded for culturing at a density of about 10,000 cells/$cm^2$.

Embodiment 36. The method of any one of embodiments 33-35, wherein the population of induced multipotent placental cells are cultured for between about 4 to about 6 days under conditions suitable for differentiation.

Embodiment 37. The method of embodiment 36, wherein the population of induced multipotent placental cells are cultured for about 5 days under conditions suitable for differentiation.

Embodiment 38. The method of any one of embodiments 33-37, wherein the population of induced multipotent placental cells are cultured under conditions suitable to produce a population of syncytiotrophoblast (STB)-like cells.

Embodiment 39. The method of embodiment 38, wherein the population of induced multipotent placental cells are cultured under normoxic conditions.

Embodiment 40. The method of embodiment 38 or 39, wherein the STB-like cells are multinucleated and/or are capable of secreting hCG.

Embodiment 41. The method of any one of embodiments 33-37, wherein the population of induced multipotent placental cells are cultured under conditions suitable to produce a population of extravillous trophoblast (EVT)-like cells.

Embodiment 42. The method of embodiment 41, wherein the population of induced multipotent placental cells are cultured under hypoxic conditions.

Embodiment 43. The method of embodiment 41 or 42, wherein the EVT cells express Ki67 and/or an HLA-G marker.

Embodiment 44. A population of induced multipotent placental cells produced by the method of any one of embodiments 1-32.

Embodiment 45. A method of producing a population of syncytiotrophoblast (STB)-like cells comprising culturing the population of induced multipotent placental cells of embodiment 44 under conditions suitable to produce a population of STB-like cells.

Embodiment 46. A method of producing a population of extravillous trophoblast (EVT)-like cells comprising culturing the population of induced multipotent placental cells of embodiment 44 under conditions suitable to produce a population of EVT-like cells.

Embodiment 47. A population of syncytiotrophoblast (STB)-like cells produced by the method of any one of embodiments 33-40 and 45.

Embodiment 48. A population of extravillous trophoblast (EVT)-like cells produced by the method of any one of embodiments 33-37, 41-43 and 46.

Embodiment 49. A composition comprising the population of induced multipotent placental cells of embodiment 44, the population of STB-like cells of embodiment 47 or the population of EVT-like cells of embodiment 48, and a carrier.

Embodiment 50. A cell culture induction media comprising a retinoid and a Wnt signaling agonist.

Embodiment 51. The induction media of embodiment 50, wherein the retinoid is a compound of formula I:

(I)

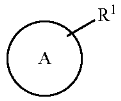

wherein:

ring A is phenyl or cyclohexen-1-yl, which phenyl or cyclohexen-1-yl is optionally substituted with one or more groups independently selected from $(C_1\text{-}C_8)$alkyl, $(C_3\text{-}C_{10})$cycloalkyl, $(C_1\text{-}C_8)$alkoxy, and $(C_3\text{-}C_8)$cycloalkyloxy; and $R^1$ is $(C_5\text{-}C_{20})$alkenyl that is substituted with one or more groups independently selected from hydroxy, carboxy, or $(C_1\text{-}C_6)$alkoxycarbonyl;

or a salt thereof.

Embodiment 52. The induction media of embodiment 51, wherein the retinoid is a compound of formula (Id):

(Id)

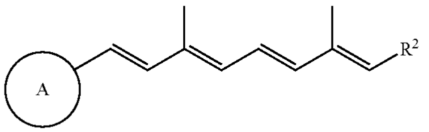

wherein:

$R^2$ is hydroxymethyl, carboxy, or $(C_1\text{-}C_6)$alkoxycarbonyl; or a salt thereof.

Embodiment 53. The induction media of embodiment 51 or 52, wherein ring A is selected from the group consisting of:

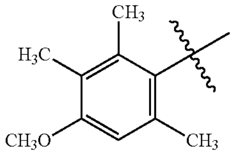

and

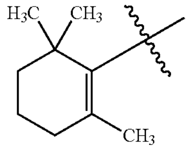

.

Embodiment 54. The induction media of embodiment 50, wherein the retinoid is retinol, retinoic acid (tretinoin), isotretinoin, alitretinoin, acitretin, adapalene, bexarotine, or tazarotene or a salt thereof.

Embodiment 55. The induction media of embodiment 54, wherein the retinoid is retinoic acid (tretinoin):

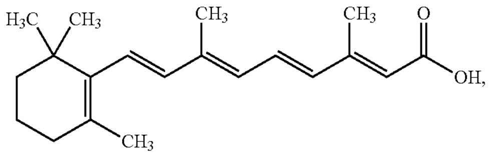

Retinoic acid (Tretinoin)

or a salt thereof.

Embodiment 56. The induction media of any one of embodiments 50-55, wherein the Wnt signaling agonist is selected from the group consisting of a Wnt ligand (e.g., Wnt3a), an R-spondin protein, BIO, SB216763, CHIR-99021, and salts thereof.

Embodiment 57. The induction media of embodiment 56, wherein the Wnt signaling agonist is CHIR-99021, or a salt thereof.

Embodiment 58. The induction media of embodiment 50, wherein the retinoid is retinoic acid (tretinoin), or a salt thereof, and the Wnt signaling agonist is CHIR-99021, or a salt thereof.

Embodiment 59. The induction media of any one of embodiments 50-58, comprising from about 0.1 to about 10 μM of a retinoid (e.g., retinoic acid, or a salt thereof).

Embodiment 60. The induction media of embodiment 59, which comprises about 1 of a retinoid (e.g., retinoic acid, or a salt thereof).

Embodiment 61. The induction media of any one of embodiments 50-60, which comprises from about 2 to about 20 μM of a Wnt signaling agonist (e.g., CHIR-99021, or a salt thereof).

Embodiment 62. The induction media of embodiment 61, which comprises about 8 of a Wnt signaling agonist (e.g., CHIR-99021, or a salt thereof).

Embodiment 63. The induction media of any one of embodiments 50-62, which comprises a chemically defined basal media.

Embodiment 64. The induction media of embodiment 63, wherein the chemically defined basal media is DMEM/F12.

Embodiment 65. The induction media of any one of embodiments 50-64, wherein the induction media further comprises one or more additional ingredients selected from the group consisting of amino acid(s), vitamin(s), trace metal(s), inorganic salt(s), carbon energy source(s), buffer(s), and combinations thereof.

Embodiment 66. The induction media of any one of embodiments 50-65, which comprises DMEM/F12, knockout serum replacement, MEM non-essential amino acids, GlutaMAX, β-mercaptoethanol, retinoic acid (tretinoin), or a salt thereof, and CHIR-99021, or a salt thereof.

Embodiment 67. The induction media of embodiment 66, which comprises DMEM/F12, 20% knockout serum replacement, MEM non-essential amino acids (1×), GlutaMAX (1×), 0.1 mM β-mercaptoethanol, 1 μM retinoic acid (tretinoin), and 8 μM CHIR-99021.

Embodiment 68. A cell culture comprising an induction media as described in any one of embodiments 50-67 and a population of pluripotent stem cells.

Embodiment 69. A kit comprising a retinoid (e.g., retinoic acid, or a salt thereof), a Wnt signaling agonist (e.g., CHIR-99021, or a salt thereof), and instructions for preparing an induction media comprising the retinoid and the Wnt signaling agonist, and for culturing a population pluripotent stem cells in the presence of the induction media to produce a population of induced multipotent placental cells.

Embodiment 70. The kit of embodiment 69, further comprising a basal media.

Embodiment 71. The kit of embodiment 69 or 70, further comprising a population of pluripotent stem cells.

Embodiment 72. A method of identifying a test agent that is capable of modifying the structure, function or development of placental tissue, the method comprising contacting a population of induced multipotent placental cells as described in embodiment 44, a population of STB-like cells as described in embodiment 47, a population of EVT-like cells as described in embodiment 48, or placental tissue comprising such cells, with the test agent, wherein the agent is identified as a modifier when the structure, function or development of the placental tissue differs as compared to a control.

Embodiment 73. A method comprising contacting a fertilized cell, or progeny thereof, with a population of induced multipotent placental cells as described in embodiment 44, a population of STB-like cells as described in embodiment 47, or a population of EVT-like cells as described in embodiment 48 under conditions suitable for cell growth.

Embodiment 74. A method of treating a placental abnormality in a pregnant female mammal, the method comprising administering a population of induced multipotent placental cells as described in embodiment 44, a population of STB-like cells as described in embodiment 47, or a population of EVT-like cells as described in embodiment 48, to the mammal.

Embodiment 75. A population of induced multipotent placental cells as described in embodiment 44, a population of STB-like cells as described in embodiment 47, or a population of EVT-like cells as described in embodiment 47, for use in treating a placental abnormality in a pregnant female mammal.

Embodiment 76. The use of a population of induced multipotent placental cells as described in embodiment 44, a population of STB-like cells as described in embodiment 47, or a population of EVT-like cells as described in embodiment 48 to prepare a medicament for treating a placental abnormality in a pregnant female mammal.

Certain Definitions

The term “population of cells” means any number of cells greater than 1, but in certain embodiments is at least about $1\times10^3$ cells, at least about $1\times10^4$ cells, at least about $1\times10^5$ cells, at least about $1\times10^6$ cells, at least about $1\times10^7$ cells, at least about $1\times10^8$ cells, or at least about $1\times10^9$ cells.

The invention encompasses isolated or substantially purified cell compositions. In the context of the present invention, “isolated” or “purified” cell is a cell that exists apart from its native environment and is therefore not a product of nature. An “isolated” cell or a population of cells may exist in a purified form or may exist in a non-native environment such as, for example, a single cell suspension, or within a cell culturing (e.g., in vitro or ex vivo) container. For example, an “isolated” or “purified” preparation of cells, is substantially free of other cells. A population of cells that is substantially free of other cell types has less than about 20%, 10%, 5%, (by cell count) of contaminating cell types.

The term “stem cell” refers to a cell that can self-renew and is capable of giving rise to multiple different types of cells.

The term “pluripotent” describes the ability of a cell to develop into three primary germ cell layers of the early embryo. Pluripotent stem cells may be classified based on their tissue of origin: embryonic stem cells, perinatal stem cells and induced pluripotent stem cells. Pluripotent stem cells for use in the methods described herein can be obtained using methods known in the art. For example, induced pluripotent stem cells (iPSCs) may be produced using, e.g., somatic cell nuclear transfer or via nuclear reprograming of somatic cells. Further, human embryonic stem cells (hESCs) may be obtained without either destroying a human embryo or using a human embryo for an industrial or commercial purpose. For example, hESCs may be obtained by blastomere biopsy techniques.

The term “multipotent” refers to a cell that has the capacity to divide and to develop into multiple specialized cell types present in a specific tissue or organ. In certain embodiments, such a cell has the capacity to self-renew.

“Culturing” or “culturing conditions” refer to a cell culturing practice that maintain, expand and/or differentiate cells, for example, culturing cells in nutrient/growth factor supplemented cell growth medium in a cell culture container placed in a cell incubator (e.g., at 37 Celsius degree). Under culturing conditions, cells biochemical activities may approach that of a physiological level. In contrast, processing cells, digesting cells, centrifuging cells, washing cells, staining cells with an anti-surface marker agent is typically conducted under non-culturing conditions, such as contacting cells with a buffer (e.g., blocking buffer, washing buffer or staining buffer) and/or at low temperatures (e.g., 4 Celsius degree) that the cells biochemical activities are slowed and nutrient/growth factor levels are reduced or lacking compared to culturing conditions.

An “effective amount” generally means an amount which provides the desired effect (e.g., a local or systemic effect).

For example, an effective dose is an amount sufficient to affect a beneficial or desired clinical result or an amount sufficient to affect cell differentiation (e.g., in culture). Said dose could be administered in one or more administrations and could include any preselected amount of cells. The precise determination of what would be considered an effective dose may be based on factors individual to each subject, including their size, age, injury and/or disease being treated and amount of time since the injury occurred or the disease began. One skilled in the art, specifically a physician, would be able to determine the number of cells that would constitute an effective dose.

The term "therapeutically effective amount," in reference to treating a disease state/condition, refers to an amount of cells either alone or as contained in a pharmaceutical composition that is capable of having any detectable, positive effect on any symptom, aspect, or characteristics of a disease state/condition when administered as a single dose or in multiple doses. Such effect need not be absolute to be beneficial.

The terms "treat" and "treatment" refer to both therapeutic treatment and prophylactic or preventative measures, wherein the object is to prevent or decrease an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "cellular therapy" or "cell-based therapy" means the transplantation of human or animal cells to prevent, treat, or ameliorate one or more symptoms associated with a disease or disorder, such as, a placental abnormality.

As used herein, the term "engraft" or "engraftment" refers to the process of the induced multipotent placental cells as described herein, or progeny thereof, incorporating into a tissue of interest in vivo through contact with existing cells of the tissue.

The terms "subject" and "patient" may be used interchangeably and refer to an animal, such as a mammal, including non-primates (e.g., a cow, pig, horse, cat, dog, rat, or mouse) or primates (e.g., a monkey, or a human). In certain embodiments, the subject is a mammal. In certain embodiments, the mammal is a human.

The invention will now be illustrated by the following non-limiting Examples.

Figure 1B:
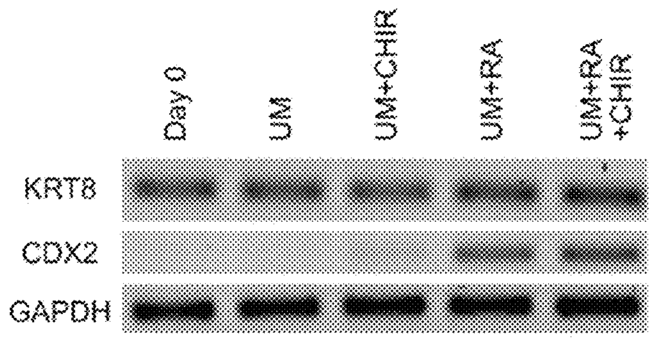
Figure 1C:
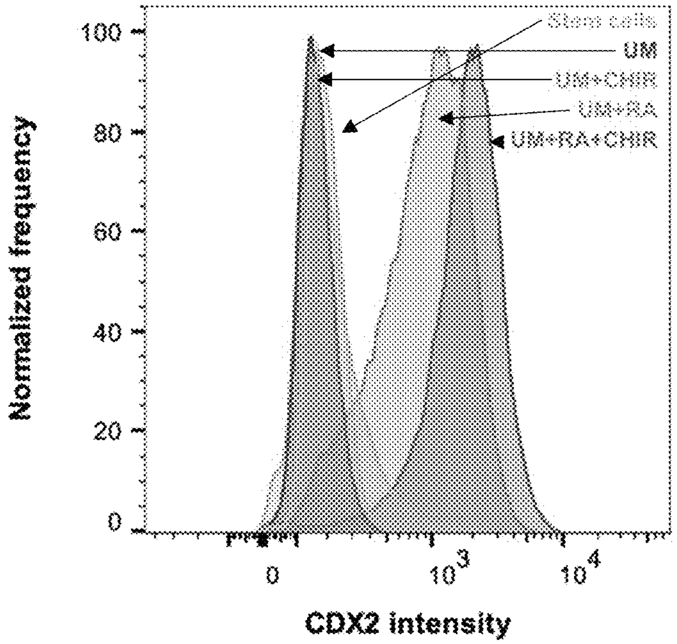
Figure 1D:
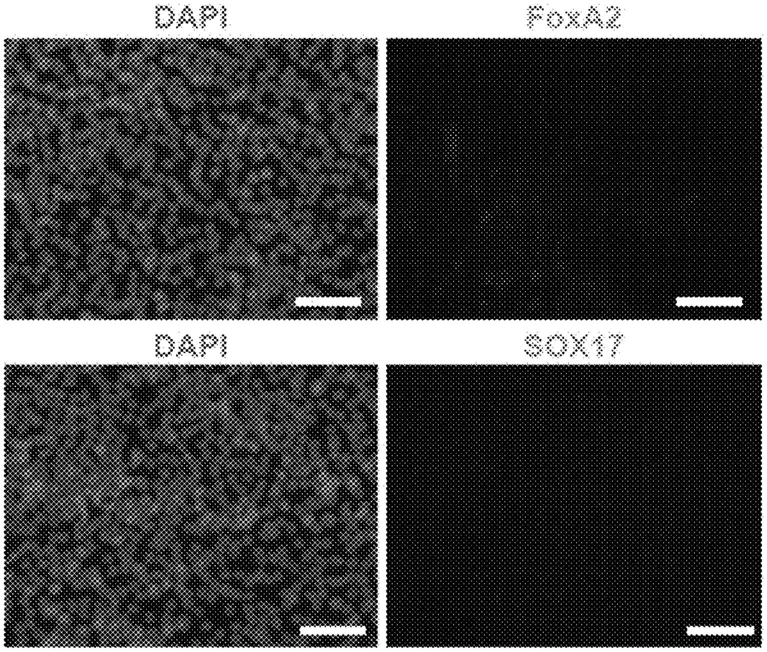
Figure 11:
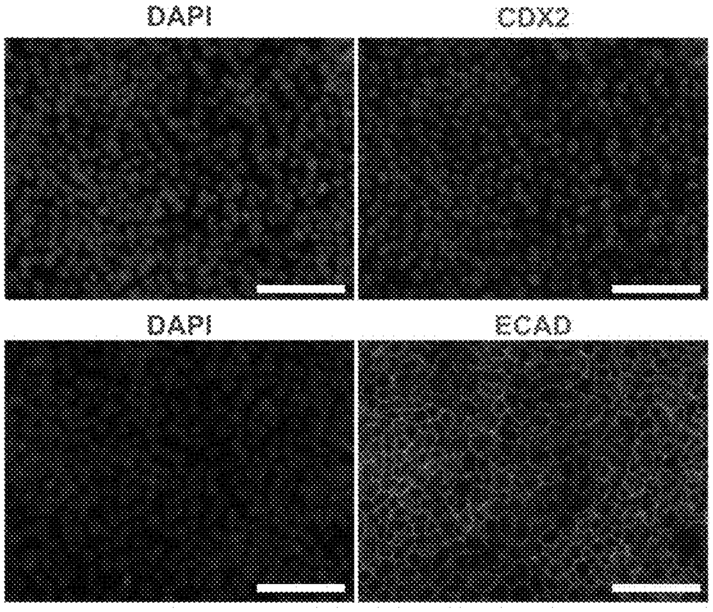
FIG. 11. Trophectoderm (CDX2) and epithelial (ECAD) protein expression evident in parallel hiPSC line. Immunocytochemistry of ACS-1024 hiPSCs treated for 5 days with RA+CHIR. Scale bars are 100 μm.

Example 1. Retinoic Acid-Induced Derivation of Trophectoderm/Trophoblast Cells from Human Induced Pluripotent Stem Cells As described herein, a rapid platform for the generation of human trophoblast cells from human induced pluripotent stem cells (hiPSCs) by upregulating retinoic acid (RA) signaling and Wnt signaling has been developed and optimized. Retinoic acid (RA)+CHIR 99021-treated cells were assessed for the established criteria defining a valid model of the trophectoderm. Specifically, immunostaining and PCR were used to track the differentiation and RNA-sequencing was used to compare this differentiation method to a BMP4-treated naïve stem cell model and post-implantation human placental tissue (Dong et al., 2020; Zhou et al., 2019). As described herein, the hiPSCs treated with RA and CHIR quickly adopt features similar to primary trophectoderm, are comparable to BMP-4-induced hPSC trophectoderm models, and meet the established criteria for trophectoderm models.

hiPSC Trophectoderm Differentiation Controlled by Interaction with Retinoic Acid and CHIR First, IMR-90-4 hiPSCs were treated with 1 μM RA (also referred herein as tretinoin) in unconditioned media (UM) (FIG. 1A) and immunostaining for pluripotency and lineage-specific markers was performed. After 5 days of RA treatment, the cells lost expression of the pluripotency marker Oct-4 and gained expression of both Keratin 18 (KRT18), an epithelial marker, and CDX2, an early marker of the human placenta (Horii et al., 2016) (FIG. 1A). However, using RA alone often gave heterogenous expression patterns of CDX2. Therefore, the addition of a Wnt signaling agonist was also examined. Specifically, 8 μM CHIR was added to the differentiation and the mRNA transcript levels of CDX2 were compared. Though low levels of CDX2 expression were seen in the UM+CHIR condition, heightened expression was evident in the condition containing RA, with even stronger expression in the UM+RA+CHIR condition (FIG. 1B). Next, to quantify the difference in protein level CDX2 expression between the various conditions, flow cytometry for CDX2 was performed. The condition with the highest overall expression contained both RA and CHIR, whereas RA alone resulted in lower, more heterogenous CDX2 expression (FIG. 1C). In particular, the addition of 8 μM CHIR to the RA-containing medium increased expression of CDX2 compared to RA-only conditions (median expression intensities of 1988±68 vs. 1348±42 respectively, $p<0.001$) and resulted in more uniform CDX2 expression compared to conditions containing RA alone (as measured by the inter-quartile range (IQR) 89 vs. 119, respectively, FIGS. 1B-C; see also, FIG. 3). CDX2 expression was also observed with RA+CHIR treatment of the ACS-1024 hiPSC line, demonstrating that this result is not cell line specific (FIG. 11). Finally, although CDX2 expression is commonly implicated in development of hindgut endoderm (Gao, White, & Kaestner, 2009; Guo, Funakoshi, Lee, Kong, & Lynch, 2010; N. Kumar et al., 2019), definitive endoderm markers FoxA2 and SOX17 were absent from cells treated for 5 days with RA+CHIR, confirming CDX2 upregulation independent of endoderm lineage (FIG. 1D).

Figure 1E:
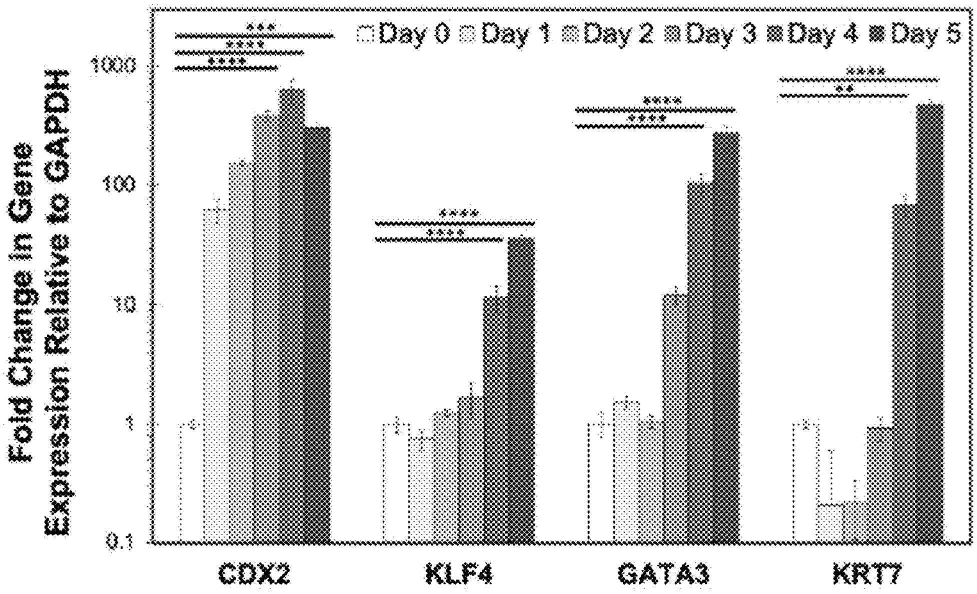
Figure 1F:
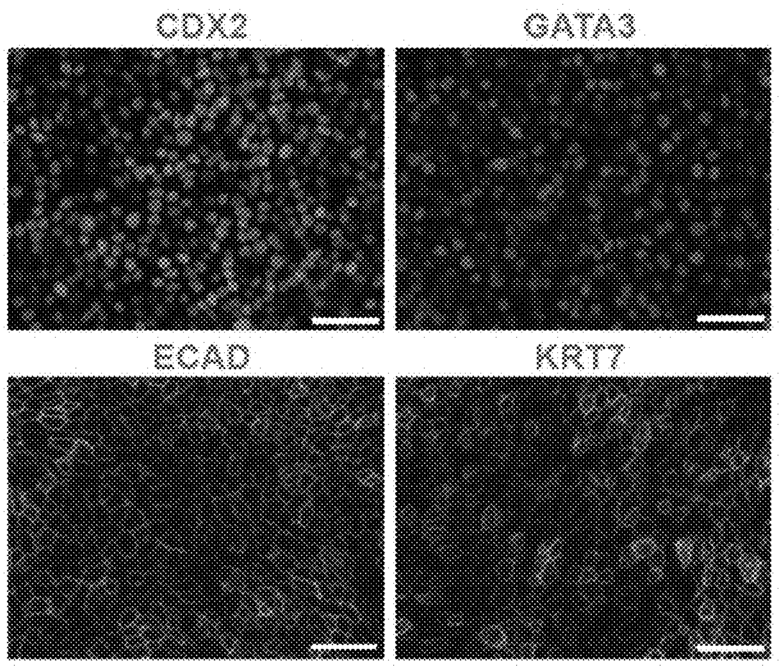
Figure 1G:
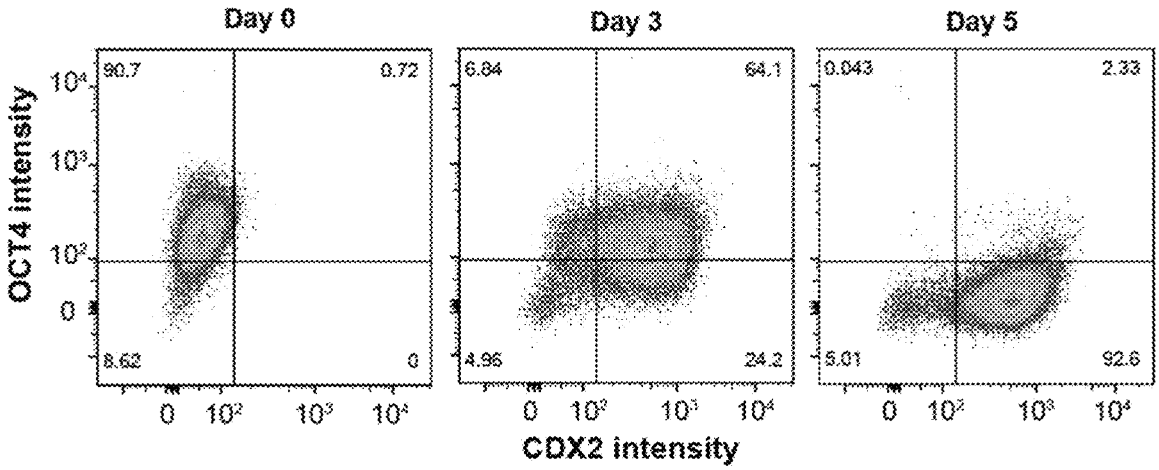
Figure 1H:
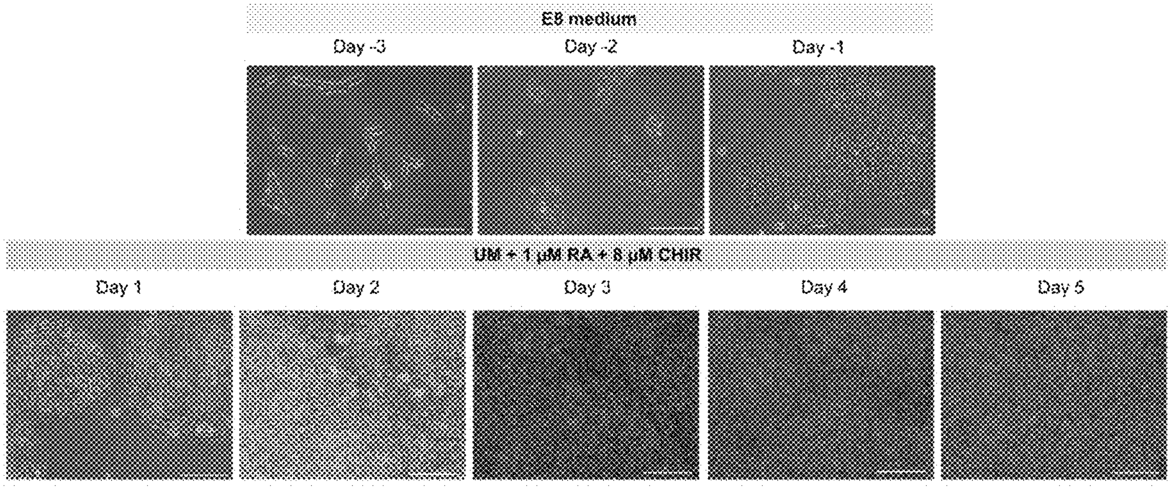

Temporal Analysis Reveals Delayed Emergence of Trophectoderm-Specific Proteins/Markers The temporal dynamics of the differentiation process was explored next. It is known that primary human trophoblast cells co-expresses lineage-specific transcription factors Oct-4 and CDX2 (Horii et al., 2016). Using flow cytometry, we saw emergence of a $CDX2^+/Oct\text{-}4^+$ population after 3 days of incubation in RA+CHIR, which transitioned to $CDX2^+/Oct\text{-}4^-$ by day 5 (FIG. 1G). Loss of CDX2 expression was observed by day 7 of treatment, so all subsequent analyses were performed at day 5 (see, e.g., Example 2, FIG. 9). The temporal dynamics of known trophectoderm markers were also analyzed using qRT-PCR. Along with upregulation of CDX2, significant upregulation of trophectoderm transcription factors KLF4 and GATA3 and of the trophectoderm-specific Keratin 7 (KRT7) (Lee et al., 2016; Li, Kurosawa, & Iwata, 2019) was observed by days 4 and 5 of the differentiation (FIG. 1E). The protein level expression of E-cadherin, GATA3, and Keratin 7 in cells expressing CDX2 was also confirmed with immunostaining, indicating an epithelial trophectodermal cell type (FIG. 1F). Morphological analysis of the cells using phase contrast imaging shows expansion of small (~100 to 200 μm, prior to addition of induction media, Day −1) pluripotent stem cell colonies to epithelial cell colonies that merge together over the course of the 5-day incubation with UM+RA+CHIR (FIG. 1H). By day 5, the cells form a confluent monolayer and display polygonal morphology with tight cell-to-cell interactions, characteristics indicative of epithelial cells (Wang et al., 2012). To further confirm trophectoderm cell fate, we analyzed expression of microRNAs (miRNAs) from the chromosome 19 miRNA cluster, expression of which has been demonstrated to be restricted only to placental cells in adult tissues (Donker et al., 2012). qRT-PCR analysis revealed that expression of miRNAs 517a, 517b, 525-3p, and 526b-3p remain high throughout differentiation at levels consistent with that of BeWo choriocarcinoma cells (FIG. 1L).

RNA-Sequencing Shows RA+CHIR-Treated Cells have High Transcriptional Correlation with Early Primary Trophectoderm Initial Analysis To further characterize the identity of the cells generated from treatment with RA and CHIR, bulk level RNA-sequencing was performed. In an initial analysis, this data was compared with single cell RNA-sequencing data obtained from days 6 through 14 (D6-D14) post implantation human embryos (GSE109555) and an alternative stem cell differentiation method which involves BMP-4 treatment of naïve human stem cells to generate trophectoderm (GSE138762, wherein GSE138688 is a Sub Series). The BMP-4 induced differentiation dataset also includes "primed" trophectoderm stem cells (TSC) which are generated from a primed population of stem cells as opposed to naïve stem cells. After compiling and averaging the single cell data and performing normalization and batch correction on all the datasets, the overall correlation of the samples was compared. The earliest time points of the RA+CHIR differentiation were most like D8 and D10 primary cells, whereas the latest time points were most like the further differentiated STB and EVT subtypes generated from the naïve BMP-4 treated cells (FIG. 1I). An initial principal component analysis (PCA) was also performed to determine how the samples clustered and which genes were primarily responsible for the variance between samples. RA+CHIR treated cells clustered closely to the primary cells, and the temporal trajectories of the two datasets align on the PC2 axis (FIG. 1J). Finally, a list of trophoblast cell-associated genes was compiled from literature sources to determine how the datasets would cluster based only on trophoblast cell identity (Chang, Wakeland, & Parast, 2018; Du et al., 2012; Hutchins et al., 2017; Zhou et al., 2019). When trophoblast cell identity clustering was examined, it was observed that the RA+CHIR treated cells again clustered with the D8 and D10 primary cells, whereas the BMP4 induced naïve cells and subtypes were most related to D12 and D14 primary cells (FIG. 1K).

Updated Analysis

Figure 12A:
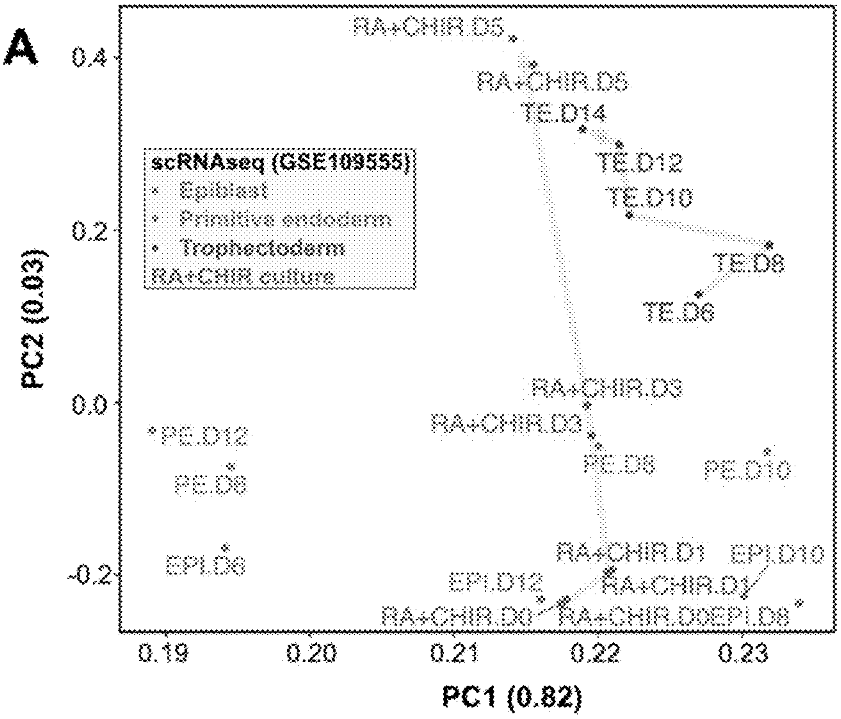
FIGS. 12A-12E.
Figure 12B:
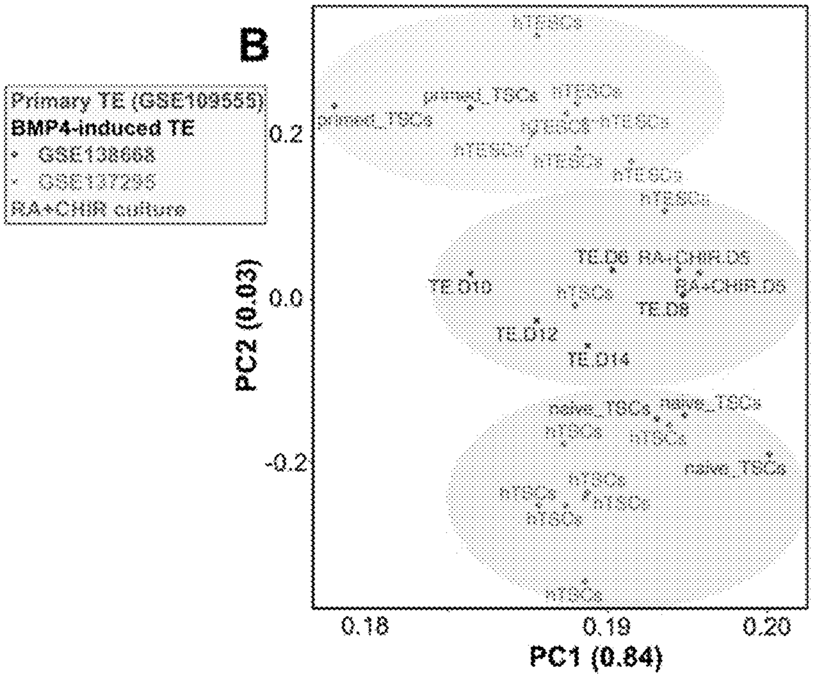
Figure 13:
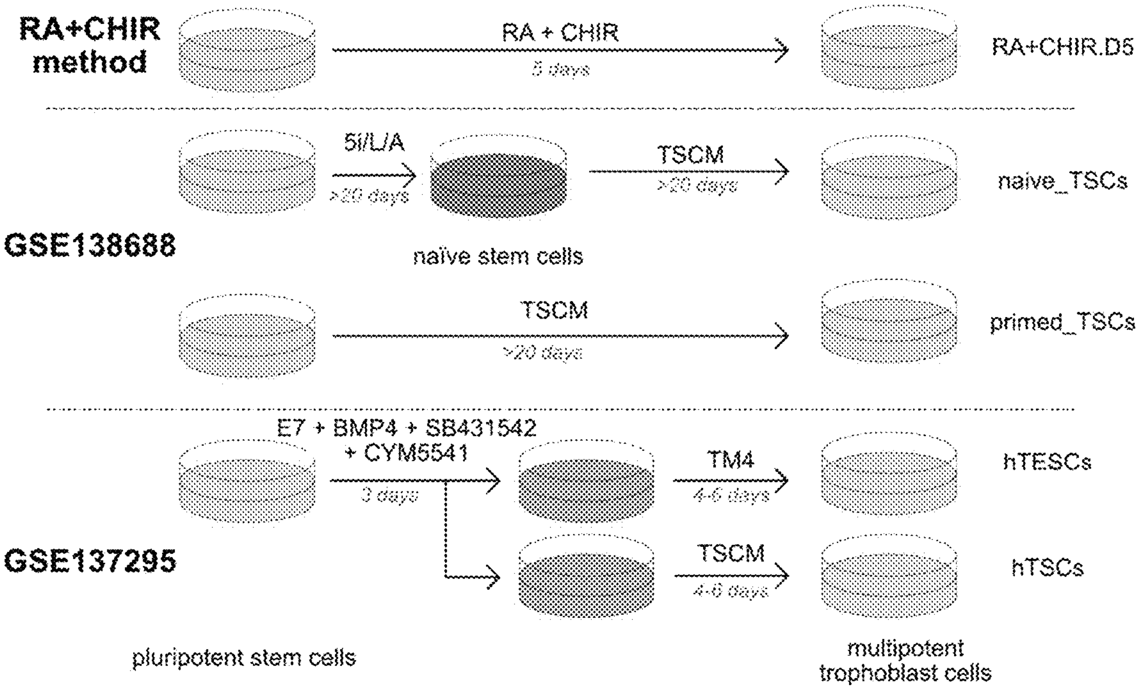
FIG. 13. Methods, reagents, and nomenclature for alternative pluripotent stem cell differentiations to trophectoderm referenced in Example 1. Schematic diagrams of differentiations, labels used in diagrams, and their corresponding GEO reference code compared in RNA-sequencing analysis. For media formulations, see Table 3.

An updated analysis was further performed, wherein the bulk level RNA-sequencing data generated from cells treated with RA and CHIR was compared to single cell RNA-sequencing data obtained from human embryos on days 6 through 14 (D6-D14) of post-implantation (GSE109555) (Zhou et al., 2019) and two alternative differentiation methods which involved BMP-4 treatment of hPSCs (GSE138762 and GSE137295) (Dong et al., 2020; Mischler et al., 2021). The GSE138762 dataset, wherein GSE138688 is a SubSeries, included both naïve and primed trophoblast stem cells (TSCs) that were generated from BMP-4 treatment of either a naïve or primed population of stem cells, respectively. The GSE137295 dataset included human trophoblast stem cells (hTSCs), similar to BMP-4-induced naïve TSCs, and hTESCs (FIG. 13 and Table 3). An updated principal component analysis (PCA) was performed to determine how the RA+CHIR-treated cell samples clustered relative to primitive endoderm (PE), epiblast (EPI), and trophectoderm (TE) transcript samples isolated from early human embryos. RA+CHIR-treated cells clustered close to EPI cells at early time points (D0 and D1), but by days 3 and 5, the RA+CHIR cells develop a positive PC2 signature, akin to the TE samples (FIG. 12A and Table 4). Next, the RA+CHIR method was compared to two other differentiation protocols to determine how close the various differentiated cell populations cluster to primary trophectoderm. RA+CHIR cells fell in the same cluster as primary trophectoderm when analyzed using k-means clustering, comparable to other differentiation methods (FIG. 12B and Table 5).

Figure 12C:
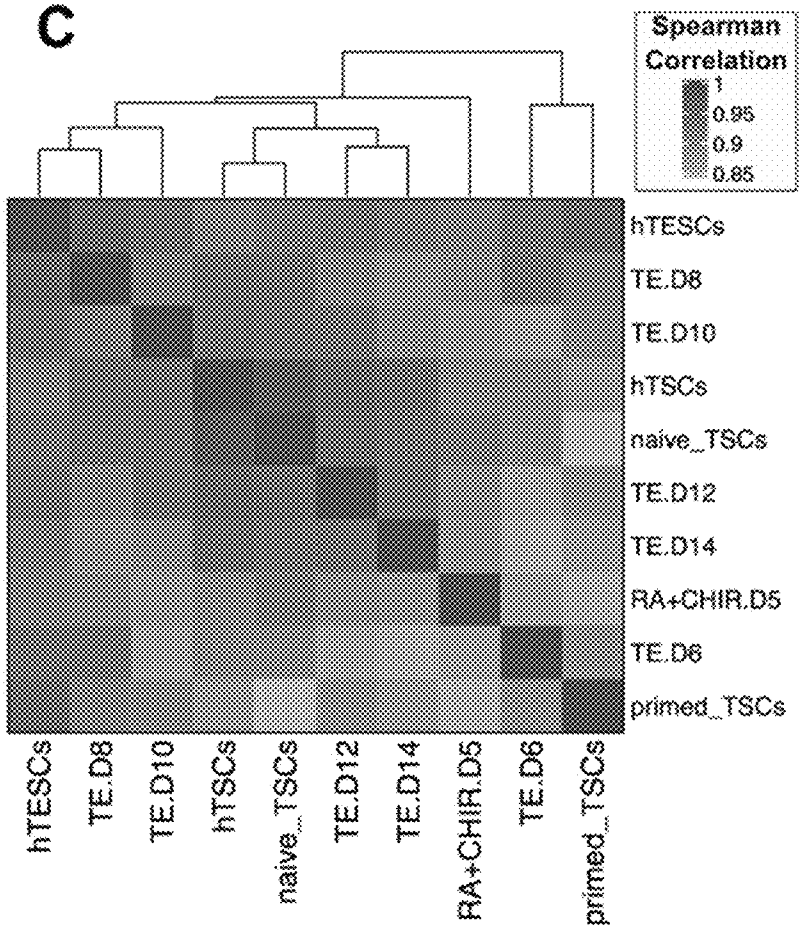

Furthermore, the Spearman correlation of the primary and differentiated trophectoderm samples was calculated. Day 5 RA+CHIR cells clustered separately from day 6 primary TE and primed TSCs and more closely with other stem cell-derived methods and days 8-14 primary TE cells (FIG. 12C). To compare the trophectoderm phenotype specifically, a list of trophoblast cell-associated genes from literature sources was compiled (Chang et al., 2018; Du et al., 2012; Hutchins et al., 2017; Zhou et al., 2019). When trophoblast cell identity clustering was examined, it was observed that day 5 RA+CHIR-treated cells clustered with the day 6 and day 8 primary TE cells and hTESCs, whereas the TSCs were most related to day 10-14 primary TE cells (FIG. 14). These results demonstrate an immaturity of the day 5 RA+CHIR-treated cells, which may indicate a more proliferative, stem cell-like phenotype.

Figures 12D, 12E:
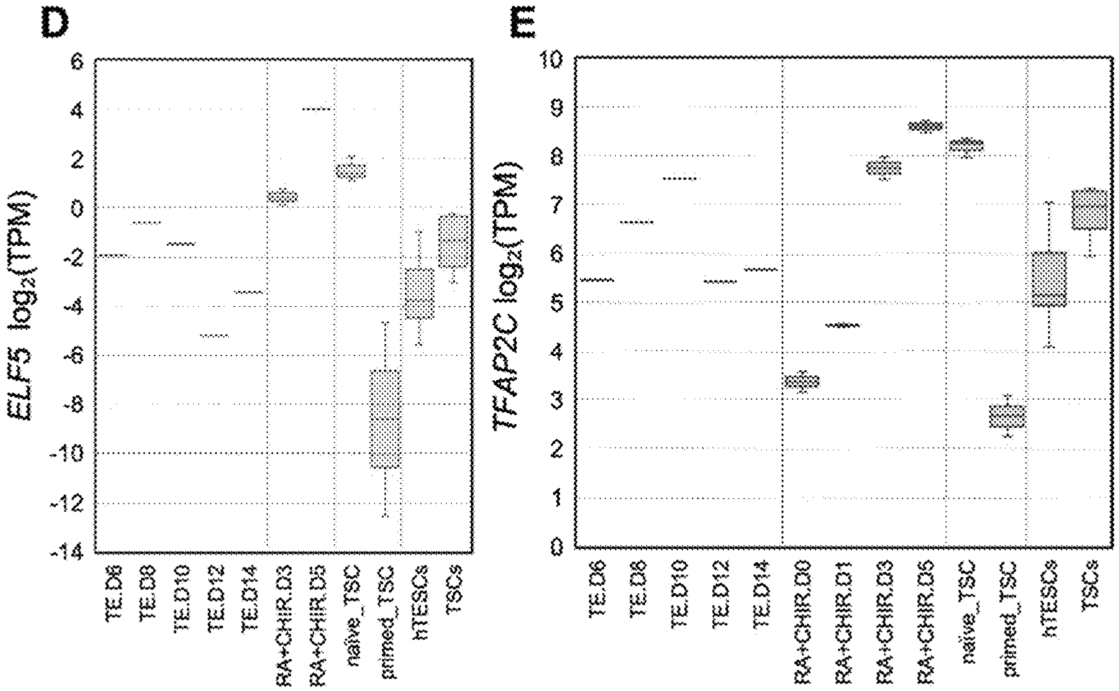

Finally, the expression levels of two genes strongly implicated in human trophectoderm development were examined: ELF5 and TFAP2C (Lee et al., 2016). An increase in expression of ELF5 was observed between days 3 and 5 in the RA+CHIR samples, which is consistent with the increase seen in day 8 primary trophectoderm and also the levels observed in BMP-4-derived models (FIG. 12D). Similarly, in day 0 through day 5 RA+CHIR an increase in expression of TFAP2C was observed, which was highly expressed by day 10 in primary trophectoderm and BMP-4-derived models (FIG. 12E). Taken together, these data demonstrate that cells generated from treatment with RA+CHIR follow the same temporal transcriptional profile as days 6-10 primary trophectoderm and express ELF5 and TFAP2C transcript levels similar to other stem cell-derived models of the placenta.

Trophoblast Cell Subtypes Show Functional Phenotypes

Figure 2C:
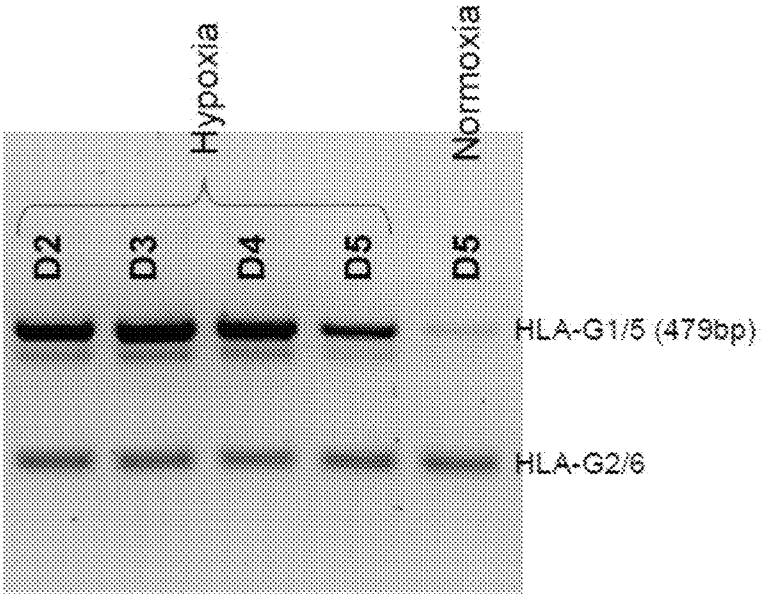
Figure 2D:
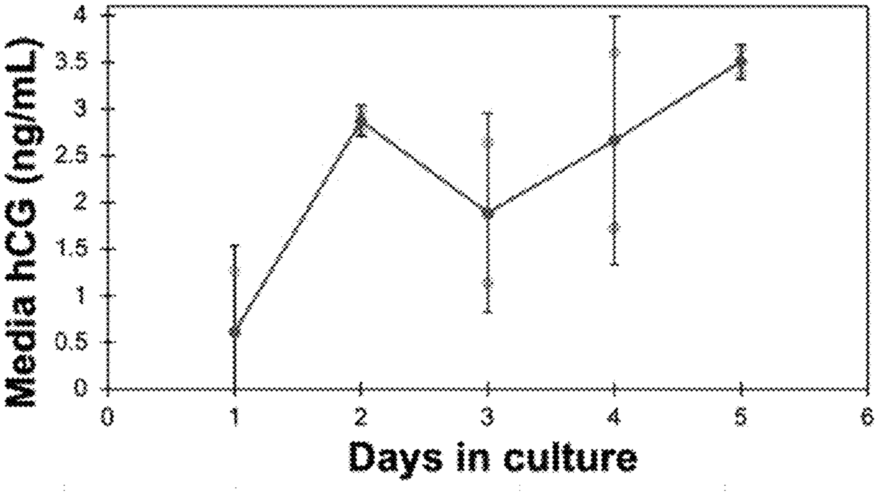
Figure 2E:
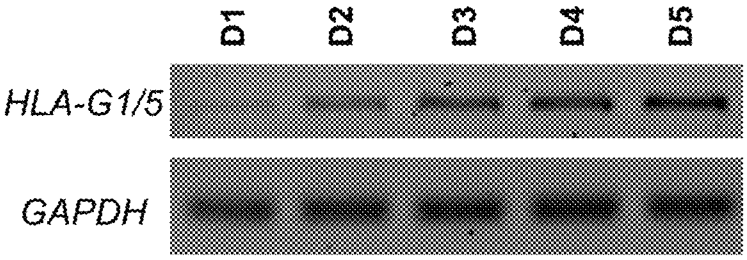

To determine if the RA+CHIR treated cells had potential for further differentiation to functional cells consistent with primary trophoblast cells, the day 5 RA+CHIR cells were subcultured and then kept in either normoxia (20% $O_2$) or hypoxia (~2% $O_2$) for a period of 5 days. Cells in normoxia were expected to acquire STB-like features, such as hCG expression and multinucleation, whereas cells in hypoxia were expected to acquire EVT-like features, including proliferation, mesenchymal gene expression, and HLA-G1 expression (Horii et al., 2016) (see, FIG. 2A). As expected, a dramatic reduction in CDX2 expression in both the STB-like and EVT-like cells was seen, which is consistent with reports that CDX2 expression is lost as trophoblast cells differentiate (Haider et al., 2018; Horii et al., 2016) (FIG. 2A). The emergence of multinucleated cells was also observed in cells cultured in normoxic conditions, evident by multiple nuclei residing inside a cell membrane labelled with E-cadherin (FIG. 2A, STB-like, bottom). Cells cultured in hypoxia had an increased number of $Ki67^+$ cells, an indication they were more proliferative than those cultured in normoxia (FIG. 2A, EVT-like, middle). A hallmark characteristic of EVT cell differentiation is the transition from an epithelial cell type to a mesenchymal cell type (EMT) as they invade the uterine wall (Du et al., 2012; E. Davies et al., 2016). To characterize the EVT-like cells, we performed qRT-PCR to look at the expression of epithelial and mesenchymal associated genes. qRT-PCR results demonstrate upregulation of transcripts for matrix metallopeptidase 2 (MMP2) and a smooth muscle actin (ACTA2) (more than 10-fold upregulated as compared to day 5 RA+CHIR treated cells) during hypoxia treatment, both associated with mesenchymal cells. Thus, gene expression analysis indicated evidence of EMT in hypoxia treated cells. Expression of epithelial associated genes TJP1 and OCLN remained relatively flat, with fold changes around 1 when compared to day 5 RA+CHIR treated cells (FIG. 2B). Furthermore, EVT cells are known to express the membrane-bound isoform of HLA-G, HLA-G1/5, whereas STB cells express no HLA class I molecules (Apps et al., 2009; Lee et al., 2016). As shown in FIG. 2C, high transcript level expression of HLA-G1/5 was seen in EVT-like cells maintained in hypoxia and low expression in STB-like cells maintained in normoxia (see also, FIG. 2E showing an increase in transcript level expression of HLA-G1/5 in EVT-like cells differentiated in hypoxia). Finally, conditioned media from the STB-like cells was analyzed for the placental hormone human chorionic gonadotropin (hCG), and detectable concentrations (3.5±±0.2 ng/mL) were found in the media following 5 days of culture (FIG. 2D). Though hCG in conditioned media was consistently detected, the value varied significantly across independent differentiations.

This data demonstrate functional trophoblast cell phenotypes of RA+CHIR treated cells, as well as the ability to derive cell populations with features of trophoblast cell subtypes from RA-CHIR treated cells, providing further evidence that these cells can be used to model functional aspects of the placenta.

Discussion

In this study, a simple method for generation of human trophoblast cells from hiPSCs is described, which uses two small molecules: RA and CHIR. RA and CHIR synergistically upregulated CDX2 and resulted in a population of cells that had a high degree of transcriptional similarity to D8-D10 primary trophectoderm. Following subculture, RA+CHIR treated cells developed characteristics akin to those of trophoblast cell subtype cells: hCG secretion in STB-like cells and HLA-G expression in EVT-like cells.

Development of a simple, relevant model of the placenta will lead to improved understanding of the formation of the trophectoderm and subsequent trophoblast cell types. Knowledge of this critical process has largely been hindered by regulations understandably protecting early fetal tissue, but stem cell-derived models have allowed us to make strides in this area. However, many of the initial BMP4-induced models have been debated in the field and can take weeks to generate. Specifically they have been critiqued based on low expression of ELF5 compared to primary trophectoderm and lack of HLA-G expression (Lee et al., 2016). BMP-4 treatment of naïve stem cells rescued some of these key features, but BMP-4-derived functional cells can take weeks to generate or involve treatment with multiple interacting small molecules and growth factors (Dong et al., 2020; Mischler et al., 2021). We assessed four criteria, which are based on those outlined by experts in the field for high fidelity models of the trophectoderm: 1) expression of ELF5 (to indirectly evaluate hypomethylation of the ELF5 promoter region); 2) C19MC miRNA expression; 3) KRT7, TFAP2C, and GATA3 expression; and 4) HLA-G expression (Lee et al., 2016). The model described herein fulfilled these established criteria and generated trophoblast-like cells with quality similar to other stem cell methods in just 5 days of treatment. In particular, this model generates trophoblast cells in 8 days and functional cells in 13 days, which outpaces other methods. Furthermore, the use of small molecules as opposed to growth factors minimizes costs and prevents variability in output. These improvements are important for performing experiments at scale. This facile trophectoderm model could be used as a model to, e.g., predict trophectoderm responses in disease states or in response to drug administration or to further our understanding of placentation.

Material and Methods

Stem Cell Culture

Human induced pluripotent stem cells (iPS(IMR90)-4, WiCell) were maintained on hESC qualified Matrigel (Corning), Vitronectin XF (Stem Cell Tech) or Cultrex (R&D Systems) in TeSR-E8 or mTeSR Plus (Stem Cell Tech) in a 37° C. incubator with 5% $CO_2$. Stem cells were passaged at 70% confluence using ReLeSR (Stem Cell Tech) as the manufacturer describes. Cells were tested monthly for *mycoplasma* contamination using Mycoalert (Lonza) and were tested for normal karyotype using G-banding analysis. Only cells from passages 40-60 were used for experiments.

Differentiation to Trophoblast Cells

For differentiation, 70% confluent stem cells were rinsed with DPBS (Gibco) and pre-warmed Accutase was added to the wells. Cells were then placed at 37° C. for 5-7 minutes. Following incubation, cells were removed from the well with a p1000 pipette. The cells in Accutase solution were then added to a conical tube containing an equal volume of fresh media and spun down at 200×g for 5 minutes. The cells were then resuspended and seeded on Matrigel-coated plates at 6,000 cells/$cm^2$ in TeSR-E8 or mTeSR Plus with 5 μM ROCK inhibitor (Y-27632, Stem Cell Tech). Cells were maintained in E8 or mTeSR Plus for two more days, and then the medium was changed to unconditioned medium (UM): DMEM/F12 with 20% Knockout serum replacement, MEM non-essential amino acids (1×), GlutaMAX (lx, Life Tech), and 0.1 mM β-mercaptoethanol (Sigma), containing 1 μM retinoic acid (RA, Sigma) and 8 CHIR 99021 (Tocris). RA and/or CHIR were excluded in control experiments (FIG. 1), as described. Cell culture media was changed daily for five days. The induced multipotent placental cells produced by this method are termed iMPC1 cells (also referred herein, as iMPC1-D5 cells). As described herein, the cells may alternatively be exposed to RA+CHIR for 3 or 4 days. For example, iMPC1-D3 and iMPC1-D4, may also be produced wherein the cells are exposed to RA+CHIR for 3 and 4 days, respectively.

For further differentiation to STB and EVT subtypes, cells maintained in UM with RA and CHIR were subcultured using Accutase as previously described above. Cells were seeded at 10,000 cells/$cm^2$ on Matrigel coated plates in UM with 5 μM ROCK inhibitor for 24 hours. For STB specification, cells were maintained in UM with 20% $O_2$ for five days, and for EVT, cells were maintained in UM under hypoxic conditions (1-2% $O_2$) for five days. The STB-like and EVT-like cells produced by this method are termed iSTBL1 cells and iEVTL1 cells, respectively. The iSTBL1 and iEVTL1 cells remain viable in UM culture once differentiated up to 7 days post seeding (likely longer).

For maintenance, the induced multipotent placental cells were further cultured in UM that lacked RA and CHIR (DMEM/F12 with 20% Knockout serum replacement, MEM non-essential amino acids (1×), GlutaMAX (1×, Life Tech), and 0.1 mM β-mercaptoethanol (Sigma)). Using this media, the cells were able to be maintained for two passages past the initial differentiation before proliferative potential was lost.

Immunostaining

For immunocytochemistry analysis, cells were rinsed 2× with PBS and then fixed for 10 minutes with 4% paraformaldehyde (PFA) at room temperature. Following 3×5-minute washes in PBS, cells were blocked in PBSGT-PBS with 5% goat serum and 0.3% Triton-X—for 1 hour. Primary antibodies (Table 1A) were diluted into PBSGT and incubated on cells overnight at 4° C. Cells were washed 3× in PBST for 15 minutes, and then secondary antibodies (Table 1B) were diluted 1:500 in PBSGT and incubated on the cells for 1 hour at room temperature. Following a 10-minute PBS wash, cells were incubated with a DAPI solution for 10 minutes. Another 10-minute PBS wash was performed before the cells were imaged on an EVOS microscope.

Flow Cytometry

Cells were rinsed 2× with PBS and then pre-warmed Accutase was added to the wells. The well plates were incubated at 37° C. for 5-7 minutes, until cells visibly detached. The supernatant was pipetted up and down to dislodge remaining cells, and then the supernatant was diluted 2-fold with spent media into a conical tube. Cells were spun down at 200×g for 5 minutes. The supernatant was aspirated, and the cells were resuspended in 1 mL 4% PFA for 10 minutes at room temperature. Cells were then spun down at 200×g for 5 minutes to remove the PFA and incubated with ice-cold 90% methanol for 30 minutes on ice. Cells were distributed to 200,000 cells per tube and vortexed with 3 mL FACS buffer (PBS+2% FBS+0.1% TritonX-100). The cells were spun down at 240×g for 5 minutes, followed by decanting the supernatant. For primary antibody incubation, 50 μL FACS buffer containing primary antibody (Table 1A) was added to the cells and then incubated overnight at 4° C. Following primary antibody incubation, cells were vortexed with 3 mL FACS buffer and then spun down at 240×g for 5 minutes. After decanting the supernatant, secondary antibody (Table 1B) was diluted 1:500 in FACS buffer and 50 μL was added to the cells for 30 minutes at room temperature. Cells were then vortexed with 3 mL FACS buffer and spun down at 240×g for 5 minutes. Following decanting of the supernatant, 300 mL FACS buffer was used to resuspend the cells and transfer them to a FACS tube. Cells were kept in the dark and on ice until analysis was performed on a BD LSR II H4710. At least 50,000 single cells per sample were collected, and analysis was performed in FlowJo. Expression values were plotted on a bi-exponential axis. Plots shown are representative of a single independent replicate, but medians and standard deviations were calculated from three independent replicates.

Enzyme-Linked Immunosorbent Assays (ELISA)

Media conditioned on STB-like cells was collected and immediately stored at −80° C. prior to analysis. Levels of hCG were quantified in duplicate using hCG ELISA Kit (Abnova) as the manufacturer recommends. Final fluorescence readings were performed on a BioTek plate reader at 450 nm.

qRT-PCR and PCR

Cell pellets were collected and lysed using QiaShredder columns (Qiagen). RNA was isolated using the RNeasy Mini Kit (Qiagen) as the manufacturer recommends, including incubation with DNase I (RNAse-free DNase Set, Qiagen). Collected RNA was quantified using a NanoDrop. Reverse transcription was performed on 1000 ng RNA using the Omni script RT Kit (Qiagen). RNA with Oligo-dT primer (Life Tech) was denatured for 5 minutes at 65° C. before the remaining elements were added and incubated at 37° C. for 1 hour. Quantitative real time PCR (qRT-PCR) was performed using iTaq Universal SYBR Green Supermix (Bio Rad) as the manufacturer recommends. Primers (Table 2) were added at 250 nM each (forward and reverse). Analysis was performed on a Bio Rad CFX Connect Real-Time PCR system. GAPDH was used as a reference gene, and error was propagated using the ΔΔCt method.

PCR was performed identically as above through the reverse transcription step to generate cDNA. GoTaq Master Mix (Promega) was used for PCR per the manufacturer's instructions. Primers (Table 2) were added at 250 μM each. PCR products were visualized on a 2% agarose gel containing SYBR Safe (Thermo Fisher) after electrophoresis at 75V for 100 minutes. Gels were imaged using a ChemiDoc Touch Gel/Blot Reader (Bio Rad).

RNA-Sequencing and Analysis

RNA from two biological replicates was collected from cell pellets as previously described above using QiaShredder columns and the RNeasy Mini Kit (Qiagen). The sequencing libraries were prepared using TruSeq Stranded mRNA (Illumina) and paired-end sequencing was performed in one lane of NovaSeq 6000 SPrime (Illumina) with a read length of 50 bp (yielding ~40M reads per sample). Low quality sequences and adaptors were removed using Trimmomatic, and sequences were then mapped to the human reference genome (GRCh38.91) using STAR. FPKM files were obtained by using cufflinks, and counts per million files were obtained by using the htseq package in Python. FPKM files were converted to TPM and used for heatmaps and clustering.

Initial Analysis

To compare primary cells and those differentiated using BMP4 to our samples, FPKM files (GSE109555 and GSE138688) were obtained from the GEO database. GSE109555 contained single cell data from cells identified as human epiblast, primitive endoderm, and trophectoderm from 65 different embryos (Zhou et al., 2019). Single cell data from trophectoderm cells was pooled and averaged to compare to batch RNA-seq datasets, and expression values less than −20 were removed from all datasets. All three datasets were normalized using quantile normalization, and batch correction was performed using the ComBat package (Johnson, Li, & Rabinovic, 2007). Heatmaps and linear dimension reduction operations were carried out in R.

Updated Analysis

To compare primary cells and those differentiated using BMP-4 to our samples, FPKM files (GSE109555, GSE138688, GSE137295) were obtained from the GEO database. GSE109555 contained single-cell data from cells identified as human epiblast, primitive endoderm, and trophectoderm from 65 different embryos (Zhou et al., 2019). Single-cell data from trophectoderm cells was pooled based on cell type and averaged to compare to batch RNA-seq datasets (only samples with >20 cells/condition were included). Lowly expressed genes were set to an arbitrarily low $\log_2$(TPM) value of −20 for numerical analyses. All four datasets were normalized using quantile normalization, and batch correction was performed using the ComBat package (Johnson et al., 2007). Heatmap generation and linear dimension reduction operations were carried out in R.

Statistical Analyses

Experiments contained at least 3 biological replicates unless otherwise specified, and a representative condition was displayed where applicable. Statistical analyses were performed in GraphPad Prism software; statistical tests and p-values are denoted in figure legends where appropriate. ANOVA tests with multiple comparisons were calculated using Dunnett's multiple comparison.

Tables 1A-1B. List of antibodies used and desired dilution ratios. (Table 1A) Primary antibodies used for immunostaining analyses or flow cytometry. (Table 1B) Secondary antibodies used for immunostaining analyses or flow cytometry.

1A. Primary

| Target | Supplier (Cat#) | Dilution |
|---|---|---|
| CDX2 | Thermo (RM-2116) | 1:500 |
| Keratin 18 | Thermo (MS-142) | 1:100 |
| E-cadherin | Cell Signaling (3195) | 1:200 |

-continued

1A. Primary

| Target | Supplier (Cat#) | Dilution |
|---|---|---|
| Keratin 8 | Invitrogen (MA5-14428) | 1:100 |
| Ki67 | Cell Signaling (9129) | 1:1000 |
| Oct-4 | Santa Cruz Biotech (SC-5279) | 1:200 |
| Sox 17 | Cell Signaling (81778) | 1:3200 |
| FoxA2 | Cell Signaling (8186) | 1:400 |
| GATA-3 | Cell Signaling (5852) | 1:1600 |
| Keratin 7 | Novus (NBP1-30152) | 1:200 |

1B. Secondary (all used at 1:500 dilution)

| Target | Supplier (Cat#) |
|---|---|
| Alexa 647 goat anti-rabbit IgG (H + L) | Life Tech (A-21244) |
| Alexa 594 goat anti-rabbit IgG (H + L) | Life Tech (A-11012) |
| Alexa 488 goat anti-mouse IgG (H + L) | Life Tech (A-11001) |
| Alexa 488 goat anti-mouse IgG1 | Life Tech (A-21121) |
| Alexa 594 goat anti-mouse IgG (H + L) | Life Tech (A-11005) |
| Alexa 647 goat anti-mouse IgG1 | Life Tech (A-21240) |

TABLE 2

List of primers used for PCR or qRT-PCR analyses*.

| Target | Forward (5' - 3') | Reverse (5' - 3') |
|---|---|---|
| SMA(A. Kumar et al., 2017) (ACTA2) | GTGTGCCCCTGAAGAGCAT (SEQ ID NO: 1) | GCTGGGACATTGAAAGTCTCA (SEQ ID NO: 8) |
| HLA-G1/5 | AAGAGGAGACACGGAACACCAA (SEQ ID NO: 2) | ATCCCGCTGGCAGGTCAGTA (SEQ ID NO: 9) |
| CDX2 | GGCAGCCAAGTGAAAACCAGGA (SEQ ID NO: 3) | TTCCTCCGGATGGTGATGTAGC (SEQ ID NO: 10) |
| GAPDH | Bio-Rad (qHsaCED0038674) | |
| KRT7 (Keratin 7) | TATGAGGAGATGGCCAAATGC (SEQ ID NO: 4) | AATCTCATTCCGGGTATTCCG (SEQ ID NO: 11) |
| KRT8 | Bio-Rad (qHsaCED0038745) | |
| GATA3 | TGTGGGCTCTACTACAAGCTT (SEQ ID NO: 5) | GCTAGACATTTTTCGGTTTCTGG (SEQ ID NO: 12) |
| KLF4 | ATCAGATGCAGCCGCAAGTC (SEQ ID NO: 6) | TCCTCTGGCATGCAGGAAC (SEQ ID NO: 13) |
| CDH1 (E-cadherin) | GGCCCATTTCCTAAAAACCTGG (SEQ ID NO: 7) | TAAAGACACCAACAGGGGGT (SEQ ID NO: 14) |
| TJP1 | Bio-Rad (qHsaCID0018062) | |
| OCLN | Bio-Rad (qHsaCED0038290) | |
| CDH5 | Bio-Rad (qHsaCID0016288) | |
| MMP2 | Bio-Rad (qHsaCEP0049822) | |

*Either forward and reverse sequences or Unique ID is included.

TABLE 3

Media formulations for methods used to make cells in RNA-sequencing analysis.

| Medium | Reference | Components |
|---|---|---|
| TSCM | Okae, et al., 2018. Cell Stem Cell 22, 50-63.e6. doi.org/10.1016/j.stem.2017.11.004 | DMEM/F12, 0.1 mM 2-mercaptoethanol, 0.2% FBS, 0.5% pen-strep, 0.3% BSA, 1% ITS-X supp, 1.5 µg/mL L-ascorbic acid, 50 ng/mL EGF, 2 M CHIR99021, 0.5M A83-01, 1 µM SB431542, 0.8 mM VPA, 5 µm ROCKi |
| TM4 | Mischler, et al. 2021. J. Biol. Chern. 296. doi.org/10.1016/j.jbc.2021.100386 | TeSR-E6, 2 µM CYM5541, 0.5 µM A83-01, 25 ng/mL FGF10, 2 µM CHIR99021 |
| 5i/L/A | Theunissen, et al., 2014. Cell Stem Cell 15, 471. doi.org/10.1016/J.STEM.2014.07.002 | DMEM/F12, Neurobasal, N2 100X supp, B27 supp, LIF, IX Gluta-MAX, IX MEM NEAA , 0.1 mM 2-mercaptoethanol, 1% pen-strep, 50 mg/ml BSA Fraction V, 1 mM PD0325901, 1 mM IM-12, 0.5 mM SB590885, 1 mM WH4-023, 10 mM Y-27632, and 10 ng/mL Activin A |

TABLE 4

Top 5 genes that contribute most to each principal component (refer to FIG. 12A).

| | PC1 | PC2 |
|---|---|---|
| Positive direction | EEF1A1 | OR7E91P |
| | RPL41 | LINC00456 |
| | RPS19 | DLX6-AS1 |
| | ACTB | GUCY1A3 |
| | RPS3 | KIAA1683 |
| Negative direction | OR5212 | LINC00428 |
| | LINGO4 | CRYBBI |
| | PRKG1-AS1 | CRYBA4 |
| | OR7C1 | ZCCGC12 |
| | DMBT1 | PPP1R17 |

TABLE 5

Top 5 genes that contribute most to each principal component (refer to FIG. 12B).

| | PC1 | PC2 |
|---|---|---|
| Positive direction | FTL | RGS4 |
| | GAPDH | SOX3 |
| | TMSB10 | IRX3 |
| | RPL8 | TFAP2B |
| | RPLP0 | HOXB9 |
| Negative direction | LINC00421 | PAX4 |
| | MAPT-IT1 | MAGEA12 |
| | HOXD10 | CGB2 |
| | OR56A4 | GH2 |
| | HELT | GTSF1 |

TABLE 6

Trophectoderm-associated gene expression (TPM values) in RA + CHIR D5 samples compared to primary trophectoderm and other stem cell-derived models (see, FIG. 14). For presentation purposes, the data has been rounded to the hundredths place.

| Genes | RA.CHIR.D5 | hTESCs | TE.D8 | TE.D6 | naive_TSCs | hTSCs | TE.D14 | TE.D12 | TE.D10 | primed_TSCs |
|---|---|---|---|---|---|---|---|---|---|---|
| CLDN4 | 8.78 | 6.76 | 8.58 | 8.52 | 8.39 | 7.33 | 6.96 | 7.02 | 6.99 | 0.62 |
| KRT7 | 10.75 | 7.56 | 6.72 | 4.92 | 7.63 | 6.07 | 9.30 | 8.74 | 7.20 | NA |
| TFAP2C | 8.47 | 6.07 | 7.97 | 6.85 | 7.79 | 7.48 | 7.04 | 6.82 | 8.81 | 1.20 |
| SP6 | 10.73 | 7.05 | 8.00 | 6.20 | 8.31 | 6.83 | 5.32 | 6.60 | 8.81 | NA |
| GATA3 | 9.65 | 5.65 | 7.62 | 7.07 | 7.86 | 6.95 | 6.49 | 6.07 | 7.24 | 0.27 |
| DLX3 | 9.40 | 5.12 | 7.28 | 5.55 | 7.32 | 7.04 | 7.45 | 7.02 | 7.23 | NA |
| ADAMTS1 | 5.18 | 5.22 | 6.80 | 4.32 | 6.54 | 7.02 | 7.81 | 7.50 | 7.48 | 3.61 |
| TINAGL1 | 8.02 | 6.29 | 6.54 | 5.24 | 6.75 | 5.87 | 7.80 | 6.12 | 6.66 | NA |
| HSD17B1 | 6.25 | 3.89 | 5.09 | 5.36 | 6.50 | 6.85 | 7.52 | 6.58 | 6.79 | 3.11 |
| NR2F2 | 11.08 | 6.53 | 6.65 | 5.03 | 6.55 | 5.96 | 2.63 | 2.39 | 4.20 | 6.68 |
| SLC7A2 | 5.89 | 5.30 | 7.05 | 7.06 | 6.19 | 5.29 | 6.05 | 5.61 | 5.78 | 2.60 |
| ABCG2 | 8.84 | 4.88 | 4.79 | 5.51 | 6.36 | 5.17 | 7.67 | 7.31 | 5.68 | 0.53 |
| TFAP2A | 8.30 | 5.13 | 5.09 | 4.23 | 6.72 | 4.91 | 6.78 | 6.20 | 7.05 | 2.32 |
| WLS | 7.35 | 4.99 | 6.54 | 5.51 | 3.65 | 3.97 | 5.10 | 5.56 | 5.61 | 6.70 |
| C1orf115 | 6.13 | 2.00 | 5.29 | 4.52 | 5.52 | 6.88 | 8.23 | 7.12 | 6.16 | NA |
| MBNL3 | 6.79 | 4.33 | 5.37 | 3.68 | 6.07 | 5.15 | 5.20 | 5.48 | 6.11 | 3.00 |
| GRHL1 | 7.46 | 3.89 | 6.12 | 5.09 | 5.56 | 5.18 | 5.61 | 5.49 | 5.93 | 0.80 |
| ARHGDIB | 1.35 | 5.14 | 4.68 | 3.85 | 6.30 | 6.56 | 8.53 | 7.46 | 5.06 | 1.96 |
| DAB2 | 5.53 | 3.86 | 3.67 | 5.28 | 4.84 | 5.92 | 6.67 | 6.39 | 5.08 | 2.92 |
| RAB31 | 4.28 | 3.95 | 5.50 | 5.05 | 5.50 | 4.13 | 5.74 | 5.70 | 5.54 | 3.89 |
| TEAD1 | 3.93 | 4.25 | 5.51 | 4.95 | 4.93 | 4.55 | 5.41 | 4.86 | 5.10 | 3.92 |
| GJA5 | 0.42 | 4.07 | 7.11 | 4.03 | 6.55 | 6.98 | 7.44 | 6.28 | 5.64 | −1.39 |
| PPME1 | 3.49 | 3.63 | 5.27 | 4.81 | 4.09 | 4.45 | 5.55 | 4.84 | 4.58 | 4.27 |
| EMP2 | 5.39 | 5.27 | 4.86 | 6.60 | 3.62 | 2.99 | 1.00 | 1.25 | 2.46 | 4.95 |

TABLE 6-continued

Trophectoderm-associated gene expression (TPM values) in RA + CHIR D5 samples compared to primary trophectoderm and other stem cell-derived models (see, FIG. 14). For presentation purposes, the data has been rounded to the hundredths place.

| Genes | RA.CHIR.D5 | hTESCs | TE.D8 | TE.D6 | naive_TSCs | hTSCs | TE.D14 | TE.D12 | TE.D10 | primed_TSCs |
|---|---|---|---|---|---|---|---|---|---|---|
| MBNL2 | 5.75 | 3.14 | 3.80 | 1.12 | 3.67 | 3.44 | 5.39 | 5.05 | 5.03 | 1.21 |
| HAND1 | 10.08 | 5.73 | 4.49 | 7.52 | 6.96 | 1.03 | 1.64 | −2.77 | 1.18 | NA |
| KLF4 | 7.65 | 4.43 | 2.96 | 2.01 | 4.37 | 6.32 | 2.17 | 2.77 | 3.12 | NA |
| TPD52L1 | 3.65 | 3.56 | 4.10 | 3.82 | 3.85 | 3.30 | 3.75 | 3.92 | 3.61 | 1.85 |
| EGFR | 4.04 | 1.94 | 2.19 | 2.60 | 4.09 | 4.44 | 5.54 | 5.04 | 3.42 | 0.89 |
| PPARG | 5.66 | 2.38 | 2.98 | 1.96 | 5.05 | 3.46 | 3.21 | 2.89 | 2.34 | −1.73 |
| GCM1 | 6.93 | 1.95 | 3.07 | 0.36 | 4.60 | 4.77 | 3.13 | 2.54 | 3.73 | −3.59 |
| ZFHX3 | 3.85 | 1.60 | 2.85 | 1.63 | 2.47 | 1.65 | 1.93 | 2.07 | 2.93 | 1.78 |
| CXADR | 1.74 | 4.44 | 1.23 | 4.13 | 2.95 | 1.34 | −0.47 | 0.70 | 1.17 | 5.42 |
| ACKR2 | 5.37 | 2.02 | 0.87 | 0.67 | 3.76 | 3.58 | 3.16 | 3.21 | 1.69 | −3.29 |
| PSG4 | 5.35 | 1.07 | −1.23 | −2.72 | 3.50 | 5.20 | 6.57 | 6.40 | 2.02 | −7.90 |
| ITGA2 | 1.05 | 1.87 | 0.42 | −1.73 | 3.58 | 2.94 | 2.64 | 2.83 | 2.55 | 1.35 |
| XAGE3 | NA | −0.62 | 0.04 | −2.49 | 7.04 | 4.83 | 2.93 | 2.31 | 1.45 | NA |
| DPP4 | −4.46 | 1.94 | −0.85 | 0.13 | 5.75 | 5.94 | 2.27 | 2.34 | 0.65 | −2.58 |
| PSG5 | 3.96 | −0.50 | −1.84 | −5.47 | 3.02 | 4.14 | 6.15 | 4.97 | 1.50 | −5.96 |
| PSG3 | NA | NA | −4.23 | −4.67 | 1.89 | 4.10 | 5.79 | 5.29 | −0.27 | −8.23 |
| LAMP3 | −5.53 | 1.01 | −2.31 | −2.34 | −0.08 | 0.22 | 1.56 | 1.73 | 1.33 | −1.23 |
| PSG1 | NA | NA | −5.78 | −9.15 | 0.18 | 2.07 | 3.47 | 2.99 | −0.48 | NA |
| HAVCR1 | 5.74 | NA | −1.48 | 0.43 | 2.47 | 1.42 | −5.72 | −6.63 | −3.75 | NA |
| PSG8 | NA | NA | −8.82 | NA | −1.63 | −0.40 | 0.94 | 0.22 | −2.26 | NA |
| PSG9 | NA | NA | −8.58 | −4.92 | −0.37 | 1.72 | 4.05 | 3.75 | −0.13 | −8.42 |
| CDX2 | 1.55 | 4.34 | −2.16 | 3.00 | NA | −1.65 | −8.17 | −3.80 | −14.37 | NA |
| ITGB3 | NA | −3.05 | −5.60 | −11.64 | −0.95 | −0.01 | 0.53 | 0.20 | −2.18 | −6.28 |

Example 2. Evaluation of Various Conditions for the Production of RA-induced Trophectoderm Certain conditions and combinations of conditions were evaluated for their impact on the production of retinoic acid (RA)-induced multipotent placental cells (e.g., induced trophectoderm cells). In particular, the impact of CHIR-99021 on differentiation, RA concentration, seeding density, media composition, ECM, and time duration for differentiation were evaluated as described below. These experiments were performed using a representative iPSC cell line ((IMR90)-4 (WiCell)). Similar experiments as those described below may be performed to evaluate conditions for other types and lines of pluripotent stem cells. Additionally, similar experiments may be used to evaluate other conditions or combinations of conditions generally.

Results

Figure 3:
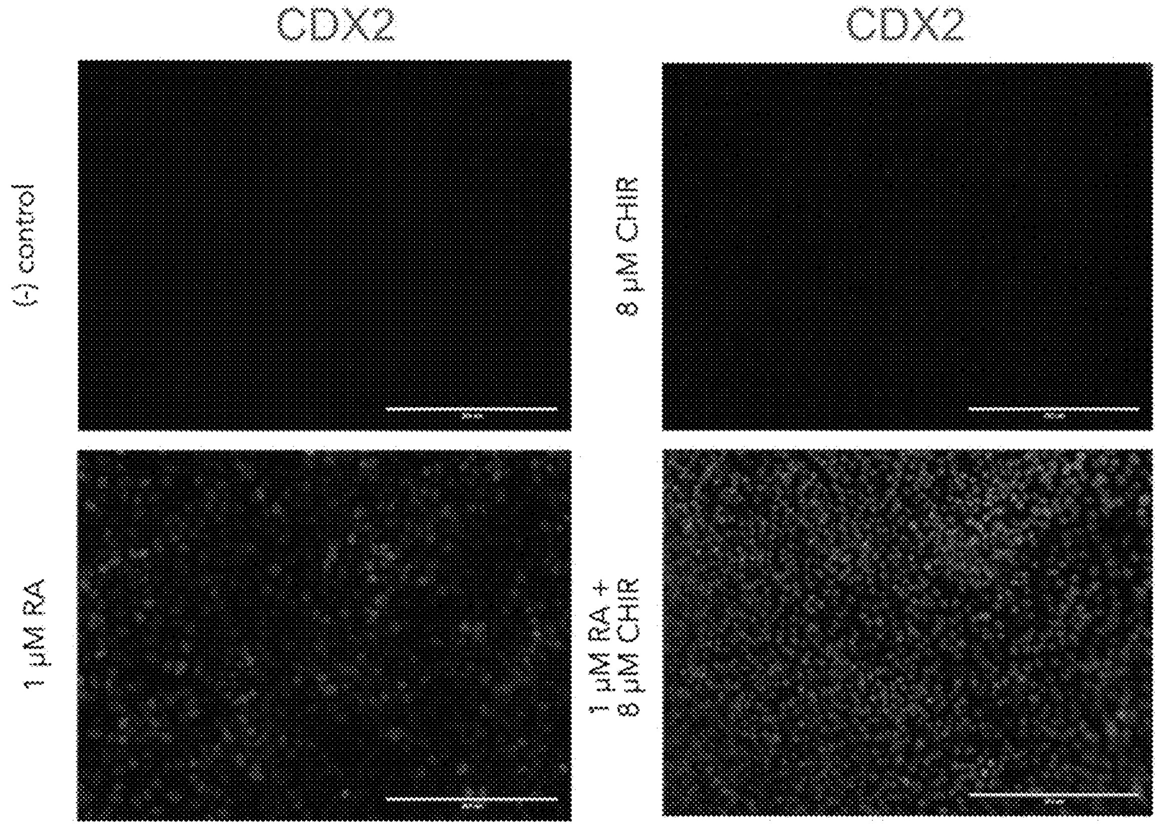
FIG. 3. RA and CHIR act in synergy to upregulate CDX2. Immunostaining images of differentiation with and without CHIR showing CDX2 expression after 5 days. The (−) control condition is UM alone. Scale bar is 200 μm.

As shown in FIG. 3, the impact of CHIR-99021 on CDX2 protein expression was evaluated. In particular, FIG. 3 shows CDX2 immunostaining images of differentiation with and without CHIR-99021 (expression after 5 days). 8 μM of CHIR-99021 was unable to induce CDX2 protein expression; however, in combination with RA there was a synergistic upregulation of CDX2.

Figure 4:
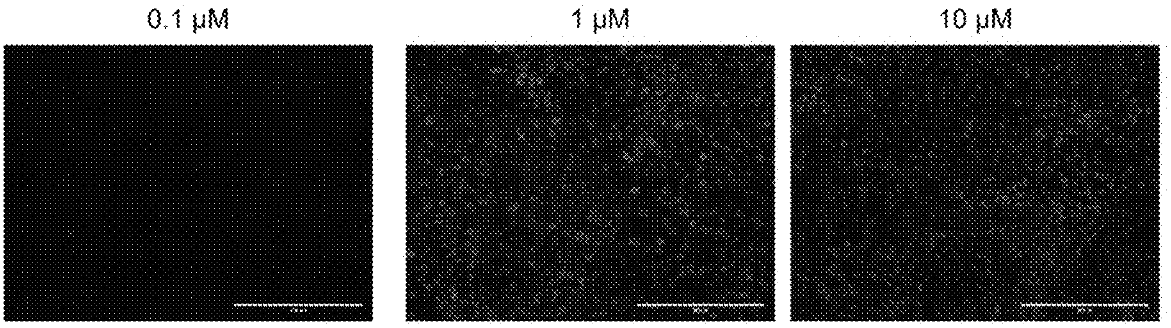
FIG. 4. Optimizing the concentration of RA needed to induce CDX2. Immunostaining images of CDX2 after 5 days incubation in UM with the labelled RA concentration. Scale bar is 200 μm.

The effect of RA concentration on the expression of CDX2 was also examined. FIG. 4 shows immunostaining images of CDX2 expression after 5 days incubation in UM having RA concentrations of 0.1 μM, 1 μM and 10 μM. The lowest concentration tested, which resulted in CDX2 expression, was 1 μM RA.

Figures 5A, 5B:
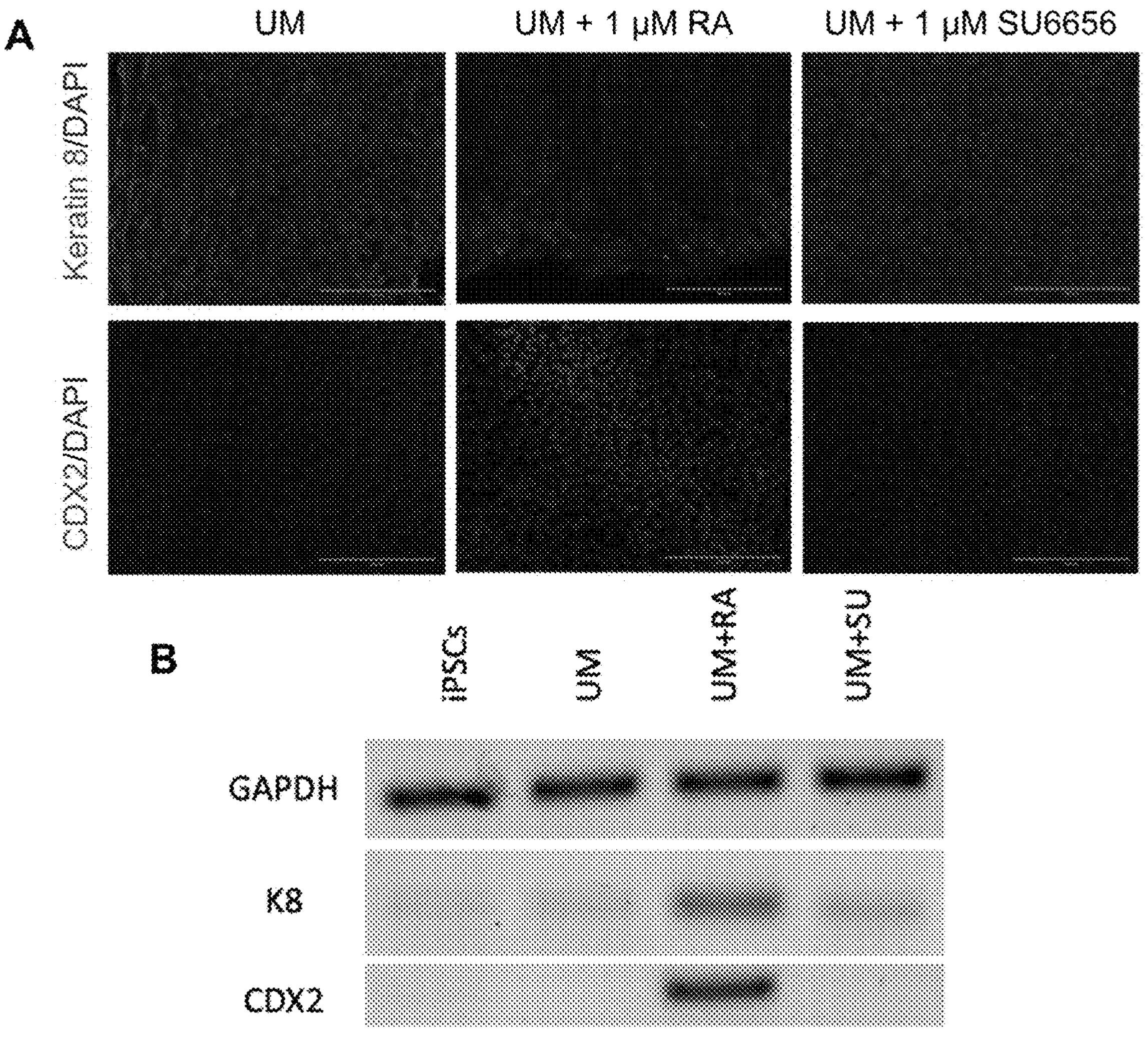
FIGS. 5A-5B. Comparing differentiation with a previously reported epithelial cell inducer (SU6656) to the RA differentiation process.

The RA differentiation process was also compared to a previously reported epithelial cell inducer, SU6656. FIG. 5A shows immunostaining images of Keratin 8 and CDX2 expression after 5 days incubation with UM, UM+1 μM RA, and UM+1 μM SU6656. Keratin 8, an epithelial marker, is expressed in all conditions, but CDX2 expression is restricted to the RA condition. FIG. 5B shows RT-PCR of mRNA isolated from stem cells (iPSCs) and from iPSCs incubated for 5-days in UM, UM+1 μM RA, and UM+1 μM SU6656. These results confirm transcript level expression of CDX2 is also restricted to the RA condition.

Figures 6A, 6B:
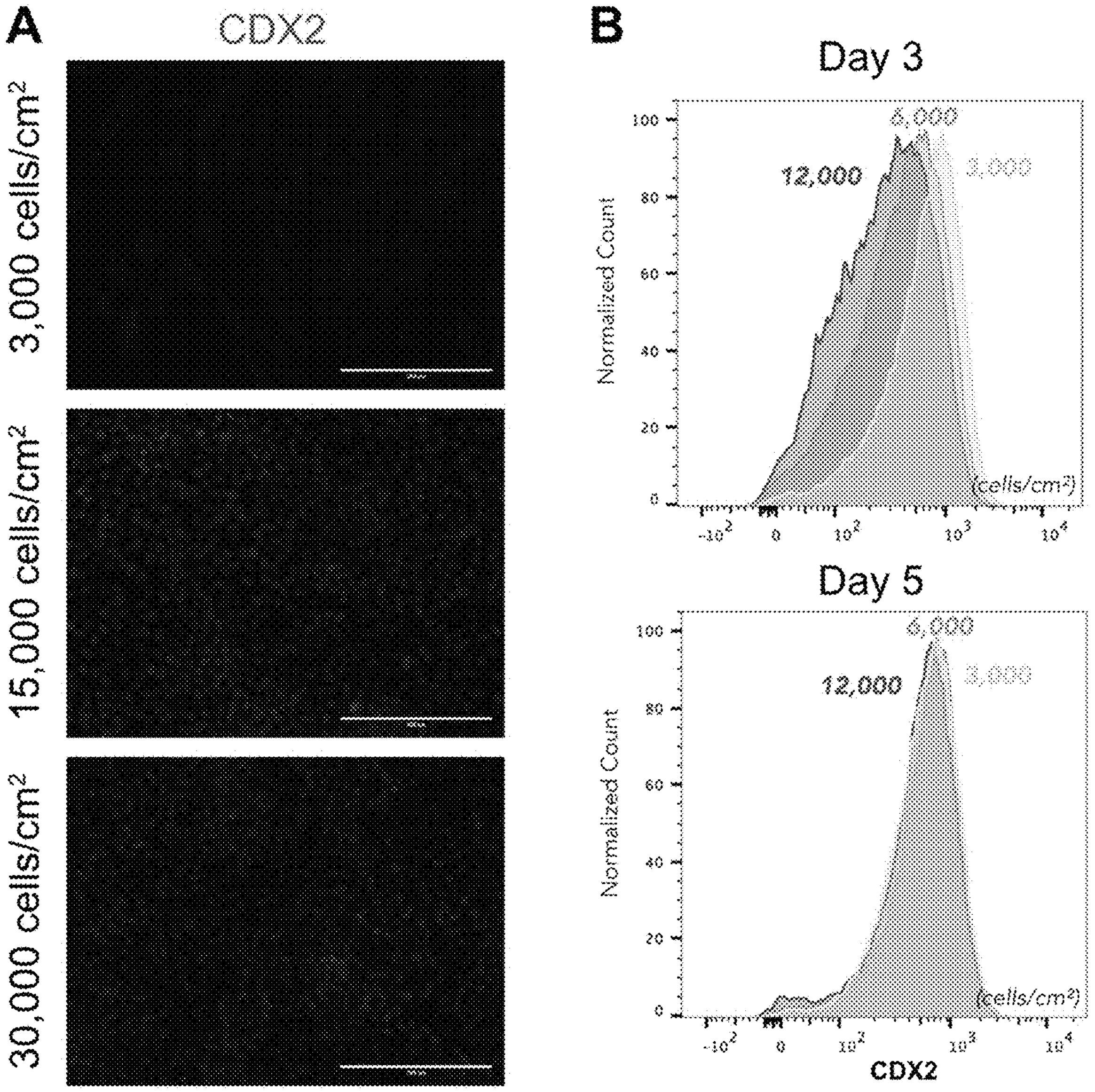
FIGS. 6A-6B. Effect of seeding density on the expression of CDX2.

The effect of seeding density on the expression of CDX2 was also evaluated (FIGS. 6A-6B). In particular, FIG. 6A shows immunostaining images of CDX2 expression of cells seeded at 3,000 cells/$cm^2$, 15,000 cells/$cm^2$, and 30,000 cells/$cm^2$ and maintained for 5 days in UM+1 μM RA. The 15,000 cells/$cm^2$ condition showed high cell yield with low amounts of overgrowth. FIG. 6B shows a flow cytometry CDX2 histogram at Day 3 or 5 of differentiation in UM+1 μM RA+8 μM CHIR for 3,000 cells/$cm^2$, 6,000 cells/$cm^2$, and 12,000 cells/$cm^2$ seeding densities. By Day 5 there was not a large difference between the 3,000 and 6,000 cells/$cm^2$ seeding densities, but the 6,000 cell/$cm^2$ condition resulted in a higher cell yield.

Figures 7A, 7B:
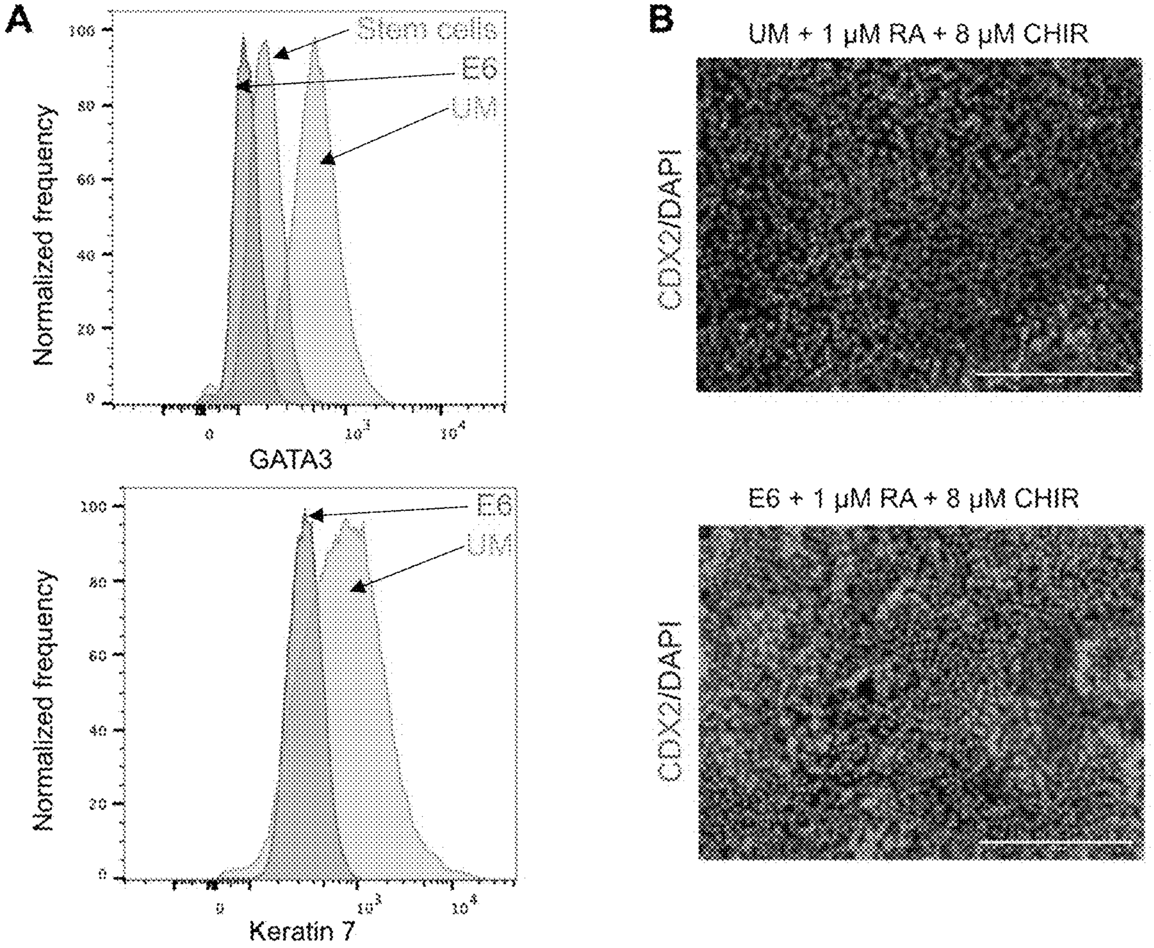
FIGS. 7A-7B. Comparison of UM with a defined, minimal medium: E6.

Two different basal medias were also compared: UM and E6, which is a defined, minimal media. FIG. 7A shows a flow cytometry histogram of GATA3 expression from undifferentiated stem cells, cells differentiated for 5 days in E6+RA+CHIR, and cells differentiated for 5 days in UM+RA+CHIR (top), as well as a flow cytometry histogram of Keratin 7 expression from cells differentiated for 5 days in E6+RA+CHIR and cells differentiated for 5 days in UM+RA+CHIR (bottom). Cells differentiated in E6 had lower expression of the trophectoderm marker GATA3 than the stem cells and cells cultured in UM. E6-differentiated cells also had lower expression of Keratin 7 than cells differentiated in UM. FIG. 7B shows immunostaining images of CDX2 expression after 5 days incubation with UM, UM+1 μM RA+8 μM CHIR-99021, and E6+1 μM RA+8 μM CHIR-99021. CDX2 expression increased in cells treated with both types of media. The results from these experiments indicated that the expression of certain trophectoderm/trophoblast cell markers was impacted by the basal media.

Figure 8:
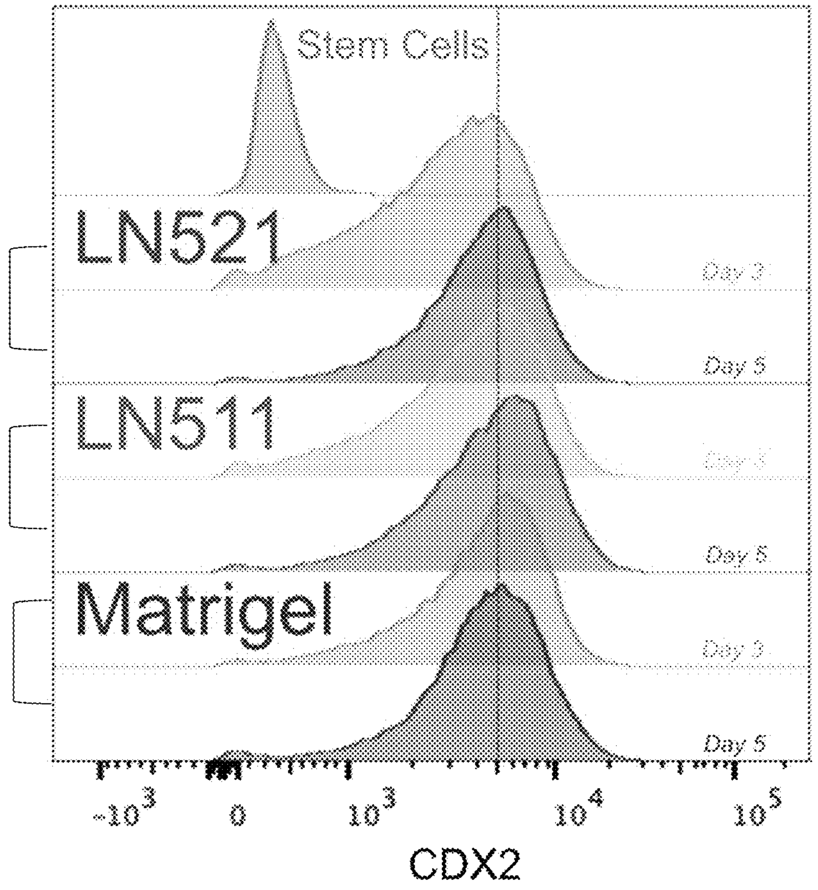
FIG. 8. Effect of extracellular matrix (ECM) coating on differentiation toward CDX2-expressing cells. Flow cytometry CDX2 histograms at Day 3 and 5 of differentiation for cells seeded on the indicated ECM protein. Vertical line at 5000 intensity units is added for clarity.

The effect of extracellular matrix (ECM) coatings on differentiation toward CDX2-expressing cells was examined. Flow cytometry CDX2 histograms at Day 3 and 5 of differentiation for cells seeded on the various ECM proteins are shown in FIG. 8. There were no significant differences between the various matrices tested: LN521, LN511 and matrigel.

Figure 9:
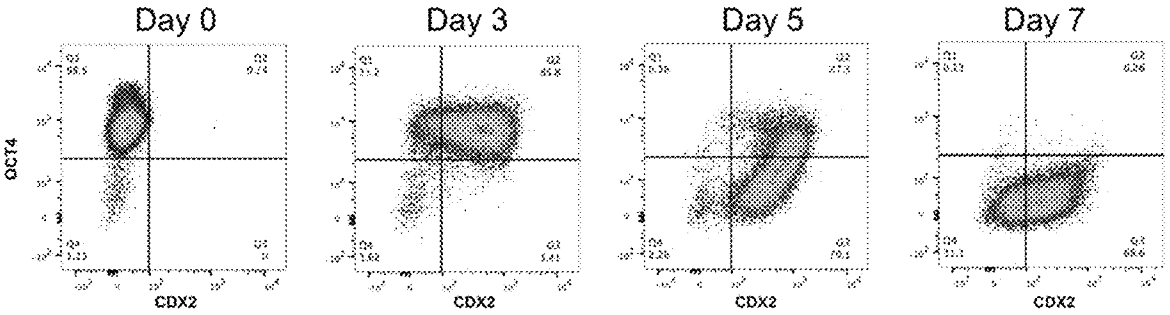
FIG. 9. Evaluation of the optimal duration of the differentiation based on Oct-4 expression (pluripotency) and CDX2 expression (trophectoderm). Five days of RA+CHIR is optimal for maximum CDX2 expression. Flow cytometry of CDX2 and Oct-4 expression for cells undergoing differentiation with RA+CHIR at various timepoints during differentiation. Numeric values in each corner are percentages of cells within quadrant.

The effect of the duration of the differentiation based on OCT4 expression (pluripotency) and CDX2 expression (trophectoderm) was investigated. Flow cytometry quadrant histograms of CDX2 and OCT4 expression at various timepoints during differentiation are shown in FIG. 9. Day 3 cells still express OCT4, indicating the cells are not fully differentiated. However, Day 7 cells show a reduction in CDX2 expression, whereas Day 5 shows a large population of OCT4 negative/CDX2 positive cells.

Transcript level expression of trophoblast cell markers was investigated following 5 days of incubation with UM, UM+CHIR, UM+RA, and UM+RA+CHIR. Compared to UM alone, FIG. 10 shows UM+CHIR compromised the expression of KLF4, GATA3, and KRT7 while still upregulating CDX2. The addition of RA alone or in combination with CHIR resulted in upregulation of trophoblast cell transcriptions CDX2, KLF4, GATA3, and KRT7 with limited difference observed between conditions with CHIR and those without.

In summary, presence of CHIR-99021, retinoic acid (RA) concentration, seeding density, and basal media all affected the differentiation of the (IMR90)-4 iPS cells toward CDX2-expressing cells. Various extracellular matrix proteins were able to support the differentiation process.

Materials and Methods

The experiments described in Example 2 were performed using materials and methods similar to those described in Example 1.

DOCUMENTS CITED IN THE EXAMPLES

Apps, R., Murphy, S. P., Fernando, R., Gardner, L., Ahad, T., & Moffett, A. (2009). Human leucocyte antigen (HLA) expression of primary trophoblast cells and placental cell lines, determined using single antigen beads to characterize allotype specificities of anti-HLA antibodies. *Immunology,* 127(1), 26-39. doi.org/10.1111/j.1365-2567.2008.03019.x Archbold, H. C., Yang, Y. X., Chen, L., & Cadigan, K. M. (2012). How do they do Wnt they do?: Regulation of transcription by the Wnt/β-catenin pathway. *Acta Physiologica,* 204(1), 74-109. doi.org/10.1111/j.1748-1716.2011.02293.x Blakeley, P., Fogarty, N. M. E., Del Valle, I., Wamaitha, S. E., Hu, T. X., Elder, K., . . . . Niakan, K. K. (2015). Defining the three cell lineages of the human blastocyst by single-cell RNA-seq, 142, 3613. doi.org/10.1242/dev.131235

Chang, C. W., Wakeland, A. K., & Parast, M. M. (2018 Jan. 1). Trophoblast lineage specification, differentiation and their regulation by oxygen tension. *Journal of Endocrinology*. NIH Public Access. doi.org/10.1530/JOE-17-0402

Clevers, H. (2006). Wnt/β-Catenin Signaling in Development and Disease. *Cell,* 127(3), 469-480. doi.org/10.1016/J.CELL.2006.10.018

Cunningham, T. J., & Duester, G. (2015). Mechanisms of retinoic acid signalling and its roles in organ and limb development. *Nature Publishing Group*. doi.org/10.1038/nrm3932

Dong, C., Beltcheva, M., Gontarz, P., Zhang, B., Popli, P., Fischer, L. A., . . . . Theunissen, T. W. (2020). Derivation of trophoblast stem cells from naïve human pluripotent stem cells. *ELife,* 9, 1-26. doi.org/10.7554/eLife.52504

Donker, R. B., Mouillet, J. F., Chu, T., Hubel, C. A., Stolz, D. B., Morelli, A. E., Sadovsky, Y., 2012. The expression profile of C19MC microRNAs in primary human trophoblast cells and exosomes. Mol. Hum. Reprod. 18, 417. doi.org/10.1093/MOLEHR/GAS013

Du, R., Sun, W., Xia, L., Zhao, A., Yu, Y., Zhao, L., . . . . Sun, S. (2012). Hypoxia-Induced Down-Regulation of microRNA-34a Promotes EMT by Targeting the Notch Signaling Pathway in Tubular Epithelial Cells. *PLOS ONE,* 7(2), e30771. doi.org/10.1371/JOURNAL.PONE.0030771

E. Davies, J., Pollheimer, J., Yong, H. E. J., Kokkinos, M. I., Kalionis, B., Knöfler, M., & Murthi, P. (2016 May 3). Epithelial-mesenchymal transition during extravillous trophoblast differentiation. *Cell Adhesion and Migration*. Taylor and Francis Inc. doi.org/10.1080/19336918.2016.1170258

Gao, N., White, P., & Kaestner, K. H. (2009). Establishment of Intestinal Identity and Epithelial-Mesenchymal Signaling by Cdx2. *Developmental Cell,* 16(4), 588-599. doi.org/10.1016/j.devcel.2009.02.010

Guo, R. J., Funakoshi, S., Lee, H. H., Kong, J., & Lynch, J. P. (2010). The intestine-specific transcription factor Cdx2 inhibits β-catenin/TCF transcriptional activity by disrupting the β-catenin-TCF protein complex. *Carcinogenesis,* 31(2), 159-166. doi.org/10.1093/carcin/bgp213

Haider, S., Meinhardt, G., Saleh, L., Kunihs, V., Gamperl, M., Kaindl, U., . . . . Knöfler, M. (2018). Self-Renewing Trophoblast Organoids Recapitulate the Developmental Program of the Early Human Placenta. *Stem Cell Reports,* 11(2), 537-551. doi.org/10.1016/j.stemcr.2018.07.004

Horii, M., Bui, T., Touma, O., Cho, H. Y., & Parast, M. M. (2019). An Improved Two-Step Protocol for Trophoblast Differentiation of Human Pluripotent Stem Cells. *Current Protocols in Stem Cell Biology,* 50(1). doi.org/10.1002/cpsc.96

Horii, M., Li, Y., Wakeland, A. K., Pizzo, D. P., Nelson, K. K., Sabatini, K., . . . . Parast, M. M. (2016). Human pluripotent stem cells as a model of trophoblast differentiation in both normal development and disease. *Proceedings of the National Academy of Sciences of the United States of America,* 113(27), E3882-E3891. doi.org/10.1073/pnas.1604747113

Hutchins, A. P., Yang, Z., Li, Y., He, F., Fu, X., Wang, X., . . . . Pei, D. (2017). Models of global gene expression define major domains of cell type and tissue identity. *Nucleic Acids Research,* 45(5), 2354-2367. doi.org/10.1093/nar/gkx054

Johnson, W. E., Li, C., & Rabinovic, A. (2007). Adjusting batch effects in microarray expression data using empirical Bayes methods. *Biostatistics,* 8(1), 118-127. doi.org/10.1093/BIOSTATISTICS/KXJ037

Knöfler, M., Haider, S., Saleh, L., Pollheimer, J., Gamage, T. K. J. B., & James, J. (2019 Sep. 1). Human placenta and trophoblast development: key molecular mechanisms and model systems. *Cellular and Molecular Life Sciences*. Birkhauser Verlag AG. doi.org/10.1007/s00018-019-03104-6

Kumar, A., D'Souza, S. S., Moskvin, O. V., Toh, H., Wang, B., Zhang, J., . . . . Slukvin, I. I. (2017). Specification and Diversification of Pericytes and Smooth Muscle Cells from Mesenchymoangioblasts. *Cell Reports,* 19(9), 1902-1916. doi.org/10.1016/j.celrep.2017.05.019

Kumar, N., Tsai, Y.-H., Chen, L., Zhou, A., Banerjee, K. K., Saxena, M., . . . . Verzi, M. P. (2019). The lineage-specific transcription factor CDX2 navigates dynamic chromatin to control distinct stages of intestine development. *Development,* 146(5), dev172189. doi.org/10.1242/dev.172189

Latos, P. A., & Hemberger, M. (2016 Oct. 15). From the stem of the placental tree: Trophoblast stem cells and their progeny. *Development* (*Cambridge*). Company of Biologists Ltd. doi.org/10.1242/dev.133462

Lee, C. Q. E., Gardner, L., Turco, M., Zhao, N., Murray, M. J., Coleman, N., . . . . Moffett, A. (2016). What Is Trophoblast? A Combination of Criteria Define Human First-Trimester Trophoblast. *Stem Cell Reports,* 6(2), 257-272. doi.org/10.1016/j.stemcr.2016.01.006

Li, Z., Kurosawa, O., & Iwata, H. (2019). Establishment of human trophoblast stem cells from human induced pluripotent stem cell-derived cystic cells under micromesh culture. *Stem Cell Research and Therapy,* 10(1). doi.org/10.1186/s13287-019-1339-1

Mischler, A., Karakis, V., Mahinthakumar, J., Carberry, C. K., Miguel, A. S., Rager, J. E., Fry, R. C., Rao, B. M., 2021. Two distinct trophectoderm lineage stem cells from human pluripotent stem cells. J. Biol. Chem. 296. doi.org/10.1016/j.jbc.2021.100386

Theunissen, T. W., Powell, B. E., Wang, H., Mitalipova, M., Faddah, D. A., Reddy, J., Fan, Z. P., Maetzel, D., Ganz, K., Shi, L., Lungjangwa, T., Imsoonthornruksa, S., Stelzer, Y., Rangarajan, S., D'Alessio, A., Zhang, J., Gao, Q., Dawlaty, M. M., Young, R. A., Gray, N. S., Jaenisch, R., 2014. Systematic identification of culture conditions for induction and maintenance of naive human pluripotency. Cell Stem Cell 15, 471-487. doi.org/10.1016/j.stem.2014.07.002

Wang, C. C., Jamal, L., Janes, K. A., 2012. Normal morphogenesis of epithelial tissues and progression of epithelial tumors. Wiley Interdiscip. Rev. Syst. Biol. Med. 4, 51-78. doi.org/10.1002/WSBM.159

Xu, R. H., Chen, X., Li, D. S., Li, R., Addicks, G. C., Glennon, C., . . . . Thomson, J. A. (2002). BMP4 initiates human embryonic stem cell differentiation to trophoblast. *Nature Biotechnology,* 20(12), 1261-1264. doi.org/10.1038/nbt761

Zhou, F., Wang, R., Yuan, P., Ren, Y., Mao, Y., Li, R., . . . . Tang, F. (2019). Reconstituting the transcriptome and DNA methylome landscapes of human implantation. *Nature,* 572(7771), 660-664. doi.org/10.1038/s41586-019-1500-0

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of producing a population of induced multipotent placental cells, the method comprising culturing a population of pluripotent stem cells in the presence of an induction media comprising a retinoid and a Wnt signaling agonist for between 4 to 6 days, under conditions suitable to produce the population of induced multipotent placental cells, wherein the induction media comprises from 0.1 to 10 μM of the retinoid and from 2 to 20 μM of the Wnt signaling agonist; and wherein the retinoid is retinoic acid, or a salt thereof, and the Wnt signaling agonist is selected from the group consisting of BIO, SB216763, CHIR-99021, and salts thereof.

2. The method of claim 1, wherein the Wnt signaling agonist is CHIR-99021, or a salt thereof.

3. The method of claim 1, wherein the induction media comprises a chemically defined basal media.

4. The method of claim 3, wherein the Wnt signaling agonist is CHIR-99021, or a salt thereof; and wherein the induction media further comprises a serum replacement, non-essential amino acids, L-alanyl-L-glutamine, and β-mercaptoethanol.

5. The method of claim 1, wherein the population of pluripotent stem cells are cultured in the presence of the induction media for 5 days.

6. The method of claim 5, wherein the Wnt signaling agonist is CHIR-99021, or a salt thereof.

7. The method of claim 1, wherein the population of induced multipotent placental cells comprises induced trophectoderm cells and/or induced trophoblast cells.

8. The method of claim 1, wherein:

1) The induced multipotent placental cells express CDX2 and one or more markers selected from the group consisting of Keratin 18 (KRT18), Keratin 7 (KRT7), KLF4, GATA3, E-cadherin, E74 like ETS transcription factor 5 (ELF5), one or more C19MC miRNAs, transcription factor AP-2 gamma (TFAP2C), HLA-G (HLA-G), and combinations thereof; and/or 2) the induced multipotent placental cells do not express OCT4, FoxA2, SOX17, and/or ITGB3.

9. The method of claim 1, further comprising culturing the population of induced multipotent placental cells under conditions suitable to produce a population of differentiated cells, wherein the differentiated cells are selected from the group consisting of syncytiotrophoblast (STB)-like cells and extravillous trophoblast (EVT)-like cells.

10. The method of claim 9, wherein:

1) The population of induced multipotent placental cells are cultured under normoxic conditions suitable to produce a population of STB-like cells, wherein the produced STB-like cells are multinucleated and/or are capable of secreting hCG; or 2) the population of induced multipotent placental cells are cultured under hypoxic conditions suitable to produce a population of EVT-like cells, wherein the produced EVT-like cells express Ki67 and/or an HLA-G marker.

11. The method of claim 1, wherein the induction media comprises 1 μM of retinoic acid, or a salt thereof, and 8 μM of CHIR-99021, or a salt thereof.

12. The method of claim 1, wherein at least 90% of the cells present after 4 to 6 days of being cultured in the presence of the induction media have differentiated into induced multipotent placental cells.

13. The method of claim 1, wherein the induction media further comprises L-glutamine or L-alanyl-L-glutamine.

* * * * *